United States Patent
Dai et al.

(10) Patent No.: US 12,404,275 B2
(45) Date of Patent: Sep. 2, 2025

(54) PYRAZOLOPYRAZINE DERIVED COMPOUNDS, PHARMACEUTICAL COMPOSITION AND USE THEREOF

(71) Applicant: PrimeGene (Beijing) Co., Ltd., Beijing (CN)

(72) Inventors: Liguang Dai, Beijing (CN); Li Zhu, Beijing (CN); Hui Zhang, Beijing (CN); Wei Wu, Beijing (CN); Yanqing Yang, Beijing (CN); Wei Hu, Beijing (CN)

(73) Assignee: PrimeGene (Beijing) Co., Ltd., Beijing (CN)

( * ) Notice: Subject to any disclaimer, the term of this patent is extended or adjusted under 35 U.S.C. 154(b) by 988 days.

(21) Appl. No.: 17/601,843

(22) PCT Filed: Apr. 10, 2020

(86) PCT No.: PCT/CN2020/084243
§ 371 (c)(1),
(2) Date: Oct. 6, 2021

(87) PCT Pub. No.: WO2020/207476
PCT Pub. Date: Oct. 15, 2020

(65) Prior Publication Data
US 2022/0204513 A1    Jun. 30, 2022

(30) Foreign Application Priority Data
Apr. 12, 2019    (CN) .......................... 201910294408.7

(51) Int. Cl.
C07D 487/04    (2006.01)
C07D 519/00    (2006.01)

(52) U.S. Cl.
CPC ......... C07D 487/04 (2013.01); C07D 519/00 (2013.01)

(58) Field of Classification Search
CPC .......................... C07D 487/04; C07D 519/00
See application file for complete search history.

(56) References Cited

U.S. PATENT DOCUMENTS

| | | |
|---|---|---|
| 2008/0312258 A1 | 12/2008 | Rodgers et al. |
| 2016/0333015 A1 | 11/2016 | Qin et al. |

FOREIGN PATENT DOCUMENTS

| | | |
|---|---|---|
| CN | 105524067 A | 4/2016 |
| CN | 106749338 A | 5/2017 |
| CN | 107513067 A | 12/2017 |
| CN | 109071546 A | 12/2018 |
| JP | 2017537950 A | 12/2017 |
| JP | 2018536634 A | 12/2018 |
| JP | 2019510003 A | 4/2019 |
| WO | 2011101161 A1 | 8/2011 |
| WO | 2011130146 A1 | 10/2011 |
| WO | 2013055645 A1 | 4/2013 |
| WO | 2016090285 A1 | 6/2016 |
| WO | 2017144995 A1 | 8/2017 |

(Continued)

OTHER PUBLICATIONS

Patani et. al. (Chem. Rev (1996) 96:3147-3176). (Year: 1996).*

(Continued)

*Primary Examiner* — Marcos L Sznaidman
(74) *Attorney, Agent, or Firm* — Fox Rothschild LLP

(57) ABSTRACT

Pyrazolopyrazine derived compounds as represented by general formulas (AI) and (I) or a pharmaceutically acceptable salt, a solvate, an active metabolite, a polymorph, an isotopic marker or an isomer thereof. Provided are a pharmaceutical composition comprising same and use of the compounds and the pharmaceutical composition in the preparation of medicaments for treating JAK kinase-mediated diseases. The compounds and pharmaceutical composition thereof provided have significant JAK kinase inhibitory activity, and in particular, have relatively high Tyk2 kinase inhibitory activity and selectivity for JAK2, and therefore have a very promising application potential.

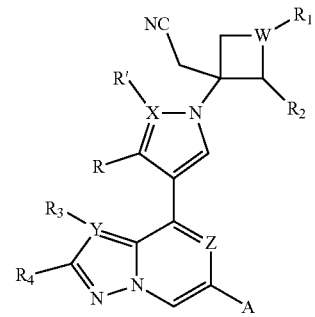

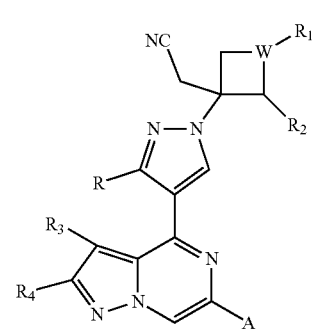

12 Claims, No Drawings

(56) References Cited

FOREIGN PATENT DOCUMENTS

WO WO 2017/144995 * 8/2017
WO 2019034973 A1 2/2019

OTHER PUBLICATIONS

Park et. al. (Annu. Rev. Pharmacol. Toxicol. (2001) 41:443-470). (Year: 2001).*
Japanese Notice of Reasons for Refusal issued on Sep. 29, 2022 for Japanese Patent Application No. 2021-559128 (25 pages).

* cited by examiner

PYRAZOLOPYRAZINE DERIVED COMPOUNDS, PHARMACEUTICAL COMPOSITION AND USE THEREOF

CROSS REFERENCE TO RELATED APPLICATIONS

This application is a U.S. national phase of International Patent Application No. PCT/CN2020/084243 filed on Apr. 10, 2020, which claims priority to Chinese Patent Application No. 201910294408.7 filed on Apr. 12, 2019. The content of the applications are incorporated herein by reference in its entirety.

TECHNICAL FIELD

The present disclosure relates to the pharmaceutical field, in particular to a pyrazolopyrazine derived compound, a pharmaceutical composition and use thereof.

BACKGROUND ART

Immunity and inflammation are important areas of drug research and development, and Janus kinase (JAK) target has been a research hotspot in the past decade. JAK/STAT signal pathway is a signal transduction pathway stimulated by cytokines, which participates in many important biological processes, such as cell proliferation, differentiation, apoptosis and immune regulation. JAK kinase contains 4 family members, namely JAK1, JAK2, JAK3 and Tyk2. The activation of this signaling pathway is closely related to the occurrence and development of many diseases, including various inflammatory diseases, lymphoma, leukemia and solid tumors, etc.

At present, the FDA has approved four JAK inhibitors. Ruxolitinib jointly developed by Incyte and Novartis was approved for the treatment of polycythemia vera (PCV) in November 2011; Tofacitnib from Pfizer was approved for the treatment of rheumatoid arthritis in November 2012, and later approved for the treatment of psoriatic arthritis and ulcerative colitis; Baricitinib, jointly developed by Incyte and Eli Lilly, was approved for the treatment of rheumatoid arthritis in May 2018; Oclacitinib, an oral formulation developed by Zoetis, was approved in May 2013 for the treatment of canine atopic dermatitis.

JAK inhibitors have also made good progress in other indications such as atopic dermatitis, psoriasis, alopecia areata, etc. Studies have found that the main factors involved in the pathogenesis of psoriasis are T cells, dendritic cells, keratinocytes, changes in the functions of mast cells and macrophages. These cells and their related cytokines and chemokines interact each other and mediate a series of inflammatory reactions, epidermal proliferation, hypokeratosis, spinal hypertrophy, vascular changes, etc. The related main targets are tumor necrosis factor-α (TNF-α), phosphodiesterase 4 (PDE4), JAK kinases, interleukins and their receptors (IL & ILR), etc.

IL-12, IL-17 and IL-23 are the main targets of drugs for treating psoriasis in the IL family. Targeting IL-12/23 downstream effector Tyk2 is a good research direction. The expression of Tyk2 in dendritic cells is necessary for the production of IL-12, IL-23 and IFN-γ and the induction of Th1 cell differentiation (Blood, 2007), and IL-23 secreted by dendritic cells can induce Th17 cells to secrete inflammatory mediators, such as IL-17A, IL-17F, IL-22, etc. These inflammatory mediators will promote the activation and proliferation of epidermal keratinocytes (KC). Through the interaction of Th17 and KC cells, KC cells are activated and produce pro-inflammatory factors, chemokines, and antibacterial peptides, which can recruit and activate immune cells to the site of inflamed skin. This leads to the expansion of the immune response and eventually develops clinical symptoms related to psoriasis. It can be seen that Tyk2 plays a very important role in the occurrence and development of psoriasis. Targeting and inhibiting Tyk2 is expected to control the disease at the initial stage of inflammation.

SUMMARY

In one aspect, the disclosure provides a novel pyrazolopyrazine derived compound or a pharmaceutically acceptable salt, solvate, active metabolite, polymorph, isotopically labelled compound, isomer or prodrug thereof, exhibiting excellent inhibitory activity of JAK.

In another aspect, the disclosure provides a pharmaceutical composition.

In another aspect, the disclosure provides use of the above compound or a pharmaceutically acceptable salt, solvate, active metabolite, polymorph, isotopically labelled compound, isomer or prodrug thereof.

The present disclosure provides a pyrazolopyrazine derived compound represented by general formula (AI) or a pharmaceutically acceptable salt, solvate, active metabolite, polymorph, isotopically labelled compound or isomer,

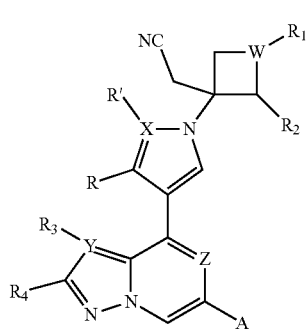

AI wherein,
$WR_1$ represents —$(CR_5R_1)$— or —$(NR_1)$—;
A represents —OR" or

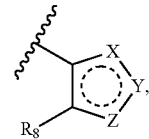

where X, Y, Z independently represent —O—, —S—, —(CO)—, —(CS)—, —$(CR_6)$=, —$(CR_6R_7)$—, —N= or —$(NR_6)$—, and make the formed five-membered ring an unsaturated ring; $R_6$, $R_7$ independently represent substituted or unsubstituted hydrogen, halogen, $C_{1-6}$ alkyl, $C_{1-6}$ alkoxy, $C_{1-6}$ haloalkyl, hydroxy, mercapto, amino, cyano, $C_{1-4}$ hydroxyalkylene, $C_{1-4}$ mercaptoalkylene, $C_{1-4}$ aminoalkylene, $C_{1-4}$ cyanoalkylene, —$NR_9COR_{10}$, —$COR_9$ or —$CONR_9R_{10}$;

R" represents $C_1$-$C_6$ alkyl substituted with hydroxy, methoxy or amino;

R represents halogen, substituted or unsubstituted —$NR_9R_{10}$, or R' and R and the atoms on the ring to which they are connected together form a six-membered or five-membered aromatic ring or heteroaromatic ring;

XR' represents —(N)— or —(CR')—, and when XR' represents —(CR')—, R' and R and the atoms on the ring to which they are connected together form a six-membered or five-membered aromatic ring or heteroaromatic ring;

$YR_3$ represents —(N)— or —($CR_3$)—;

Z represents —N— or —$CR_3$—;

$R_1$ represents —$(CH_2)_n$—$R_{1'}$, where $R_{1'}$ represents substituted or unsubstituted hydrogen, halogen, $C_{1~6}$ alkyl, $C_{1~6}$ alkoxy, $C_{1~6}$ haloalkyl, hydroxy, mercapto, amino, cyano, $C_{3~8}$ cycloalkyl, $C_{3~8}$ heterocyclyl, $C_{6~20}$ aryl, $C_{3~20}$ heteroaryl, —$NR_9COR_{10}$, —$CONR_9R_{10}$, —$COR_9$, —$SOR_9$ or —$SO_2R_9$, n represents an integer from 0 to 4;

$R_2$~$R_5$ independently represent substituted or unsubstituted hydrogen, halogen, $C_{1~6}$ alkyl, $C_{1~6}$ alkoxy, $C_{1~6}$ haloalkyl, hydroxy, mercapto, amino or cyano;

$R_8$ represents —$(CH_2)_n$—$R_{8'}$, where $R_{8'}$ represents substituted or unsubstituted hydrogen, halogen, $C_{1~6}$ alkyl, $C_{1~6}$ alkoxy, $C_{1~6}$ haloalkyl, hydroxy, mercapto, cyano or —$NR_9R_{10}$, and n represents an integer from 0 to 4;

$R_9$, $R_{10}$ independently represent substituted or unsubstituted hydrogen, halogen, $C_{1~6}$ alkyl, $C_{1~6}$ alkoxy, $C_{1~6}$ haloalkyl, hydroxy, mercapto, amino, cyano, $C_{3~8}$ cycloalkyl or $C_{3~8}$ heterocyclyl;

The substituents of the above groups may be selected from halogen, $C_{1~6}$ alkyl, $C_{1~6}$ haloalkyl, $C_{1~6}$ alkoxy, $C_{1~6}$ alkylsulfanyl, $C_{3~8}$ cycloalkyl, $C_{3~8}$ heterocyclyl, $C_{6~20}$ aryl, $C_{3~20}$ heteroaryl, $C_{1~6}$ alkyl ester group, $C_{1~6}$ alkyl acyl, $C_{1~6}$ alkylsufonyl, amino, hydroxyl, mercapto, carboxyl, nitro, amido, or cyano.

The present disclosure provides a pyrazolopyrazine derived compound represented by general formula (I) or a pharmaceutically acceptable salt, solvate, active metabolite, polymorph, isotopically labelled compound or isomer,

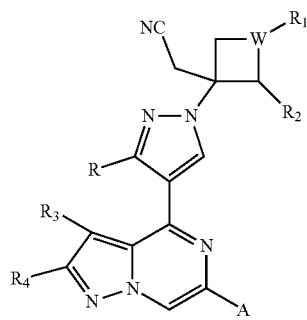

wherein,
$WR_1$ represents —($CR_5R_1$)— or —($NR_1$)—;
A represents

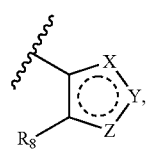

and X, Y, Z independently represent —O—, —S—, —(CO)—, —(CS)—, —($CR_6$)=, —($CR_6R_7$)—, —N= or —($NR_6$)—, and make the formed five-membered ring an unsaturated ring; $R_6$, $R_7$ independently represent substituted or unsubstituted hydrogen, halogen, $C_{1~6}$ alkyl, $C_{1~6}$ alkoxy, $C_{1~6}$ haloalkyl, hydroxy, mercapto, amino, cyano, $C_{1~4}$ hydroxyalkylene, $C_{1~4}$ mercaptoalkylene, $C_{1~4}$ aminoalkylene, $C_{1~4}$ cyanoalkylene, —$NR_9COR_{10}$, —$COR_9$ or —$CONR_9R_{10}$;

R The present disclosure provides a pyrazolopyrazine derived compound represented by general formula (AI) or a pharmaceutically acceptable salt, solvate, active metabolite, polymorph, isotopically labelled compound or isomer, substituted or unsubstituted —$NR_9R_{10}$;

$R_1$ represents —$(CH_2)_n$—$R_{1'}$, $R_{1'}$ represents substituted or unsubstituted hydrogen, halogen, $C_{1~6}$ alkyl, $C_{1~6}$ alkoxy, $C_{1~6}$ haloalkyl, hydroxy, mercapto, amino, cyano, $C_{3~8}$ cycloalkyl, $C_{3~8}$ heterocyclyl, $C_{6~20}$ aryl, $C_{3~20}$ heteroaryl, —$NR_9COR_{10}$, —$CONR_9R_{10}$, —$COR_9$, —$SOR_9$ or —$SO_2R_9$, n represents an integer from 0 to 4;

$R_2$~$R_5$ independently represent substituted or unsubstituted hydrogen, halogen, $C_{1~6}$ alkyl, $C_{1~6}$ alkoxy, $C_{1~6}$ haloalkyl, hydroxy, mercapto, amino or cyano;

$R_8$ represents —$(CH_2)_n$—$R_{8'}$, $R_{8'}$ represents substituted or unsubstituted hydrogen, halogen, $C_{1~6}$ alkyl, $C_{1~6}$ alkoxy, $C_{1~6}$ haloalkyl, hydroxy, mercapto, cyano or —$NR_9R_{10}$, n represents an integer from 0 to 4;

$R_9$, $R_{10}$ independently represent substituted or unsubstituted hydrogen, halogen, $C_{1~6}$ alkyl, $C_{1~6}$ alkoxy, $C_{1~6}$ haloalkyl, hydroxy, mercapto, amino, cyano, $C_{3~8}$ cycloalkyl or $C_{3~8}$ heterocyclyl;

The substituents of the above groups may be selected from halogen, $C_{1~6}$ alkyl, $C_{1~6}$ haloalkyl, $C_{1~6}$ alkoxy, $C_{1~6}$ alkylsulfanyl, $C_{3~8}$ cycloalkyl, $C_{3~8}$ heterocyclyl, $C_{6~20}$ aryl, $C_{3~20}$ heteroaryl, $C_{1~6}$ alkyl ester group, $C_{1~6}$ alkyl acyl, $C_{1~6}$ alkylsufonyl, amino, hydroxyl, mercapto, carboxyl, nitro, amido, or cyano.

The present disclosure provides a pyrazolopyrazine derived compound represented by general formula (I) or a pharmaceutically acceptable salt, solvate, active metabolite, polymorph, isotopically labelled compound or isomer,

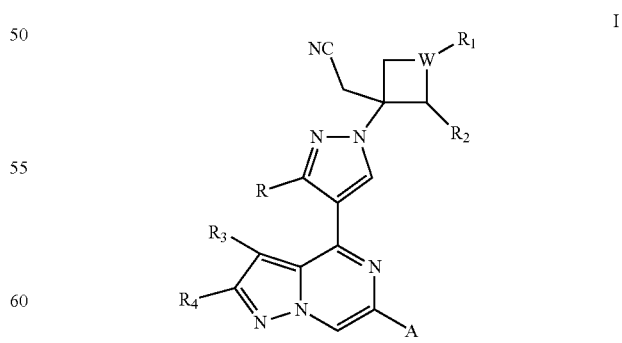

wherein,
WR$_1$ represents —(CR$_5$R$_1$)— or —(NR$_1$)—;
A represents

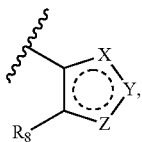

X, Y, Z independently represent —O—, —S—, —(CO)—, —(CS)—, —(CR$_6$)—, —(CR$_6$R$_7$)—, —N═ or —(NR$_6$)—, and make the formed five-membered ring an unsaturated ring; R$_6$, R$_7$ independently represent substituted or unsubstituted hydrogen, halogen, C$_{1\sim6}$ alkyl, C$_{1\sim6}$ alkoxy, C$_{1\sim6}$ haloalkyl, hydroxy, mercapto, amino, cyano, C$_{1\sim4}$ hydroxyalkylene, C$_{1\sim4}$ mercaptoalkylene, C$_{1\sim4}$ aminoalkylene, C$_{1\sim4}$ cyanoalkylene, —NR$_9$COR$_{10}$, —COR$_9$ or —CONR$_9$R$_{10}$;

R represents halogen;

R$_1$ represents —(CH$_2$)$_n$—R$_{1'}$, where R$_{1'}$ represents substituted or unsubstituted hydrogen, halogen, C$_{1\sim6}$ alkyl, C$_{1\sim6}$ alkoxy, C$_{1\sim6}$ haloalkyl, hydroxy, mercapto, amino, cyano, C$_{3\sim8}$ cycloalkyl, C$_{3\sim8}$ heterocyclyl, C$_{6\sim20}$ aryl, C$_{3\sim20}$ heteroaryl, —NR$_9$COR$_{10}$, —CONR$_9$R$_{10}$, —COR$_9$, —SOR$_9$ or —SO$_2$R$_9$, and n represents an integer from 0 to 4;

R$_2$~R$_5$ independently represent substituted or unsubstituted hydrogen, halogen, C$_{1\sim6}$ alkyl, C$_{1\sim6}$ alkoxy, C$_{1\sim6}$ haloalkyl, hydroxy, mercapto, amino or cyano;

R$_8$ represents —(CH$_2$)$_n$—R$_{8'}$, where R$_{8'}$ represents substituted or unsubstituted hydrogen, halogen, C$_{1\sim6}$ alkyl, C$_{1\sim6}$ alkoxy, C$_{1\sim6}$ haloalkyl, hydroxy, mercapto, cyano or —NR$_9$R$_{10}$, and n represents an integer from 0 to 4;

R$_9$, R$_{10}$ independently represent substituted or unsubstituted hydrogen, halogen, C$_{1\sim6}$ alkyl, C$_{1\sim6}$ alkoxy, C$_{1\sim6}$ haloalkyl, hydroxy, mercapto, amino, cyano, C$_{3\sim8}$ cycloalkyl or C$_{3\sim8}$ heterocyclyl;

The substituents of the above groups may be selected from halogen, C$_{1\sim6}$ alkyl, C$_{1\sim6}$ haloalkyl, C$_{1\sim6}$ alkoxy, C$_{1\sim6}$ alkylsulfanyl, C$_{3\sim8}$ cycloalkyl, C$_{3\sim8}$ heterocyclyl, C$_{6\sim20}$ aryl, C$_{3\sim20}$ heteroaryl, C$_{1\sim6}$ alkyl ester group, C$_{1\sim6}$ alkyl carbonyloxy, C$_{1\sim6}$ alkyl acyl, C$_{1\sim6}$ alkylamino, C$_{1\sim6}$ alkylsufonyl, amino, hydroxyl, mercapto, carboxyl, nitro, amido, or cyano.

The present disclosure provides a pyrazolopyrazine derived compound represented by general formula (I) or a pharmaceutically acceptable salt, solvate, active metabolite, polymorph, isotopically labelled compound or isomer,

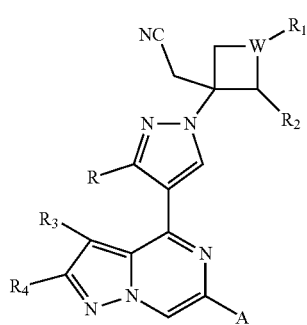

I wherein,
WR$_1$ represents —(CR$_5$R$_1$)— or —(NR$_1$)—;
A represents —OR", where R" represents C$_1$-C$_6$ alkyl substituted with hydroxy, methoxy or amino;
R represents halogen, substituted or unsubstituted —NR$_9$R$_{10}$;
R$_1$ represents —(CH$_2$)$_n$—R$_{1'}$, and R$_{1'}$ represents substituted or unsubstituted hydrogen, halogen, C$_{1\sim6}$ alkyl, C$_{1\sim6}$ alkoxy, C$_{1\sim6}$ haloalkyl, hydroxy, mercapto, amino, cyano, C$_{3\sim8}$ cycloalkyl, C$_{3\sim8}$ heterocyclyl, C$_{6\sim20}$ aryl, C$_{3\sim20}$ heteroaryl, —NR$_9$COR$_{10}$, —CONR$_9$R$_{10}$, —COR$_9$, —SOR$_9$ or —SO$_2$R$_9$, n represents an integer from 0 to 4;

R$_2$~R$_5$ independently represent substituted or unsubstituted hydrogen, halogen, C$_{1\sim6}$ alkyl, C$_{1\sim6}$ alkoxy, C$_{1\sim6}$ haloalkyl, hydroxy, mercapto, amino or cyano;

R$_8$ represents —(CH$_2$)$_n$—R8', where R$_{8'}$ represents substituted or unsubstituted hydrogen, halogen, C$_{1\sim6}$ alkyl, C$_{1\sim6}$ alkoxy, C$_{1\sim6}$ haloalkyl, hydroxy, mercapto, cyano or —NR$_9$R$_{10}$, and n represents an integer from 0 to 4;

R$_9$, R$_{10}$ independently represent substituted or unsubstituted hydrogen, halogen, C$_{1\sim6}$ alkyl, C$_{1\sim6}$ alkoxy, C$_{1\sim6}$ haloalkyl, hydroxy, mercapto, amino, cyano, C$_{3\sim8}$ cycloalkyl or C$_{3\sim8}$ heterocyclyl;

The substituents of the above groups may be selected from halogen, C$_{1\sim8}$ alkyl, C$_{2\sim8}$ alkenyl, C$_{2\sim8}$ alkynyl, C$_{1\sim8}$ haloalkyl, C$_{1\sim8}$ alkoxyl, C$_{1\sim8}$ alkylsulfanyl, C$_{3\sim8}$ cycloalkyl, C$_{3\sim8}$ heterocyclyl, C$_{6\sim20}$ aryl, C$_{2\sim20}$ heteroaryl, C$_{1\sim6}$ alkyl ester group C$_{1\sim6}$ alkyl carbonyloxy, C$_{1\sim6}$ alkyl acyl, C$_{1\sim6}$ alkylamino, C$_{1\sim6}$ alkylsufonyl, amino, hydroxyl, mercapto, carboxyl, nitro, amido, or cyano.

In the above general formula (AI) or (I), the groups represented by R, R$_1$~R$_{10}$, R$_{1'}$, R$_{8'}$ and their optional substituents include but are not limited to:

Hydrogen may be expressed as —H, and may also be replaced with deuterium or tritium.

Halogen may include fluorine, chlorine, bromine, and iodine.

C$_{1\sim6}$ alkyl may include methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-Pentyl, 4-methyl-1-pentyl, 2-methyl-2-pentyl, 3-methyl-2-pentyl, 4-methyl-2-pentyl, 2,2-dimethyl Base-1-butyl, 3,3-dimethyl-1-butyl, 2-ethyl-1-butyl, n-butyl, isobutyl, sec-butyl, tert-butyl, n-pentyl, iso-amyl, neopentyl, tert-amyl, hexyl, etc.

C$_{1\sim6}$ alkoxy may be represented as —O—C$_{1\sim6}$ alkyl, wherein the C$_{1\sim6}$ alkyl may include the groups as defined above; for example, the C$_{1\sim6}$ alkoxy may include methoxy, ethoxy, n-propoxy, isopropoxy, n-butoxy, isobutoxy, sec-butoxy, tert-butoxy, etc.

C$_{1\sim6}$ alkylsulfanyl may be represented as —S—C$_{1\sim6}$ alkyl, wherein the C$_{1\sim6}$ alkyl may include the groups as defined above; for example, the C$_{1\sim6}$ alkylsulfanyl may include methylsulfanyl, ethylsulfanyl, etc.

C$_{1\sim6}$ haloalkyl may be represented as a group in which any number of hydrogen atoms in the C$_{1\sim6}$ alkyl is substituted by halogen, wherein the groups included in C$_{1\sim6}$ alkyl and in halogen are as listed above; for example, C$_{1\sim6}$ haloalkyl may include —CF$_3$.

C$_{1\sim6}$ alkylene is a divalent functional group with two substitutable bonds, which may include linear alkylene and branched alkylene, and linear alkylene may be expressed as —(CH$_2$)$_m$—, m represents 1 to 6, and may include, for example, methylene, ethylene, etc. C$_{3\sim8}$ cycloalkyl may represent a non-aromatic saturated carbocyclic ring, including single-carbon ring (with one ring) and bi-carbon ring (with two rings). For example, C$_{3\sim8}$ cycloalkyl may include

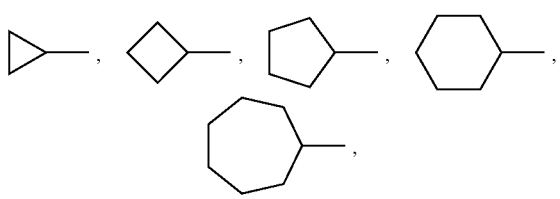

or the like.

$C_{3~8}$ heterocyclyl (or heterocyclic group) may represent a group obtained by replacing any number of ring atoms in $C_{3~8}$ cycloalkyl with heteroatoms such as O, S, N, P, Si, etc, wherein $C_{3~8}$ cycloalkyl includes those defined as above. For example, $C_{3~8}$ heterocyclic group may include oxiranyl, sulfiethanyl, azaethyl, azetidinyl, oxbutanyl, thibutyryl, tetrahydrofuranyl, pyrrolidinyl, oxazolidinyl, tetrahydropyrazolyl, pyrrolinyl, dihydrofuranyl, dihydrothienyl, piperidinyl, tetrahydropyranyl, tetrahydrothiopyranyl, morpholinyl, piperazinyl, dihydropyridinyl, tetrahydropyranyl, dihydropyranyl, tetrahydropyranyl, dihydrothiopyranyl, azacycloheptyl, oxacycloheptyl, thiacycloheptyl, oxaaza bicyclo[2.2.1]heptyl, azaspiro[3.3]heptyl, etc.

$C_{6~20}$ aryl may include a monocyclic aryl group, a bicyclic aryl group, or a multi-ring aryl group. For example, it may include phenyl, biphenyl, naphthyl, phenanthryl, anthryl, azulenyl, and the like.

$C_{3~20}$ heteroaryl may represent an unsaturated group containing any number of heteroatoms such as O, S, N, P, and Si as ring atoms. The number of carbon atoms in heteroaryl may be 3-20, for example, 3, 4, 5, 6, 7, 8, 9, 10, or more than 10. For example, $C_{2-20}$ heteroaryl may include pyrrolyl, furyl, thienyl, imidazolyl, oxazolyl, pyrazolyl, pyridyl, pyrimidinyl, pyrazinyl, quinolinyl, isoquinolinyl, tetrazolyl, triazolyl, triazinyl, benzofuranyl, benzothienyl, indolyl, isoindolyl, etc.

Hydroxyl may be expressed as —OH.

Mercapto may be represented as —SH.

Nitro may be expressed as —NO$_2$.

Cyano may be represented as —CN.

Carboxyl may be expressed as —COOH, and the H of the carboxyl group may also be substituted by a substituent to form the corresponding ester group, which may be expressed as —COOR$_a$. R$_a$ may be the substituents described in the general formula (AI) or (I), for example, an ester group substituted by $C_{1~6}$ alkyl may be represented as —COOC$_{1~6}$ alkyl group, and the $C_{1~6}$ alkyl group is as defined above.

Preferably, the ester group is a $C_{1~4}$ alkyl ester group, and the $C_{1~4}$ alkyl group may include all groups with carbon atoms of 1-4 in the aforementioned definition of "$C_{1~6}$ alkyl".

The sulfonyl group may be represented as —S(O)$_2$R$_a$, R$_a$ may be the substituents described in the general formula (AI) or (I). For example, a sulfonyl group substituted with a $C_{1~6}$ alkyl group may be represented as —S(O)$_2$C$_{1~6}$ alkyl, wherein the $C_{1~6}$ alkyl is as defined above.

Preferably, the sulfonyl group is $C_{1~4}$ alkylsufonyl, and the $C_{1~4}$ alkyl group may include all groups with carbon atoms of 1 to 4 in the aforementioned definition of "$C_{1~6}$ alkyl".

The acyl group may be represented as —COR$_a$, R$_a$ may be the substituents described in the general formula (AI) or (I). For example, an acyl group substituted with a $C_{1~6}$ alkyl group may be represented as —COC$_{1~6}$ alkyl, wherein the $C_{1~6}$ alkyl is as defined above.

Preferably, the acyl group is $C_{1~4}$ alkylacyl, and the $C_{1~4}$ alkyl group may include all groups with carbon atoms of 1 to 4 in the aforementioned definition of "$C_{1~6}$ alkyl".

The amino group may be represented as —NH$_2$, —NHR$_a$ or —N(R$_a$)$_2$, and R$_a$ may be the substituents described in the general formula (AI) or (I). For example, an amino group substituted with a $C_{1~6}$ alkyl group may be represented as —NHC$_{1~6}$ alkyl or —N(C$_{1~6}$ alkyl)$_2$, wherein the $C_{1~6}$ alkyl is as defined above.

Preferably, the amino group is $C_{1~4}$ alkylamino, and the $C_{1~4}$ alkyl group may include all groups with carbon atoms of 1 to 4 in the aforementioned definition of "$C_{1~6}$ alkyl".

The amido group may be represented as —CO-amino, and the amino group is as defined above.

In the foregoing definitions, when the number of carbon atoms changes, the above definitions only change according to the change in the number of carbon atoms, and does not affect the definition of the group type. For example, "$C_{1~4}$ alkyl" may include all groups meeting number of carbon atoms of 1 to 4 in the definition of "$C_{1~6}$ alkyl", such as methyl, ethyl, and n-propyl, isopropyl, n-butyl, isobutyl, sec-butyl, tert-butyl, etc.

In the foregoing definitions, the atoms in each group, such as C, H, O, N, S, etc., may be independently replaced with their isotopes. For example, hydrogen may be replaced with deuterium, tritium, etc., and $C_{1~8}$ alkyl may be replace with deuterated $C_{1~8}$ alkyl, including but not limited to deuterated methyl, deuterated ethyl, deuterated n-propyl, deuterated isopropyl, deuterated n-butyl, deuterated isobutyl, deuterated sec-butyl Base, deuterated tert-butyl, etc.

In an embodiment according to the present disclosure, the choice of X, Y, and Z needs to make the formed five-membered ring an unsaturated ring. The ring can contain one or two double bonds, and adjacent groups need to meet the valence requirement.

In some embodiments according to the disclosure, the symbol "A" represents one of the following groups:

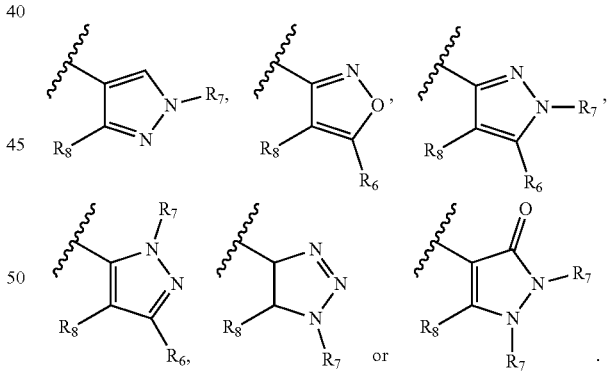

In some embodiments according to the disclosure, the symbol "A" represents the following group:

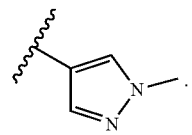 [SMILES: *c1cnn(C)c1]

In some embodiments according to the disclosure, the symbol "A" represents the following group:

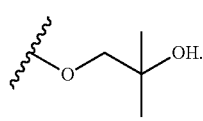

In some embodiments according to the disclosure, R may represent —NH$_2$.

In some embodiments according to the disclosure, R$_1$ represents —(CH$_2$)$_n$—R$_{1'}$, n may represent an integer which is 0 or is not 0; when n represents 0, R$_{1'}$ is R$_1$; when n represents an integer which is not 0, it may be 1, 2, 3 or 4, —(CH$_2$)$_n$— is linear or branched alkylene; preferably, n may represent 1 or 2.

In some embodiments according to the disclosure, R$_{1'}$ may further represent hydrogen, C$_{1-4}$ alkyl, C$_{1-4}$ alkoxy, C$_{1-4}$ haloalkyl, hydroxy, cyano, C$_{3-6}$ cycloalkyl, C$_{3-5}$ heteroaryl, —COR$_9$ or —SO$_2$R$_9$; and R$_9$ represents C$_{1-4}$ alkyl, C$_{1-4}$ alkoxy, C$_{1-4}$ haloalkyl or C$_{3-6}$ cycloalkyl. Preferably, when R$_{1'}$ represents C$_{3-5}$ heteroaryl, it may represent N atom containing heteroaryl, and the number of the N atoms may be 1, 2 or 3; for example, it may be pyrazolyl, pyridyl, pyrimidinyl, pyrazinyl, triazolyl, triazinyl etc.

In some embodiments according to the disclosure, the compound may be selected from:

1

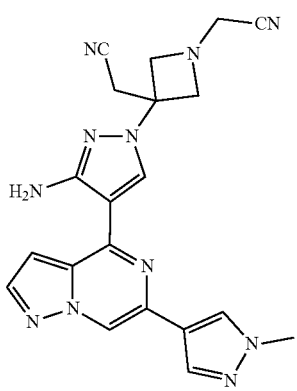

2

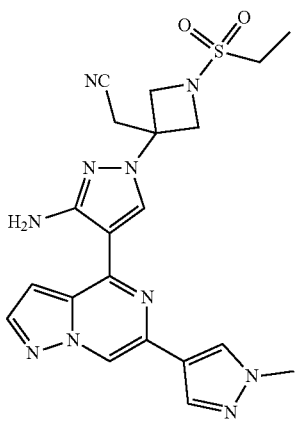

3

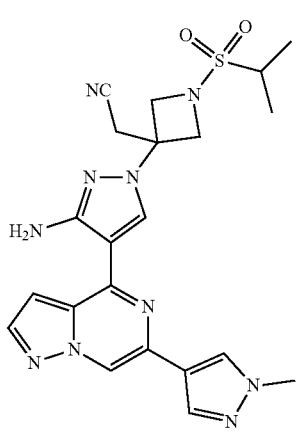

4

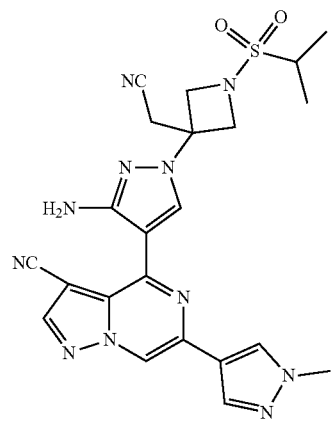

5

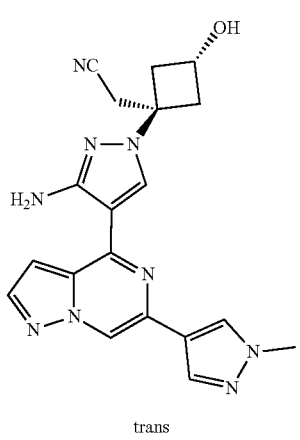

trans

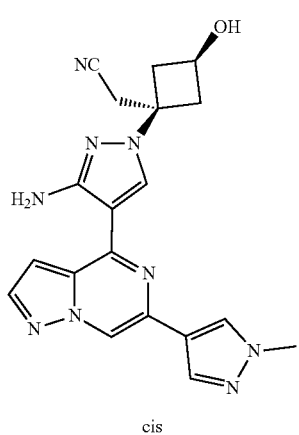
6
cis
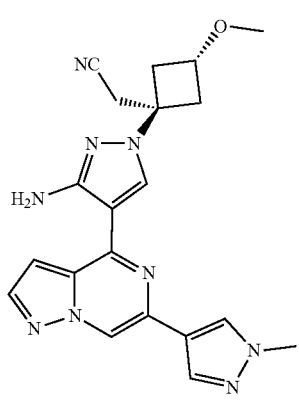
7
trans
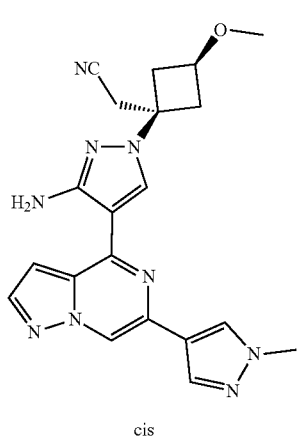
8
cis
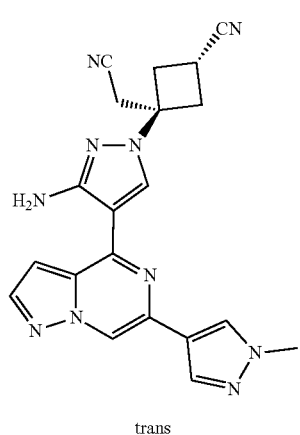
9
trans
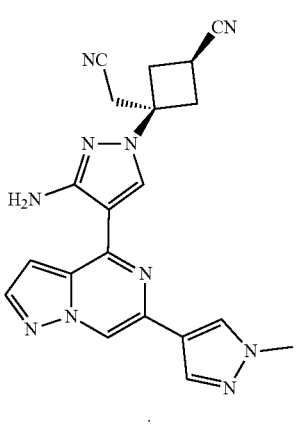
10
cis
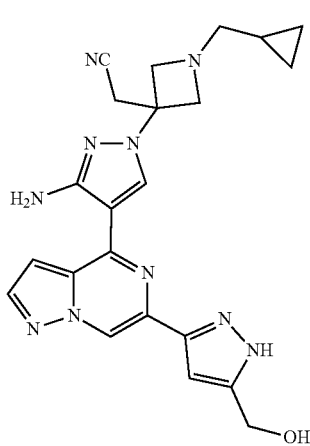
11

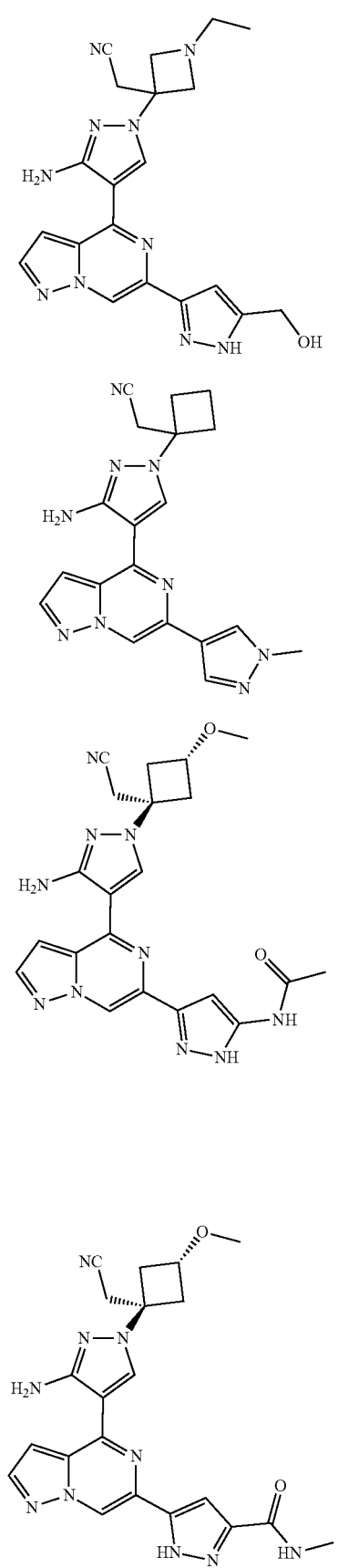
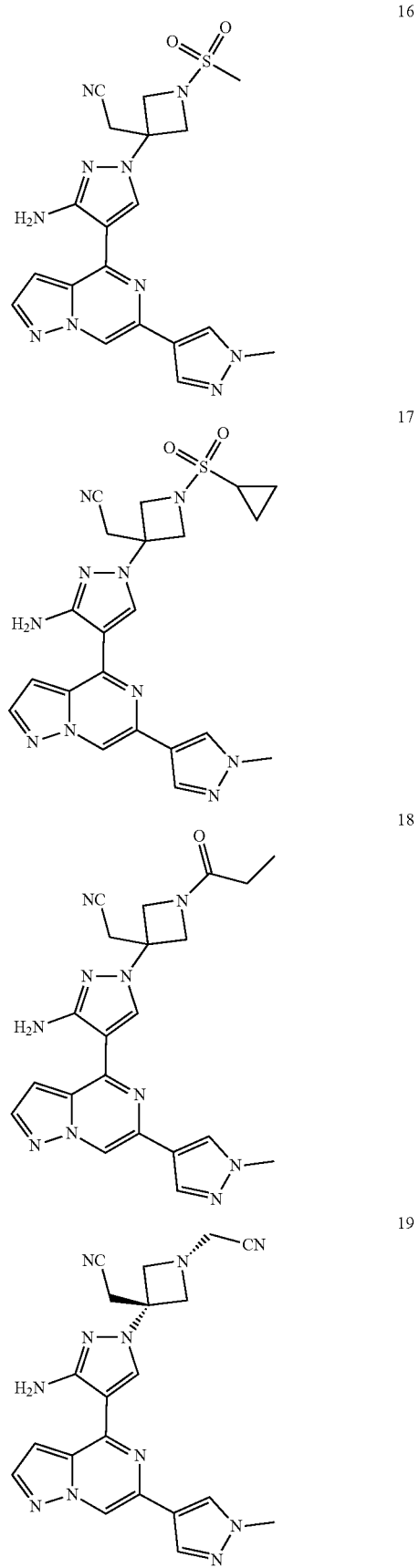

20
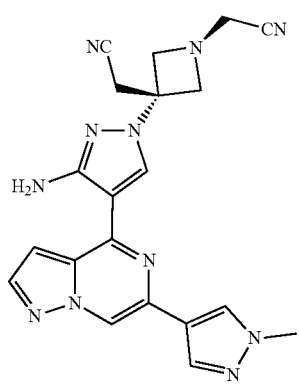
21
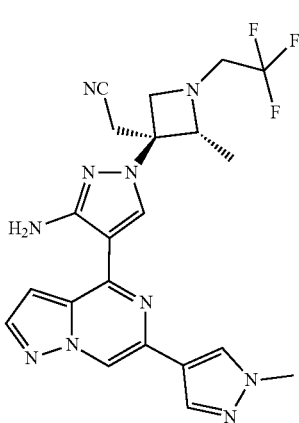
22
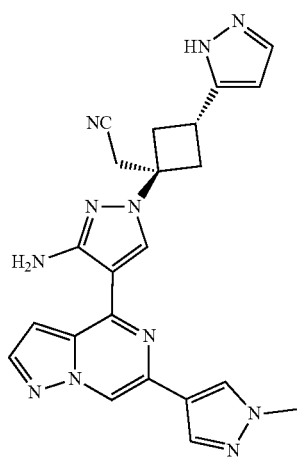
23
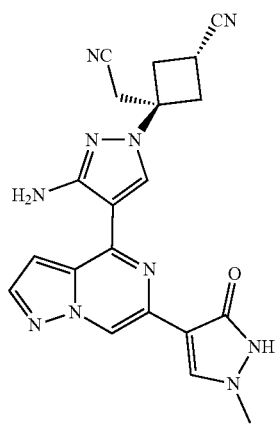
24
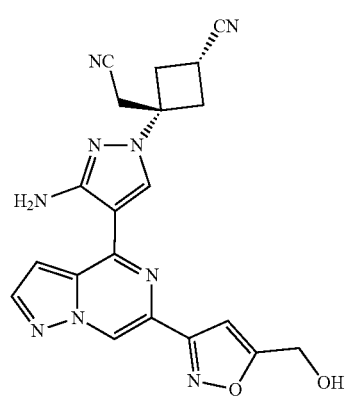
25
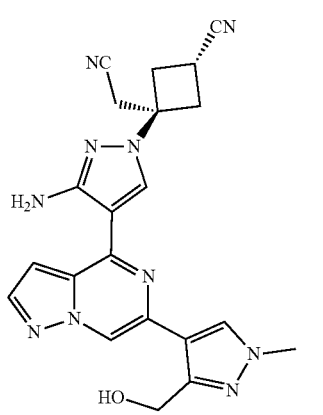
26
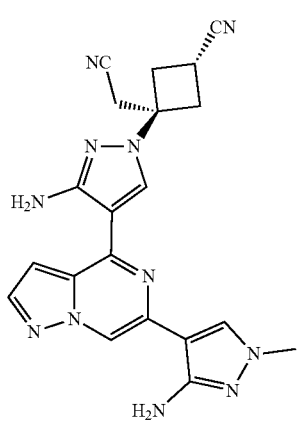

-continued
27
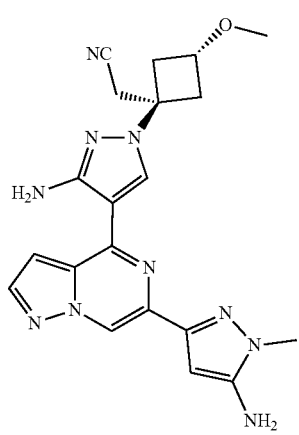
28
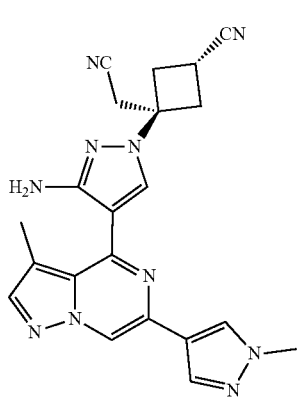
29
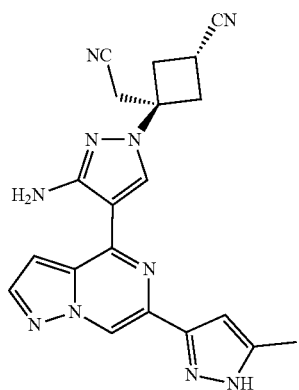
-continued
30
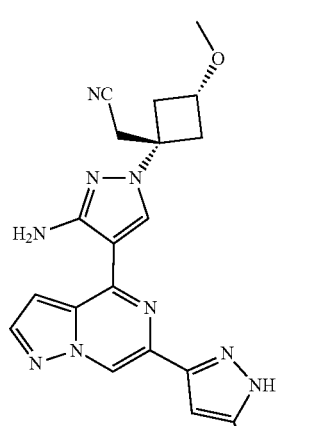
31
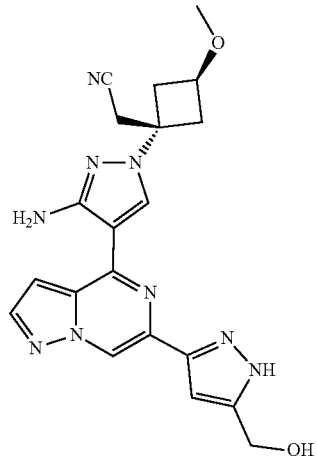
32
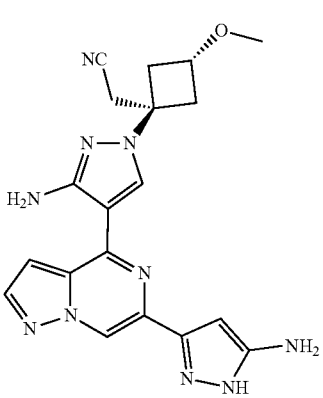

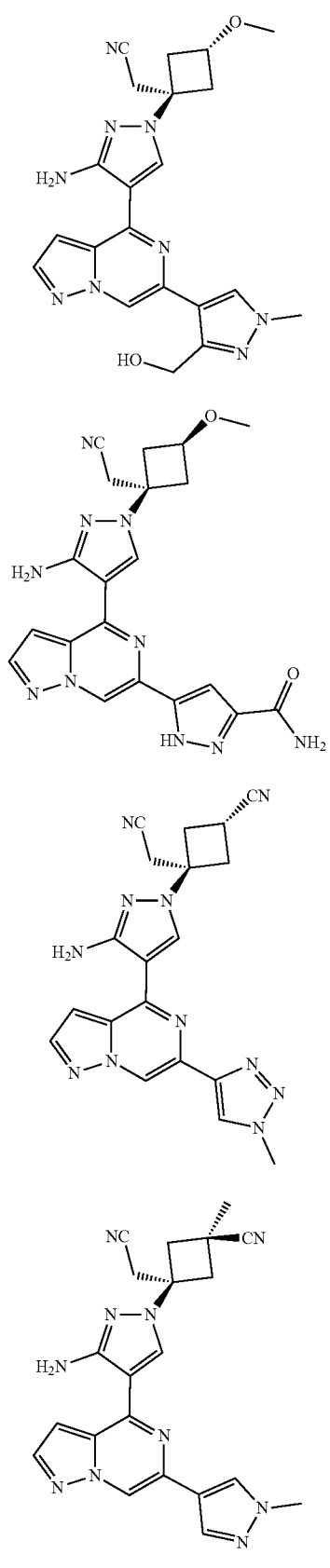

41
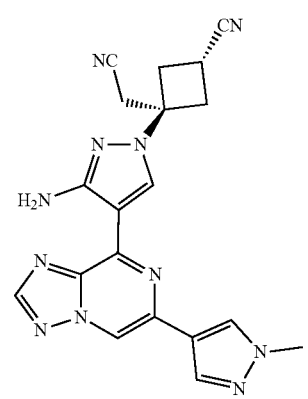
42
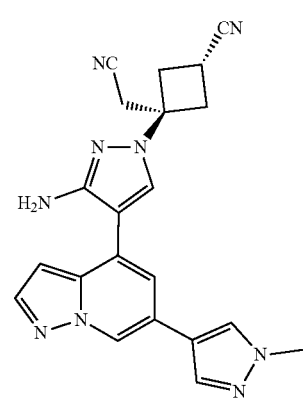
43
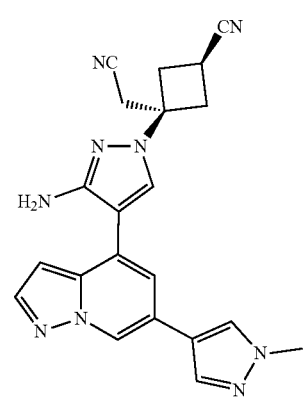
44
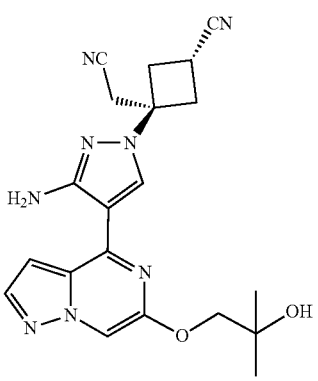
45
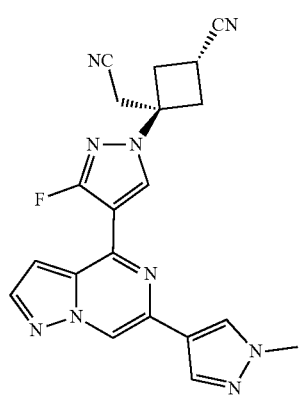
46
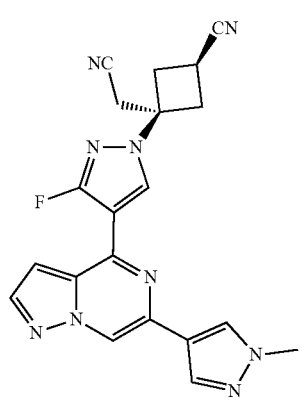
47
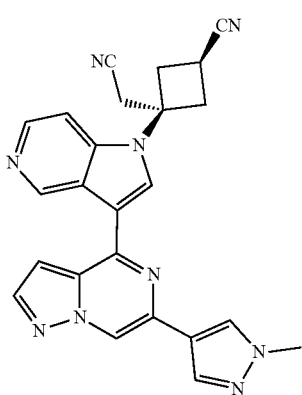
48
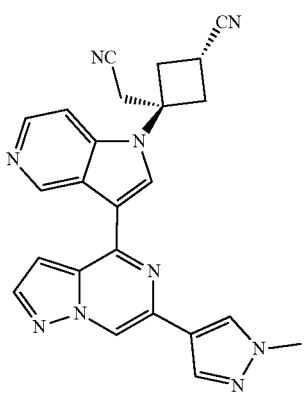

-continued

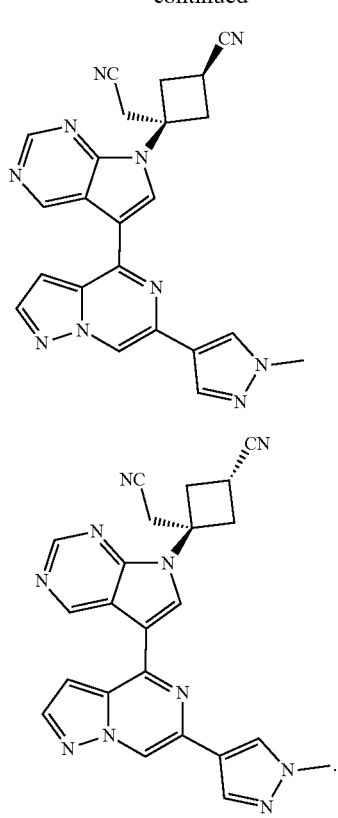

The present disclosure also provides a pharmaceutical composition containing the compound described in any one of the above technical solutions or a pharmaceutically acceptable salt, solvate, active metabolite, polymorph, isotopically labelled compound or isomer thereof, and a pharmaceutically acceptable carrier.

In some embodiments of the pharmaceutical composition according to the present disclosure, the pharmaceutical composition may be any common dosage form such as oral dosage form and injection dosage form, including but not limited to oral dosage forms, parenteral dosage forms, topical dosage forms, rectal dosage forms and the like. For example, the pharmaceutical composition may be tablets, capsules, pills, powders, sustained-release preparations, solutions and suspensions for oral administration; sterile solutions, suspensions or emulsions for parenteral administration; and ointments, creams, gels, etc. for topical use; or suppositories for rectal administration.

The present disclosure also provides the above-mentioned compounds or their pharmaceutically acceptable salts, solvates, active metabolites, polymorphs, isotopically labelled compound, isomers or prodrugs, and the above-mentioned pharmaceutical compositions in the preparation of a medicament for treating JAK mediated diseases.

The JAK mediated diseases include tumors or autoimmune diseases.

Further, the JAK mediated diseases may include, but are not limited to, leukemia, non-small cell lung cancer, colon cancer, lymphoma, myeloproliferative tumors, myelodysplastic syndromes and other tumors; also include but are not limited to rheumatoid Arthritis, psoriatic arthritis, graft-versus-host disease, non-infectious uveitis, Crohn's disease, ulcerative colitis, ankylosing spondylitis, autoimmune skin diseases and other autoimmune diseases.

Furthermore, the JAK mediated diseases may include, but are not limited to, psoriasis, atopic dermatitis, vitiligo, pruritus, scleroderma, alopecia areata, alopecia totalis, alopecia universalis, androgenetic alopecia and other autoimmune skin diseases.

Specifically, the lymphoma of the present disclosure may include but is not limited to Hodgkins disease or non-Hodgkins leukemia, and the non-Hodgkins lymphoma includes but is not limited to B-cell lymphoma or T-cell lymphoma.

The leukemia of the present disclosure includes but is not limited to acute lymphoblastic leukemia, chronic lymphocytic leukemia, acute myeloid leukemia, chronic myelocytic leukemia.

The myelodysplastic syndrome and myeloproliferative neoplasm of the present disclosure include, but are not limited to, myelofibrosis, primary myelofibrosis, post-essential thrombocythemia myelofibrosis, post-polycythemia vera myelofibrosis, essential thrombocythemia, polycythemia vera, multiple myeloma.

In addition to lymphoma and leukemia, the tumors of the present disclosure also include but are not limited to non-small cell lung cancer, small cell lung cancer, liver cancer, kidney cancer, prostate cancer, breast cancer, pancreatic cancer, gastric cancer, colon cancer, melanoma, head and neck cancer and other solid tumors.

The autoimmune diseases of the present disclosure include but are not limited to Rheumatoid Arthritis, Juvenile Idiopathic Arthritis, Juvenile Dermatomyositis, Atopic Dermatitis, Giant Cell Arteritis, Takayasu Arteritis, Kawasaki Disease, Herpes Zoster, Autoinflammatory Syndromes, Ankylosing Spondylitis, Aicardi-Goutieres Syndrome, Alopecia Areata, Alopecia Totalis, Alopecia Universalis, Androgenetic Alopecia, Behçet's Disease/Behçet's Syndrome, CANDLE syndrome (Chronic Atypical Neutrophilic Dermatosis With Lipodystrophy and Elevated Temperature), Graft-versus-host Disease, Diabetic Kidney Disease, Dry Eye Syndromes/Keratoconjunctivitis Sicca, Non-infectious Uveitis, Pruritus, Psoriasis, Plaque Psoriasis, Psoriatic Arthritis, Inflammatory Bowel Disease, Crohn's Disease, Small Bowel Crohn's Disease, Fistulizing Crohn's Disease, Ulcerative Colitis, SVAI (Stimulator of Interferon Genes (STING)-Associated Vasculopathy With Onset During Infancy), Systemic Lupus Erythematosus, Scleroderma (Systemic Sclerosis/Scleroderma), Vitiligo, Chronic Beryllium Disease, Palmoplantar Pustulosis, Multiple Sclerosis.

In particular, the use of the present disclosure refers to the use in preparation of a medicament for the treatment of diseases mediated by Tyk2 kinase.

The pyrazolopyrazine-derived compound and its pharmaceutical composition provided by the present disclosure have significant JAK kinase inhibitory activity and excellent pharmacokinetic properties, in particular, have high Tyk2 inhibitory activity and higher selectivity relative to JAK2. It can reduce the toxicity caused by JAK2 inhibition. It has great application potential.

In particular, the present disclosure relates to a method for treating a disease mediated by Janus Kinase (JAK), which includes a step of administering to a subject in need of such treatment an effective amount of the pyrazolopyrazine derived compound or its pharmaceutical composition provided by the present disclosure.

DETAILED DESCRIPTION

Unless otherwise defined, all scientific and technological terms herein have the same meanings as commonly understood by those skilled in the art. Unless otherwise specified, all patents, patent applications, and publications cited in the disclosure are incorporated herein by reference in their entirety. When a trade name appears, it refers to its corresponding commodity or its active ingredient.

It should be understood that the foregoing brief description and the following detailed description are exemplary and only for explanation, and do not impose any limitation on the subject matter of the disclosure. In this application, it must be noted that, unless clearly stated otherwise in the context, the singular form used in specification and claims includes the plural form of the thing referred to. It should also be noted that the use of "or" means "and/or" unless otherwise specified. In addition, the term "including" and other forms such as "comprising", and "containing" are not limiting.

Definitions of standard chemical terms may be found in the literature, including Carey and Sundberg's "Advanced Organic Chemistry $4^{th}$ Ed, Vol A (2000) and B (2001), Plenum Press, New York. Unless otherwise specified, conventional methods within the technical field are applied, such as mass spectrometry, NMR, HPLC, protein chemistry, biochemistry, recombinant DNA technology, and pharmacological methods. Unless specific definitions are provided, those skilled in the art know the related terms and laboratory operations and techniques in analytical chemistry, synthetic organic chemistry, and medical and pharmaceutical chemistry used in this disclosure. Standard techniques may be used for chemical synthesis, chemical analysis, drug preparation, formulation, drug delivery and patient treatment. Standard techniques may be used for recombinant DNA, oligonucleotide synthesis, and tissue culture and transformation (such as electroporation, lipid infection). For example, a kit with instructions provided by the manufacturer may be used, or the reaction and purification techniques may be carried out according to methods known in the art, or according to the method described in the present disclosure. Generally speaking, the aforementioned techniques and process may be implemented by conventional methods well-known in the art and described in various general documents or more specific documents. These documents are described and cited in the present disclosure.

When a substituent is described by a conventional chemical formula written from left to right, the substituent also includes chemically equivalent substituents obtained when the structural formula is written from right to left. For example, $CH_2O$ is equivalent to $OCH_2$.

The term "substituted" means that any one or more hydrogen atoms on a specific atom are replaced by a substituent, as long as the valence of the specific atom is normal and the compound after substitution is stable. When the substituent is oxo (ie =O), it means that two hydrogen atoms are replaced, and the oxo will not occur on the aromatic group.

When any variable (such as R) occurs more than once in the composition or structure of a compound, its definition in each case is independent. Thus, for example, if a group is substituted with 0-2 Rs, the group may optionally be substituted with up to two Rs, and R has independent options in each case. In addition, combinations of substituents and/or variants thereof are only permitted if such combinations result in stable compounds.

As used herein, $C_{m-n}$ refers to the part having m-n carbon atoms. For example, the "$C_{1-6}$" group means that the part has 1-6 carbon atoms, that is, the group contains 1 carbon atom, 2 carbon atoms, 3 carbon atoms . . . 6 carbon atoms. Therefore, for example, "$C_{1-6}$ alkyl" refers to an alkyl containing 1-6 carbon atoms, that is, the alkyl group is selected from methyl, ethyl, propyl, isopropyl, n-butyl, isopropyl, n-butyl, sec-butyl, tert-butyl . . . , etc. Numerical ranges in this text, for example "1-6" refers to each integer in the given range. For example, "1-6 carbon atoms" means that the group may have 1 carbon atom, 2 carbon atoms, 3 carbon atoms, 4 carbon atoms, 5 carbon atoms, or 6 carbon atoms.

The term "member" refers to the number of skeletal atoms constituting the ring. For example, pyridine is a six-membered ring and pyrrole is a five-membered ring.

The term "pharmaceutically acceptable" refers to those compounds, materials, compositions and/or dosage forms that are within the scope of reliable medical judgment and are suitable for use in contact with human and animal tissues without excessive toxicity, irritation, allergic reactions or other problems or complications of the disease, and are commensurate with a reasonable benefit/risk ratio.

The term "pharmaceutical composition" refers to a biologically active compound optionally mixed with at least one pharmaceutically acceptable chemical component or agent. The pharmaceutically acceptable chemical component or agent is the "carrier", which helps for introducing the compound into cells or tissues. It includes, but is not limited to, stabilizers, diluents, suspending agents, thickeners, and/or excipients.

The term "pharmaceutically acceptable salt" refers to a salt that retains the biological efficacy of the free acid and free base of the specified compound and has no adverse effects in biology or other aspects. Unless otherwise specified, the salts in the present disclosure may include metal salts, ammonium salts, salts formed with organic bases, salts formed with inorganic acids, salts formed with organic acids, salts formed with basic or acidic amino acids, etc. Non-limiting examples of metal salts include, but are not limited to, alkali metal salts, such as sodium salt, potassium salt, etc.; alkaline earth metal salts, such as calcium salt, magnesium salt, barium salt, etc.; aluminum salt, and the like. Non-limiting examples of salts formed with organic bases include, but are not limited to, the salts formed with trimethylamine, triethylamine, pyridine, picoline, 2,6-lutidine, ethanolamine, diethanolamine, triethanolamine, cyclohexylamine, dicyclohexylamine and the like. Non-limiting examples of salts formed with inorganic acids include, but are not limited to, salts formed with hydrochloric acid, hydrobromic acid, nitric acid, sulfuric acid, phosphoric acid, and the like. Non-limiting examples of salts formed with organic acids include, but are not limited to, salts formed with formic acid, acetic acid, trifluoroacetic acid, fumaric acid, oxalic acid, malic acid, maleic acid, tartaric acid, citric acid, succinic acid, methanesulfonic acid, benzene sulfonic acid, p-toluenesulfonic acid, etc. Non-limiting examples of salts formed with basic amino acids include, but are not limited to, salts formed with arginine, lysine, ornithine, and the like. Non-limiting examples of salts formed with acidic amino acids include, but are not limited to, salts formed with aspartic acid, glutamic acid, and the like.

Pharmaceutically acceptable salts may be synthesized from parent compounds containing acid radicals or bases by conventional chemical methods. Generally, such salts are prepared by reacting these compounds in free acid or base form with a stoichiometric amount of appropriate base or acid in water or organic solvent or a mixture of both. Generally, non-aqueous media such as ether, ethyl acetate, ethanol, isopropanol or acetonitrile are preferred.

The term "solvate" refers to a physical aggregate formed by a compound of the present disclosure and one or more solvent molecules. This physical aggregate includes varying degrees of ions and covalent bonds, such as hydrogen bonds. It has been shown that this solvate may be separated, for example, when one or more solvent molecules are mixed in the crystal lattice. "solvate" includes both solvent phase and separable solvate. There are many examples of corresponding solvates, including ethanol solvates, methanol solvates and the like. "Hydrate" is a solvate that uses water ($H_2O$) molecules as a solvent. One or more compounds in the present disclosure may be prepared as solvates at will. The preparation of solvates is well known. For example, M. Caira et al, J. Pharmaceutical Sci., 93(3), 601-611 (2004) describe the preparation of a solvate of the antifungal drug fluconazole, that is, preparation with ethyl acetate and water. E. C. van Tonder et al, AAPS PharmSciTech., 5(1), article 12 (2004); and A L Bingham et al, Chem. Commun., 603-604 (2001) also describes the similar methods for preparing solvates and hydrates. A typical, non-limiting preparation process is to dissolve the compound of the present disclosure in an ideal solvent (organic solvent or water or their mixed solvent) at a temperature higher than normal temperature, to cool down, and to leave to crystallize. Then the crystals are separated by use standard methods. The I. R. spectroscopy analysis technique may confirm the existence of the solvent (water) that forms the solvate (hydrate) in the crystal.

The term "active metabolite" refers to an active derivative of the compound formed when the compound is metabolized.

The term "polymorphs" refers to compounds of the present disclosure that exist in different crystal lattice forms.

The term "isotopically labelled compound" refers to an isotopically labeled compound of the present disclosure. For example, the isotopes in the compound of the present disclosure may include various isotopes of elements such as H, C, N, O, P, F, S, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}S$.

The term "stereoisomers" refers to isomers produced by different arrangements of atoms in the molecule in space. The compounds of the present disclosure contain structures such as asymmetric or chiral centers and double bonds. Therefore, the compounds of the present disclosure may include optical isomers, geometric isomers, tautomers, atropisomers and other isomers. These isomers and their single isomers, racemates, etc. are all included in the scope of the present disclosure. For example, for optical isomers, optically active (R)- and (S)-isomers and D and L isomers may be prepared by chiral resolution, chiral synthesis or chiral reagents or other conventional techniques. For example, it may be converted into diastereomers by reacting with appropriate optically active substances (such as chiral alcohols or Mosher's Mohsyl chloride), separated and converted (such as hydrolyzed) into the corresponding single isomer. For another example, it may also be separated by a chromatographic column.

The "pharmaceutical compositions" herein may be prepared in a manner well known in the pharmaceutical field, and they may be administered or applied by various routes, depending on whether local or systemic treatment is required and the area to be treated. It may be topically administered (for example, transdermal, skin, eye and mucous membranes including intranasal, vaginal and rectal delivery), pulmonarily administered (for example, by inhalation or insufflation of powder or aerosol, including through sprayers; intratracheal, intranasal), orally or parenterally administered. Parenteral administration includes intravenous, intraarterial, subcutaneous, intraperitoneal or intramuscular injection or infusion; or intracranial, such as intrathecal or intracerebroventricular administration. It may be administered parenterally in a single bolus dose, or it may be administered by, for example, a continuous infusion vacuum. The pharmaceutical composition herein includes but is not limited to the following forms: tablets, pills, powders, lozenges, sachets, cachets, elixirs, suspensions, emulsions, solutions, syrups, aerosols (solid or dissolved in a liquid vehicle); for example, ointments, soft and hard gelatin capsules, suppositories, sterile injection solutions and sterile packaged powders.

The pharmaceutical composition may be formulated in a unit dosage form, and each dosage may contain about 0.1 to 1000 mg, for example, about 5 to 1000 mg, or about 100 to 500 mg of active ingredient. The term "unit dosage form" refers to a physically separated single dosage unit suitable for use in human patients and other mammals, and each unit contains a predetermined amount of active substance that is calculated to produce the desired therapeutic effect mixed with a suitable pharmaceutical carrier.

EMBODIMENTS

To make the objectives, technical solutions, and advantages of the present disclosure clearer, the technical solutions of the exemplary embodiments of the present disclosure will be further described below.

In the present disclosure, the compounds described in the present disclosure may be prepared by the following methods. The following methods and examples are to illustrate these methods. These procedures and examples should not be construed as limiting the present disclosure in any way. The compounds described herein may also be synthesized using standard synthesis techniques known to those skilled in the art, or methods known in the art and methods described herein may be used in combination.

The chemical reactions in the embodiments of the present disclosure are completed in a suitable solvent, and the solvent must be suitable for the chemical changes of the present disclosure and the reagents and materials required. In order to obtain the compounds of the present disclosure, it is sometimes necessary for those skilled in the art to modify or select the synthesis steps or reaction schemes based on the existing embodiments.

An important consideration in the planning of any synthetic route in the art is to select an appropriate protecting group for the reactive functional group (such as the amino group in the present disclosure). For trained practitioners, Greene and Wuts (Protective Groups In Organic Synthesis, Wiley and Sons, 1991) is the authority in this regard. All references cited in the present disclosure are incorporated into the present disclosure in their entirety.

The reactions described herein may be monitored according to any suitable method known in the art. For example, product formation may be monitored by a broad spectrum method such as nuclear magnetic resonance spectroscopy (such as $^1H$ or $^{13}C$), infrared spectroscopy, spectrophotometry (such as UV-visible light), mass spectrometry, etc., or chromatography such as high performance liquid chromatography (HPLC) or thin layer chromatography.

Preparation of Intermediates

Preparation Example 1 4-chloro-6-(1-methyl-1H-pyrazol-4-yl)pyrazolo[1,5-a]pyrazine (Compound I1)

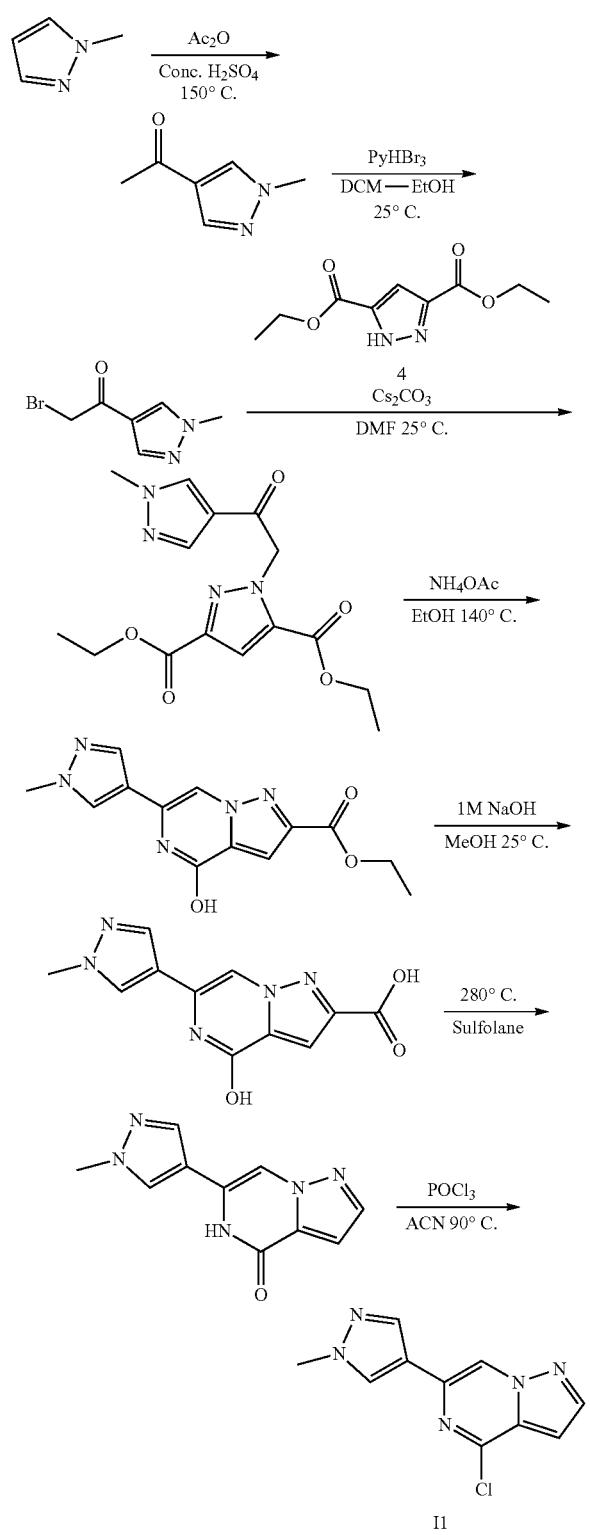

Step A: 1-(1-methyl-1H-pyrazol-4-yl)ethan-1-one

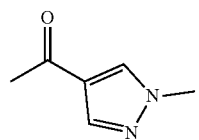

At about 20° C., concentrated $H_2SO_4$ (1.5 g, 16.5 mmol) was added to a mixture of 1-methylpyrazole (15.0 g, 183 mmol) and acetic anhydride (34.0 g, 333 mmol). The reaction mixture was heated at 150° C. for about 3 hours. After cooling at room temperature, pour it into ice water (0.5 L), adjust the pH to about 10 with 20% NaOH aqueous solution, and extract with DCM (4×200 mL). The combined DCM extract was dried over anhydrous sodium sulfate and concentrated to obtain the title compound as a brown oil (14.4 g, yield 63%).

$^1$H NMR (400 MHz, CDCl$_3$) δ 7.86 (s, 1H), 7.84 (s, 1H), 3.92 (s, 3H), 2.40 (s, 3H).

m/z=125[M+1]$^+$.

Step B: 2-bromo-1-(1-methyl-1H-pyrazol-4-yl)ethan-1-one

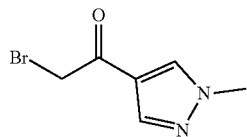

At about 15° C., to the solution of 1-(1-methyl-1H-pyrazol-4-yl)ethan-1-one (14.4 g, 116 mmol) in DCM (200 mL) and ethanol (50 mL) PyHBr$_3$ (37 g, 116 mmol) was added. The mixture was stirred at about 15° C. for about 18 hours. After the reaction was completed, water (200 mL) was added to stop the reaction. Then, the aqueous phase was extracted with DCM (4×200 mL). The combined DCM extracts were dried over anhydrous sodium sulfate and concentrated to remove most of the solvent. The residue was diluted with petroleum ether followed by being stirred at about 15° C. for about 30 minutes, and precipitate was formed. After filtration, the precipitate was dried to obtain a yellow solid of the title compound (21.5 g, yield 92%)

$^1$H NMR (400 MHz, CDCl$_3$) δ 7.97 (s, 1H), 7.91 (s, 1H), 4.17 (s, 2H), 3.93 (s, 3H).

m/z=203[M+1]$^+$.

Step C: diethyl 1-(2-(1-methyl-1H-pyrazol-4-yl)-2-oxo-ethyl)-1H-pyrazole-3,5-dicarboxylate

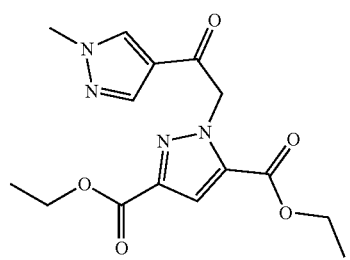 [SMILES: CCOC(=O)c1cc(C(=O)OCC)n(CC(=O)c2cnn(C)c2)n1]

At about 20° C., to a mixture of 2-bromo-1-(1-methyl-1H-pyrazol-4-yl)ethan-1-one (21.5 g, 106 mmol) and diethyl 1H-pyrazole-3,5-dicarboxylate (25.1 g, 118 mmol) in DMF (200 mL) was added $Cs_2CO_3$ (46 g, 140 mmol). After reacting for 18 hours at about 20° C., it was diluted with water (200 mL) and extracted with DCM (3×200 mL). The combined DCM extract was dried over anhydrous sodium sulfate and concentrated. The residue was purified by chromatography to obtain the title compound as a yellow solid (31.1 g, yield 93%).

$^1$H NMR (400 MHz, $CDCl_3$) δ 7.96 (s, 2H), 7.46 (s, 1H), 5.86 (s, 2H), 4.45 (q, 2H), 4.32 (q, 2H), 3.99 (s, 3H), 1.44 (t, 3H), 1.36 (t, 3H).

m/z=335[M+1]$^+$.

Step D: ethyl 4-hydroxy-6-(1-methyl-1H-pyrazol-4-yl)pyrazolo[1,5-a]pyrazine-2-carboxylate

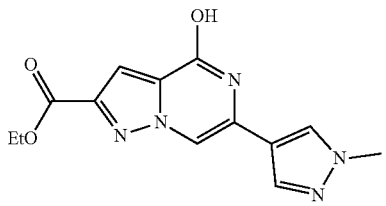 [SMILES: CCOC(=O)c1cc2c(O)nc(-c3cnn(C)c3)cn2n1]

At about 20° C., to a solution of diethyl 1-(2-(1-methyl-1H-pyrazol-4-yl)-2-oxo-ethyl)-1H-pyrazole-3,5-dicarboxylate (31.1 g, 93 mmol) in ethanol (300 mL) was added $NH_4OAc$ (35.8 g, 465 mmol). The mixture was heated in an autoclave at about 140° C. for about 15 hours. The reaction mixture was cooled to about 50° C., combined and filtered. The precipitate was dried to obtain an off-white solid of the title compound (26.7 g, yield 100%).

$^1$H NMR (400 MHz, DMSO-$d_6$) δ 11.35 (brs, 1H), 8.31 (s, 1H), 8.20 (s, 1H), 8.05 (s, 1H), 7.38 (s, 1H), 4.34 (q, 2H), 3.89 (s, 3H), 1.33 (t, 3H).

m/z=288[M+1]$^+$.

Step E: 4-hydroxy-6-(1-methyl-1H-pyrazol-4-yl)pyrazolo[1,5-a]pyrazine-2-carboxylic Acid

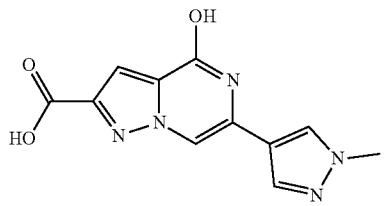 [SMILES: Cn1cc(-c2cn3nc(C(=O)O)cc3c(O)n2)cn1]

At about 20° C., to a suspension of ethyl 4-hydroxy-6-(1-methyl-1H-pyrazol-4-yl)pyrazolo[1,5-a]pyrazine-2-carboxylate (26.7 g, 93 mmol) in MeOH (300 mL) was added 1 M NaOH aqueous solution (280 mL). After about 30 minutes, the suspension became a clear solution. After stirring at about 20° C. for about 4 hours, the clear solution became a suspension, and a large amount of white solid precipitated out. The stirring was continued for 14 hours. The reaction mixture was then adjusted to about pH=2 with 12 M HCl aqueous solution, and concentrated to remove most of the MeOH. The residue was filtered and the precipitate was dried to obtain an off-white solid of the title compound (22.5 g, yield 93%).

$^1$H NMR (400 MHz, DMSO-$d_6$) δ 13.25 (brs, 1H), 11.67 (s, 1H), 8.34 (s, 1H), 8.16 (s, 1H), 8.06 (s, 1H), 7.32 (s, 1H), 3.88 (s, 3H).

m/z=260[M+1]$^+$.

Step F: 6-(1-methyl-1H-pyrazol-4-yl)pyrazolo[1,5-a]pyrazin-4-ol

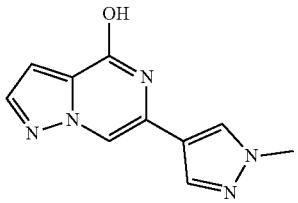

A mixture of 4-hydroxy-6-(1-methyl-1H-pyrazol-4-yl)pyrazolo[1,5-a]pyrazine-2-carboxylic acid (11.5 g, 44.4 mmol) in sulfolane (80 mL) was stirred at about 280° C. for about 2 hours, cooled to about 25° C., and stirred for about 1 hour. The mixture was directly purified by chromatography, eluting with petroleum ether-EtOAc (10:1 to 0:1) to remove the solvent sulfolane, followed by DCM-MeOH (10:1) to afford the title compound as a yellow solid (7.5 g, Yield 79%).

$^1$H NMR (400 MHz, DMSO-$d_6$) δ 11.45 (s, 1H), 8.28 (s, 1H), 8.10 (s, 1H), 8.04 (s, 1H), 7.88 (s, 1H), 6.99 (s, 1H), 3.88 (s, 3H).

m/z=216[M+1]$^+$.

Step G: 4-chloro-6-(1-methyl-1H-pyrazol-4-yl)pyrazolo[1,5-a]pyrazine (Compound I1)

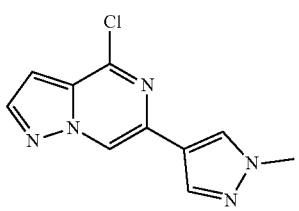 [SMILES: Cn1cc(-c2cn3nccc3c(O)n2)cn1]

At about 25° C., to a suspension of 6-(1-methyl-1H-pyrazol-4-yl)pyrazolo[1,5-a]pyrazin-4-ol (7.3 g, 33.9 mmol) in MeCN (150 mL) was added $POCl_3$ (28 mL, 305 mmol). The mixture was heated at about 90° C. for about 16 hours. Most of the $POCl_3$ was removed under vacuum, the remaining $POCl_3$ was neutralized with saturated aqueous $Na_2CO_3$, and extracted with DCM (3×200 mL). The combined DCM was dried over anhydrous sodium sulfate, filtered, concentrated, and purified by column chromatography to afford 4-chloro-6-(1-methyl-1H-pyrazol-4-yl)pyrazolo[1,5-a]pyrazine (Compound I1) (6.0 g, yield 76%).

$^1$H NMR (400 MHz, $CDCl_3$) δ 8.51 (d, J=0.8 Hz, 1H), 8.05 (d, J=2.3 Hz, 1H), 7.95 (s, 1H), 7.92 (s, 1H), 6.89 (dd, J=2.3, 0.8 Hz, 1H), 4.01 (s, 3H).

m/z=234[M+1]$^+$.

Preparation Example 2 4-chloro-6-(1-methyl-1H-pyrazol-4-yl)pyrazolo[1,5-a]pyrazine-3-carbonitrile (Compound I2)

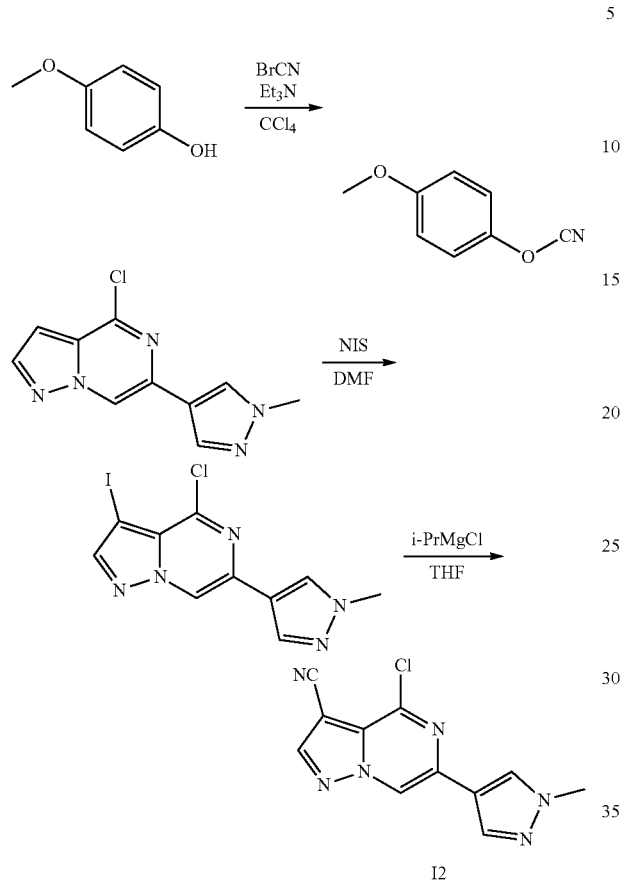

Step A: p-Methoxyphenol Cyanoester

At 0° C., to a solution of p-methoxyphenol (10.0 g, 80.6 mmol) and cyanogen bromide (8.5 g, 80.6 mmol) in carbon tetrachloride (100 mL) was slowly added triethylamine (12 mL, 85 mmol) dropwise. During the dripping process, keep the temperature of the reaction system no more than 10° C. Continue to stir at 0° C. for 30 minutes, add water to quench the reaction after the completion of the reaction monitored by TLC. The reaction solution was extracted with DCM, and the combined organic phase was washed once with water, and once with brine, dried over anhydrous sodium sulfate, filtered, concentrated under reduced pressure in vacuo, and purified by column chromatography to afford the title compound as a white foam solid (9.7 g, yield 81%).

¹H NMR (400 MHz, CDCl₃) δ 7.24-7.18 (m, 2H), 6.96-6.89 (m, 2H), 3.81 (s, 3H).

m/z=150[M+1]⁺.

Step B: 4-chloro-3-iodo-6-(1-methyl-1H-pyrazol-4-yl)pyrazolo[1,5-a]pyrazine

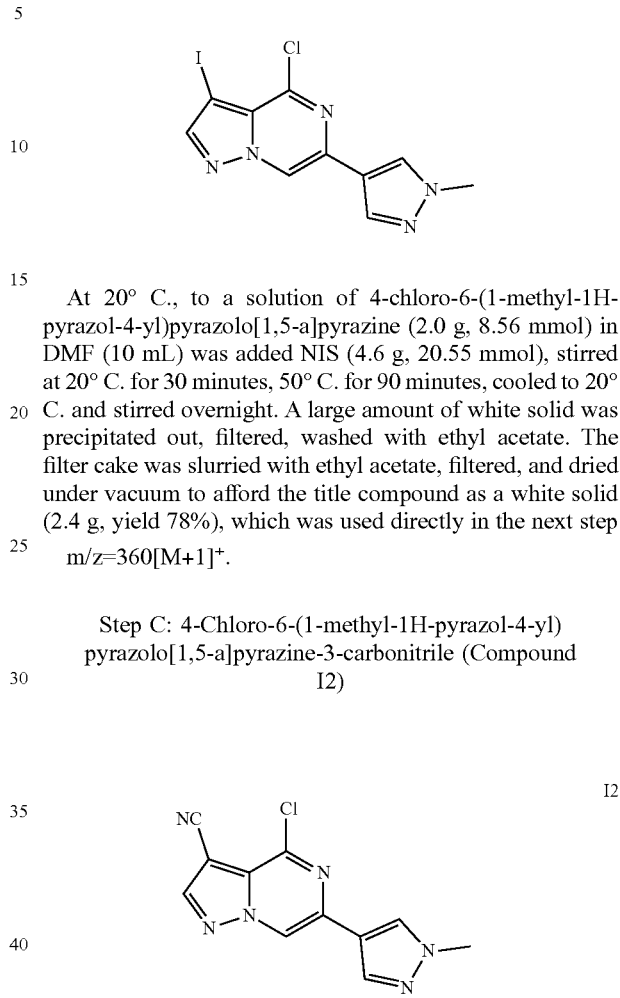

At 20° C., to a solution of 4-chloro-6-(1-methyl-1H-pyrazol-4-yl)pyrazolo[1,5-a]pyrazine (2.0 g, 8.56 mmol) in DMF (10 mL) was added NIS (4.6 g, 20.55 mmol), stirred at 20° C. for 30 minutes, 50° C. for 90 minutes, cooled to 20° C. and stirred overnight. A large amount of white solid was precipitated out, filtered, washed with ethyl acetate. The filter cake was slurried with ethyl acetate, filtered, and dried under vacuum to afford the title compound as a white solid (2.4 g, yield 78%), which was used directly in the next step m/z=360[M+1]⁺.

Step C: 4-Chloro-6-(1-methyl-1H-pyrazol-4-yl)pyrazolo[1,5-a]pyrazine-3-carbonitrile (Compound I2)

Under N₂ protection, to a solution of 4-chloro-3-iodo-6-(1-methyl-1H-pyrazol-4-yl)pyrazolo[1,5-a]pyrazine (2.4 g, 6.7 mmol) in THF (20 mL) was slowly add i-PrMgCl (2 M in THF, 3.7 mL, 7.34 mmol) dropwise. During the addition, keep the temperature of the reaction system below −20° C. and continue stirring at this temperature for 30 minutes. Then, p-methoxyphenol cyanoester (1.2 g, 8.0 mmol) was slowly added to the reaction system with the temperature of below −20° C. kept, and then the reaction system was raised to 25° C. for 5 hours. After the completion of the reaction monitored by TLC, the reaction was quenched by adding saturated ammonium chloride aqueous solution and then extracted with ethyl acetate. The combined organic phase was washed once with water and once with saturated brine, dried over anhydrous sodium sulfate, filtered, concentrated under reduced pressure in vacuo, and purified by column chromatography to afford 4-chloro-6-(1-methyl-1H-pyrazol-4-yl)pyrazolo[1,5-a]pyrazine-3-carbonitrile (compound I2) (1.2 g, yield 67%).

¹H NMR (400 MHz, DMSO-d₆) δ 9.41 (s, 1H), 8.84 (s, 1H), 8.32 (s, 1H), 8.07 (s, 1H), 3.89 (s, 3H).

m/z=259[M+1]⁺.

Preparation Example 3 3-(3-amino-4-(4,4,5,5-tetramethyl-1,3,2-dioxaborolan-2-yl)-1H-pyrazole-1-yl)-3-(cyanomethyl)azetidine-1-carboxylic Acid Tert-Butyl Ester (Compound I3)

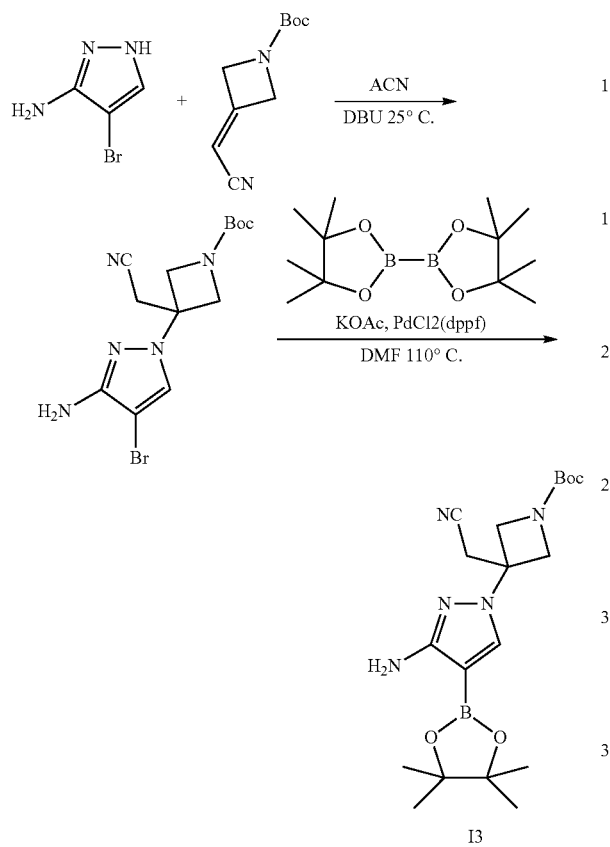

Step A: 3-(3-amino-4-bromo-1H-pyrazol-1-yl)-3-(cyanomethyl)azetidine-1-carboxylic Acid Tert-Butyl Ester At 25° C., to a solution of 3-(cyanomethylene)azetidine-1-carboxylic acid tert-butyl ester (5.3 g, 27.3 mmol) in MeCN (60 mL) was added 3-amino-4-bromo-1H-pyrazole (4.0 g, 24.8 mmol) and DBU (5.7 g, 37.2 mmol). After stirring at 25° C. for 18 hours, the mixture was concentrated. The residue was diluted with ethyl acetate, washed twice with water, dried over anhydrous sodium sulfate, filtered, concentrated in vacuo, and purified by column chromatography to afford the title compound as a white solid (8.7 g, yield 98%).

$^1$H NMR (400 MHz, CDCl$_3$) δ 7.41 (s, 1H), 4.31 (d, J=9.6 Hz, 2H), 4.11 (d, J=9.7 Hz, 2H), 3.83 (s, 2H), 3.13 (s, 2H), 1.45 (s, 9H). m/z=356[M+1]$^+$.

Step B: 3-(3-amino-4-(4,4,5,5-tetramethyl-1,3,2-dioxaborolan-2-yl)-1H-pyrazole-1-yl)-3-(cyanomethyl)azetidine-1-carboxylic Acid Tert-Butyl Ester (Compound I3)

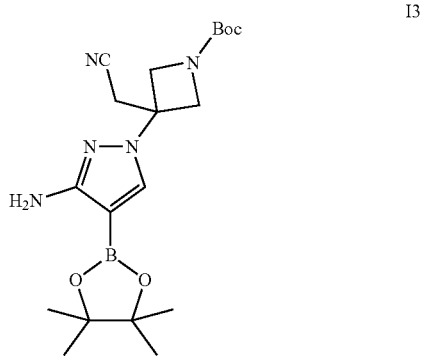 [SMILES: CC(C)(C)OC(=O)N1CC(CC#N)(n2cc(B3OC(C)(C)C(C)(C)O3)c(N)n2)C1]

At 25° C., to a solution of 3-(3-amino-4-bromo-1H-pyrazol-1-yl)-3-(cyanomethyl)azetidine-1-carboxylic acid tert-butyl ester (4.7 g, 13.2 mmol) in DMF (100 mL) was added pinacol diborate (10.0 g, 39.3 mmol) and anhydrous potassium acetate (5.2 g, 52.4 mmol). The mixture was bubbling with nitrogen for 3 minutes, and [1,1'-bis(diphenylphosphino)ferrocene]palladium dichloride (480 mg, 0.7 mmol) was added thereto. Then, the mixture was bubbling with nitrogen for 3 minutes and protected by a nitrogen balloon at 110° C. After reacting for 2 hours, the reaction was completed by TLC monitoring. The reaction was quenched by adding water to the reaction mixture, extracted with ethyl acetate, and the organic phases were combined, washed twice with water and once with saturated brine, dried over anhydrous sodium sulfate, filtered, and concentrate under reduced pressure in vacuo, purify by column chromatography to afford 3-(3-amino-4-(4,4,5,5-tetramethyl-1,3,2-dioxaborolan-2-yl)-1H-pyrazol-1-yl)-3-(cyanomethyl)azetidine-1-carboxylic acid tert-butyl ester (Compound I3) (750 mg, yield 14%).

$^1$H NMR (400 MHz, CDCl$_3$) δ 7.60 (s, 1H), 4.32 (m, 4H), 4.11 (d, J=9.5 Hz, 2H), 3.17 (s, 2H), 1.44 (s, 9H), 1.30 (s, 12H).

m/z=404[M+1]$^+$.

Preparation Example 4 2-(3-(3-amino-4-(4,4,5,5-tetramethyl-1,3,2-dioxaborolan-2-yl)-1H-pyrazol-1-yl)-1-(ethylsulfonyl)azetidin-3-yl)acetonitrile (Compound I4)

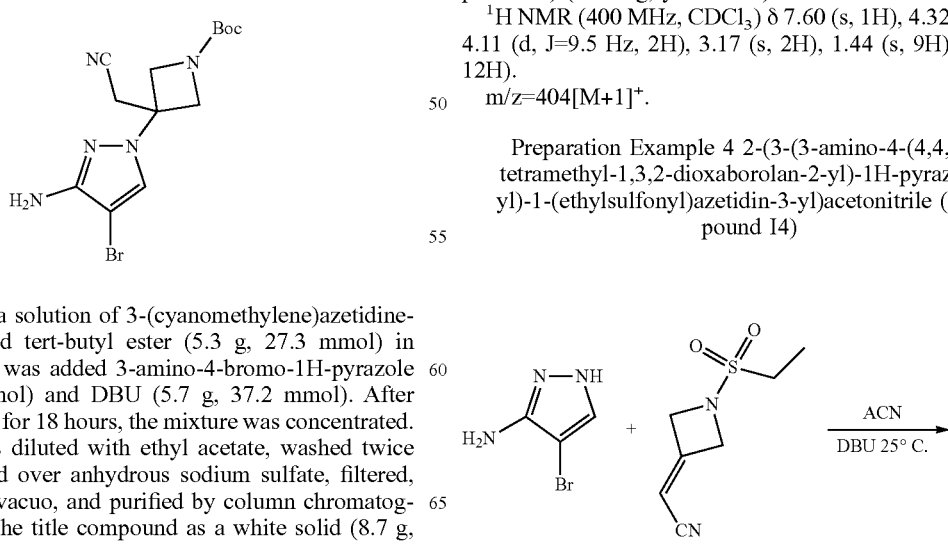

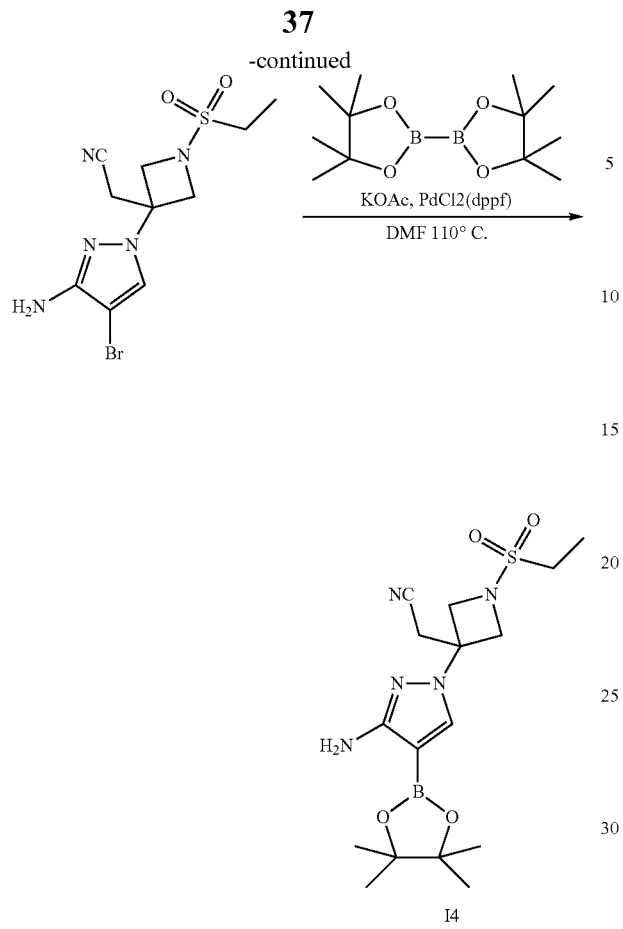

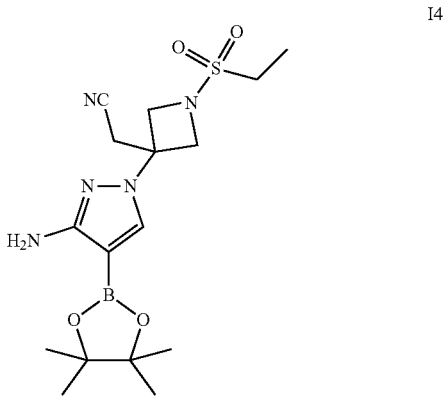

Step B: 2-(3-(3-Amino-4-(4,4,5,5-tetramethyl-1,3,2-dioxaborolan-2-yl)-1H-pyrazol-1-yl)-1-(ethylsulfonyl)azetidin-3-yl)acetonitrile (Compound I4)

I4

Step A: 2-(3-(3-amino-4-bromo-1H-pyrazol-1-yl)-1-(ethylsulfonyl)azetidin-3-yl)acetonitrile

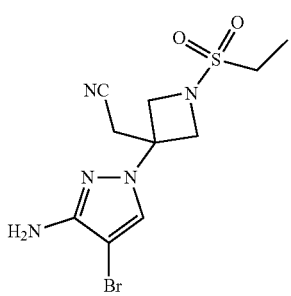 [SMILES: CCS(=O)(=O)N1CC(CC#N)(n2cc(Br)c(N)n2)C1]

At 25° C., to a solution of 3-(1-(ethylsulfonyl)azetidine-3-ylidene)acetonitrile (1.3 g, 6.8 mmol) in MeCN (20 mL) was added amino-4-bromo-1H-pyrazole (1.0 g, 6.2 mmol) and DBU (1.4 g, 9.3 mmol). After stirring for 18 hours at 25° C., the mixture was concentrated. The residue was diluted with ethyl acetate, washed twice with water, dried over anhydrous sodium sulfate, filtered, concentrated in vacuo, and purified by column chromatography to afford the title compound as a white solid (1.9 g, The yield is 88%).

$^1$H NMR (400 MHz, CDCl$_3$) δ 7.42 (s, 1H), 4.40 (d, J=9.3 Hz, 2H), 4.06 (d, J=9.4 Hz, 2H), 3.86 (s, 2H), 3.22 (s, 2H), 3.03 (q, J=7.4 Hz, 2H), 1.38 (t, J=7.4 Hz, 3H). m/z=348 [M+1]$^+$.

At 25° C., to a solution of 2-(3-(3-amino-4-bromo-1H-pyrazol-1-yl)-1-(ethylsulfonyl)azetidin-3-yl)acetonitrile (1.9 g, 5.5 mmol) in DMF (30 mL) was added pinacol diborate (4.2 g, 16.4 mmol) and anhydrous potassium acetate (2.2 g, 21.9 mmol) and bubbling the mixture with nitrogen for 3 minutes. To the mixture was added [1,1'-bis(diphenylphosphino)ferrocene]palladium dichloride (200 mg, 0.3 mmol), and then bubbling with nitrogen for 3 minutes, protected by a nitrogen ball. The reaction was carried out at 110° C. for 2 hours, and was completed by TLC monitoring. The reaction was quenched by adding water to the reaction mixture, extracted with ethyl acetate. The combined organic phases were washed twice with water, once with saturated brine, dried over anhydrous sodium sulfate, filtered, concentrated under reduced pressure and purified by column chromatography to afford 2-(3-(3-amino-4-(4,4,5,5-tetramethyl-1,3,2-dioxaborolane-2-yl)-1H-pyrazol-1-yl)-1-(ethylsulfonyl)azetidin-3-yl)acetonitrile (Compound I4) (320 mg, yield 15%).

$^1$H NMR (400 MHz, CDCl$_3$) δ 7.64 (s, 1H), 4.47 (d, J=8.9 Hz, 2H), 4.37 (s, 2H), 4.11 (d, J=9.0 Hz, 2H), 3.29 (s, 2H), 3.08 (q, J=7.3 Hz, 2H), 1.43 (t, J=7.4 Hz, 3H), 1.35 (s, 12H). m/z=396[M+1]$^+$.

Preparation Example 5 2-(3-(3-amino-4-(4,4,5,5-tetramethyl-1,3,2-dioxaborolan-2-yl)-1H-pyrazol-1-yl)-1-(isopropylsulfonyl)azetidin-3-yl)acetonitrile (Compound I5)

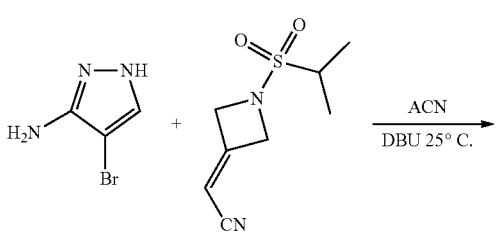

-continued

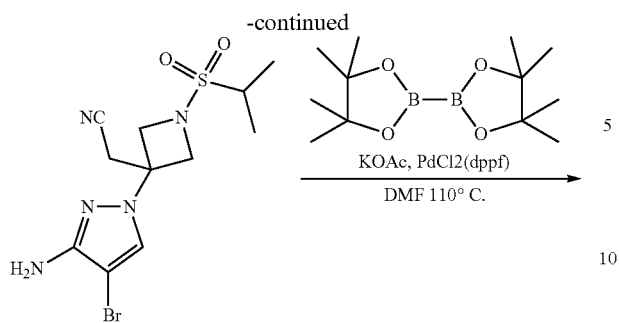

Step A: 2-(3-(3-amino-4-bromo-1H-pyrazol-1-yl)-1-(isopropylsulfonyl)azetidin-3-yl)acetonitrile

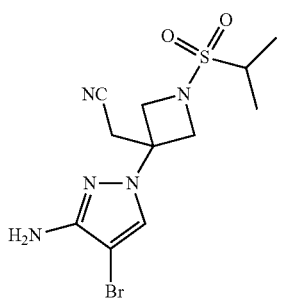 [SMILES: CC(C)S(=O)(=O)N1CC(CC#N)(n2cc(Br)c(N)n2)C1]

At 25° C., to a solution of 2-(1-(isopropylsulfonyl)azetidine-3-ylidene)acetonitrile (6.8 g, 34 mmol) in MeCN (100 mL) was added 3-amino-4-bromo-1H-pyrazole (5.0 g, 30.9 mmol) and DBU (7.1 g, 46.3 mmol). After stirring at 25° C. for 18 hours, the mixture was concentrated. The residue was diluted with ethyl acetate, washed twice with water, dried over anhydrous sodium sulfate, filtered, concentrated in vacuo, and purified by column chromatography to afford the title compound as a white solid (8.0 g, yield 71%).

$^1$H NMR (400 MHz, CDCl$_3$) δ 7.42 (s, 1H), 4.43 (d, J=9.4 Hz, 2H), 4.05 (d, J=9.5 Hz, 2H), 3.85 (s, 2H), 3.21 (s, 2H), 3.20-3.12 (m, 1H), 1.37 (d, J=6.8 Hz, 6H).

m/z=362[M+1]$^+$.

Step B: 2-(3-(3-amino-4-(4,4,5,5-tetramethyl-1,3,2-dioxaborolan-2-yl)-1H-pyrazol-1-yl)-1-(isopropylsulfonyl)azetidin-3-yl)acetonitrile (Compound I5)

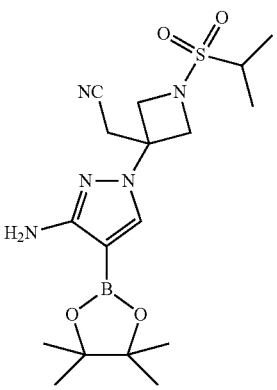

At 25° C., to a solution of 2-(3-(3-amino-4-bromo-1H-pyrazol-1-yl)-1-(isopropylsulfonyl)azetidin-3-yl)acetonitrile (8.0 g, 22.1 mmol) in DMF (120 mL) was added pinacol diborate (16.9 g, 66.3 mmol) and anhydrous potassium acetate (8.7 g, 88.4 mmol), and bubbling the mixture with nitrogen for 3 minutes. To the mixture was added [1,1'-bis(diphenylphosphino)ferrocene]palladium dichloride (812 mg, 1.1 mmol), and was bubbling with nitrogen for 3 minutes. The reaction was kept at 110° C. for 2 hours with the protection of nitrogen balloon. After the completion monitored by TLC, the reaction was quenched by adding water to the reaction mixture. The mixture was then extracted with ethyl acetate. The combined organic phases were washed twice with water, once with saturated brine, dried over anhydrous sodium sulfate, filtered, concentrated in vacuo, and purified by column chromatography to afford 2-(3-(3-amino-4-(4,4,5,5-tetramethyl-1,3,2-dioxaborolane)-2-yl)-1H-pyrazol-1-yl)-1-(isopropylsulfonyl)azetidin-3-yl)acetonitrile (compound I5) (1.74 g, yield 19%).

$^1$H NMR (400 MHz, CDCl$_3$) δ 7.59 (s, 1H), 4.44 (s, 2H), 4.32 (s, 2H), 4.05 (d, J=9.2 Hz, 2H), 3.24 (s, 2H), 3.15 (dt, J=13.7, 6.8 Hz, 1H), 1.36 (d, J=6.8 Hz, 6H), 1.30 (s, 12H). m/z=410[M+1]$^+$.

Preparation Example 6 2-(1-(3-amino-4-(4,4,5,5-tetramethyl-1,3,2-dioxaborolan-2-yl)-1H-pyrazol-1-yl)-3-(benzyloxy)cyclobutyl)acetonitrile (compound I6, Cis and Trans)

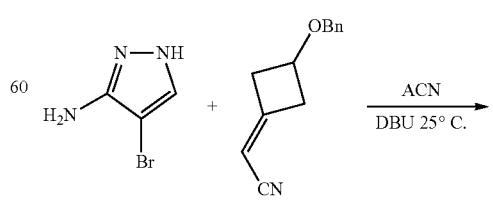

-continued

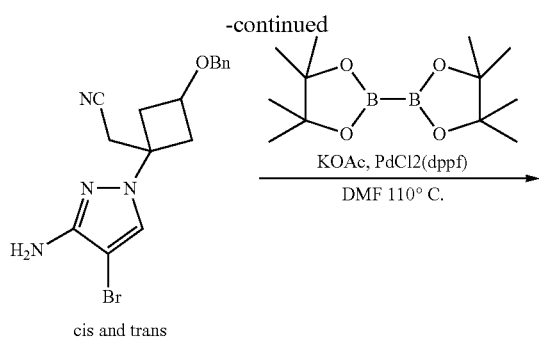

cis and trans

Step A: 2-(1-(3-amino-4-bromo-1H-pyrazol-1-yl)-3-(benzyloxy)cyclobutyl)acetonitrile (Cis and Trans)

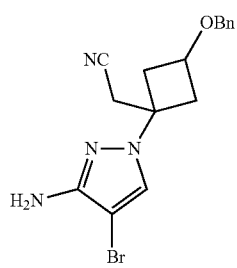 [SMILES: N#CCC1(n2cc(Br)c(N)n2)CC(OCc2ccccc2)C1]

cis and trans

At 25° C., to a solution of 2-(3-(benzyloxy)cyclobutylidene)acetonitrile (4.0 g, 20.1 mmol) in MeCN (30 mL) was added 3-amino-4-bromo-1H-pyrazole (3.6 g, 22.2 mmol) and DBU (4.6 g, 30.2 mmol). After stirring for 18 hours at 25° C., the mixture was concentrated, and the residue was diluted with ethyl acetate, washed twice with water, dried over anhydrous sodium sulfate, filtered, concentrated in vacuo, and purified by column chromatography to afford the title compound as a white solid (4.6 g, yield 56%).

m/z=361[M+1]$^+$.

Step B: 2-(1-(3-amino-4-(4,4,5,5-tetramethyl-1,3,2-dioxaborolan-2-yl)-1H-pyrazol-1-yl)-3-(benzyloxy)cyclobutyl)acetonitrile (compound I6, Cis and Trans)

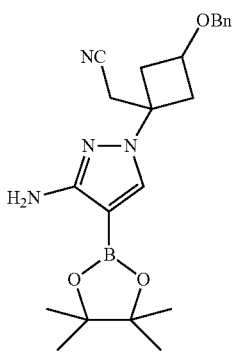

I6

At 25° C., to a solution of 2-(1-(3-amino-4-bromo-1H-pyrazol-1-yl)-3-(benzyloxy)cyclobutyl)acetonitrile (cis and trans)(4.6 g, 12.7 mmol) in DMF (80 mL) was added pinacol diborate (9.7 g, 38.1 mmol) and anhydrous potassium acetate (5.0 g, 50.8 mmol). The mixture was bubbling with nitrogen for 3 minutes, and [1,1'-bis(diphenylphosphino)ferrocene]palladium dichloride (512 mg, 0.7 mmol) was added thereto. The mixture was bubbling with nitrogen for 3 minutes and protected by a nitrogen balloon at 110° C. After reacting for 2 hours, TLC monitored the completion of the reaction. The reaction mixture was quenched by adding water and then extracted with ethyl acetate. The combined organic phases were washed twice with water, once with saturated brine, dried over anhydrous sodium sulfate, filtered, concentrated by reduced pressure in vacuo and purify by column chromatography to afford 2-(1-(3-amino-4-(4,4,5,5-tetramethyl-1,3,2-dioxaborolan-2-Yl)-1H-pyrazol-1-yl)-3-(benzyloxy)cyclobutyl)acetonitrile (compound I6, cis and trans) (412 mg, yield 8%).

m/z=409[M+1]$^+$.

Preparation Example 7 (1r,3r)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile (compound I7) and (1s,3s)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile (compound I8)

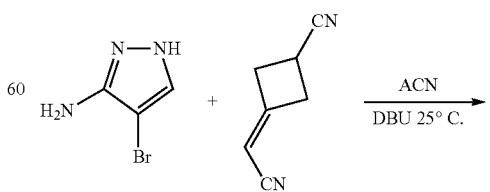

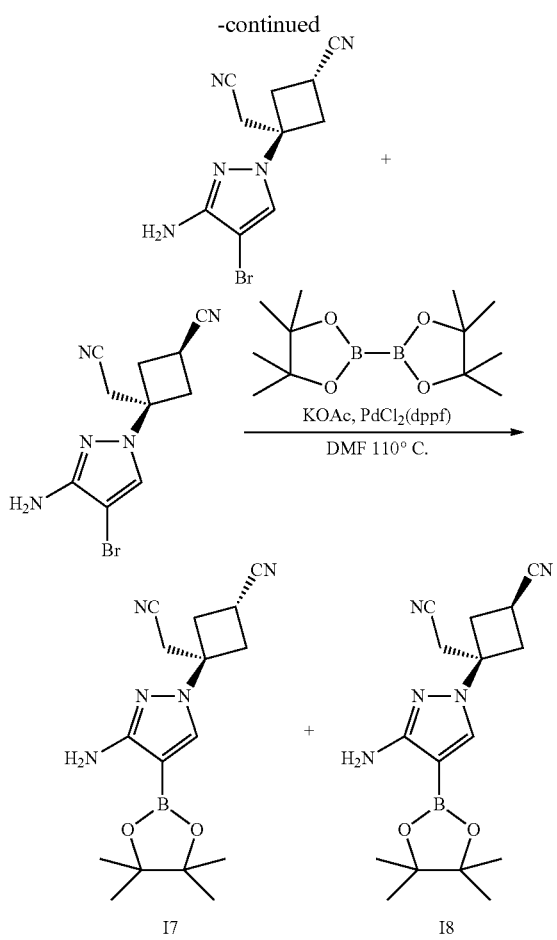

Step A: (1r,3r)-3-(3-amino-4-bromo-1H-pyrazol-1-yl)-3-(cyanomethyl)cyclobutyl-1-carbonitrile and (1s,3s)-3-(3-amino-4-bromo-1H-pyrazol-1-yl)-3-(cyanomethyl)cyclobutyl-1-carbonitrile

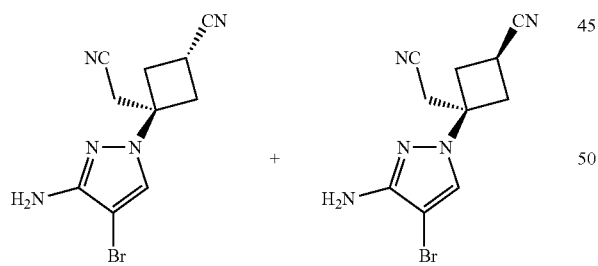

At 25° C., to a solution of 3-(cyanomethylene)cyclobutyl-1-carbonitrile (5.0 g, 42.3 mmol) in MeCN (60 mL) was added 3-amino-4-bromo-1H-pyrazole (7.9 g, 48.7 mmol) and DBU (9.7 g, 63.5 mmol). After stirring at 50° C. for 18 hours, the mixture was concentrated. The residue was diluted with ethyl acetate, washed twice with water, dried over anhydrous sodium sulfate, filtered, concentrated in vacuo, and purified by a chromatographic column to afford (1r,3r)-3-(3-amino-4-bromo-1H-pyrazol-1-yl)-3-(cyanomethyl)cyclobutyl-1-carbonitrile (6.1 g, yield 51%) and (1s,3s)-3-(3-amino-4-bromo-1H-pyrazol-1-yl)-3-(cyanomethyl)cyclobutyl-1-carbonitrile (4.1 g, yield 34%).

(1r,3r)-3-(3-amino-4-bromo-1H-pyrazol-1-yl)-3-(cyanomethyl)cyclobutyl-1-carbonitrile $^1$H NMR (400 MHz, CDCl$_3$) δ 7.44 (s, 1H), 4.03-3.70 (m, 2H), 3.31-3.25 (m, 1H), 3.21-3.12 (m, 2H), 3.10 (s, 2H), 2.88-2.75 (m, 2H).

(1s,3s)-3-(3-amino-4-bromo-1H-pyrazol-1-yl)-3-(cyanomethyl)cyclobutyl-1-carbonitrile $^1$H NMR (400 MHz, CDCl$_3$) δ 7.41 (s, 1H), 3.88 (s, 2H), 3.30-3.21 (m, 1H), 3.12-3.07 (m, 2H), 3.01 (s, 2H), 2.97-2.87 (m, 2H). m/z=281[M+1]$^+$.

Step B: (1r,3r)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile (compound I7) and (1s,3s)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile (compound I8)

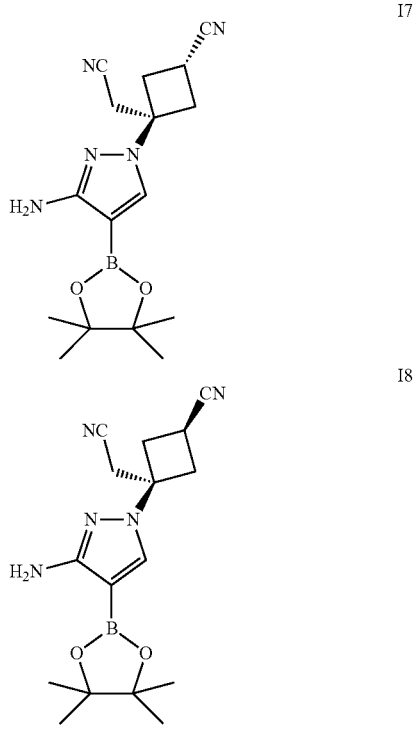

At 25° C., to a solution of (1r,3r)-3-(3-amino-4-bromo-1H-pyrazol-1-yl)-3-(cyanomethyl)cyclobutyl-1-carbonitrile (6.1 g, 21.7 mmol) in DMF (80 mL) was added pinacol diborate (14.1 g, 55.7 mmol) and anhydrous potassium acetate (7.3 g, 74.2 mmol). The mixture was bubbling with nitrogen for 3 minutes, and [1,1'-bis(diphenylphosphino)ferrocene]palladium dichloride (680 mg, 0.9 mmol) was added thereto. The mixture was bubbling with nitrogen for 3 minutes and protected by a nitrogen balloon at 110° C. After reacting for 2 hours, TLC monitored the completion of the reaction. The reaction mixture was quenched by adding water and then extracted with ethyl acetate. The combined organic phases were washed twice with water, once with saturated brine, dried over anhydrous sodium sulfate, filtered, concentrated by reduced pressure in vacuo and purify by column chromatography to afford (1r,3r)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile (compound I7) (1.4 g, yield 20%).

$^1$H NMR (400 MHz, CDCl$_3$) δ 7.59 (s, 1H), 4.32 (s, 2H), 3.26-3.16 (m, 1H), 3.15-3.05 (m, 4H), 2.77 (m, 2H), 1.30 (s, 12H).

m/z=328[M+1]$^+$.

Using (1s,3s)-3-(3-amino-4-bromo-1H-pyrazol-1-yl)-3-(cyanomethyl)cyclobutyl-1-carbonitrile (4.1 g, 14.6 mmol) to replace (1r,3r)-3-(3-amino-4-bromo-1H-pyrazol-1-yl)-3-(cyanomethyl)cyclobutyl-1-carbonitrile, the same process as above was operated to afford (1s,3s)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile (compound I8) (450 mg, yield 9%).

$^1$H NMR (400 MHz, CDCl$_3$) δ 7.59 (s, 1H), 4.36 (s, 2H), 3.30-3.21 (m, 1H), 3.13-3.07 (m, 2H), 3.04 (s, 2H), 2.99-2.86 (m, 2H), 1.35 (s, 12H).

m/z=328[M+1]$^+$.

Preparation Example 8 (1r,3r)-3-(3-bromo-1H-pyrrolo[3,2-c]pyridin-1-yl)-3-(cyanomethyl)cyclobutyl-1-carbonitrile (Compound I9) and (1s,3s)-3-(3-bromo-1H-pyrrolo[3,2-c]pyridin-1-yl)-3-(cyanomethyl)cyclobutyl-1-carbonitrile (Compound I10)

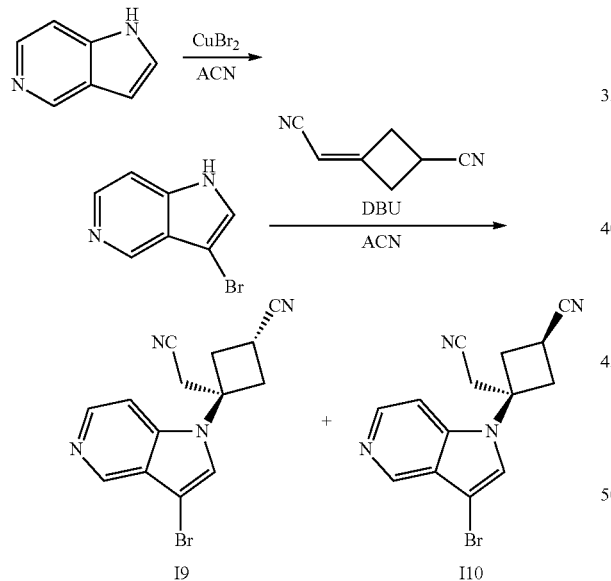

Step A: 3-bromo-1H-pyrrolo[3,2-c]pyridine

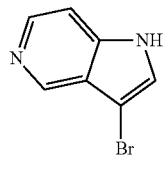

To a solution of 5-azaindole (11.8 g, 0.1 mol) in MeCN (100 mL) was added cuprous bromide (67.0 g, 0.3 mol) at 0° C. The green reaction mixture was warmed to room temperature, and stirred until the raw materials disappeared. The temperature of the reaction mixture was reduced to 0° C. with an ice bath, and a solution of ammonia in methanol (7N) was slowly added dropwise to the mixture to quench the reaction. The mixture was raised to room temperature and stirred for 0.5 hours, diluted with water and extracted with ethyl acetate (×3). The organic phases were combined and washed with saturated brine (×1), dried over anhydrous sodium sulfate, filtered, concentrated in vacuo, and purified by column chromatography to afford the title compound (10.0 g, yield 51%).

$^1$H NMR (400 MHz, DMSO-d$_6$) δ 11.90 (s, 1H), 8.78-8.33 (m, 2H), 7.69 (s, 1H), 7.47 (s, 1H).

m/z=197[M+1]$^+$.

Step B: (1r,3r)-3-(3-bromo-1H-pyrrolo[3,2-c]pyridin-1-yl)-3-(cyanomethyl)cyclobutyl-1-carbonitrile (compound I9) and (1s,3s)-3-(3-bromo-1H-pyrrolo[3,2-c]pyridin-1-yl)-3-(cyanomethyl)cyclobutyl-1-carbonitrile (compound I10)

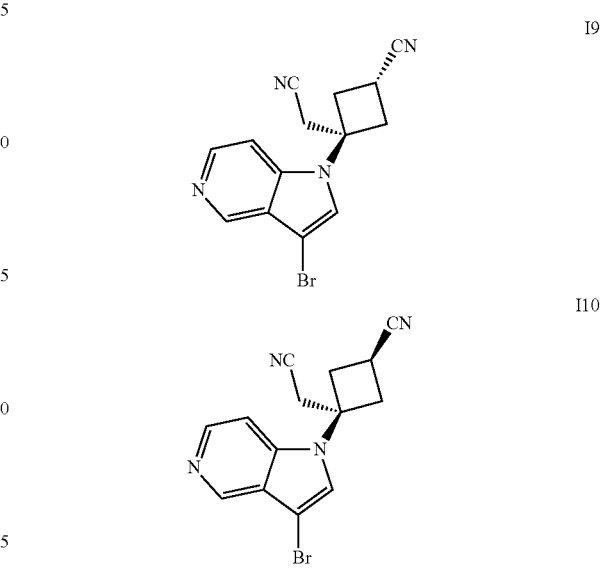

At 25° C., to a solution of 3-(cyanomethylene)cyclobutyl-1-carbonitrile (3.3 g, 27.7 mmol) in MeCN (40 mL) was added 3-bromo-1H-pyrrolo[3,2-c]pyridine (6.0 g, 30.5 mmol) and DBU (7.0 g, 5.0 mmol). After stirring at 25° C. for 48 hours, the mixture was concentrated. The residue was diluted with ethyl acetate and washed with water (×2), dried over anhydrous sodium sulfate, filtered, concentrated in vacuo, and purified by column chromatography to afford (1s,3s)-3-(3-bromo-1H-pyrrolo[3,2-c]pyridin-1-yl)-3-(cyanomethyl)cyclobutyl-1-carbonitrile (Compound I10) (570 mg, yield 6%) and (1r,3r)-3-(3-bromo-1H-pyrrolo[3,2-c]pyridin-1-yl)-3-(cyanomethyl)cyclobutyl-1-carbonitrile (Compound I9) (2.7 g, yield 28%).

(1s,3s)-3-(3-bromo-1H-pyrrolo[3,2-c]pyridin-1-yl)-3-(cyanomethyl)cyclobutyl-1-carbonitrile $^1$H NMR (400 MHz, CDCl$_3$) δ 8.91 (s, 1H), 8.40 (d, J=4.0 Hz, 1H), 7.19 (s, 1H), 7.03 (d, J=4.0 Hz, 1H), 3.39-3.30 (m, 3H), 3.27 (s, 2H), 3.10-3.03 (m, 2H).

m/z=315[M+1]$^+$.

(1r,3r)-3-(3-bromo-1H-pyrrolo[3,2-c]pyridin-1-yl)-3-(cyanomethyl)cyclobutyl-1-carbonitrile 1H NMR (400 MHz, CDCl₃) δ 8.91 (s, 1H), 8.40 (d, J=4.0 Hz, 1H), 7.13 (s, 1H), 7.01 (d, J=4.0 Hz, 1H), 3.42-3.36 (m, 1H), 3.29-3.16 (m, 4H), 2.97 (s, 2H).
m/z=315[M+1]⁺.

Preparation Example 9 (1r,3r)-3-(5-bromo-7H-pyrrolo[2,3-d]pyrimidin-7-yl)-3-(cyanomethyl)cyclobutane-1-carbonitrile (Compound I11) and (1s,3s)-3-(5-bromo-7H-pyrrolo[2,3-d]pyrimidin-7-yl)-3-(cyanomethyl)cyclobutane-1-carbonitrile (Compound I12)

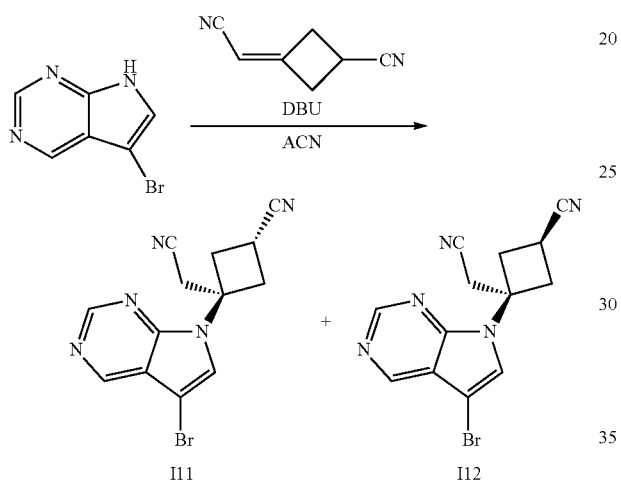

At 25° C., to a solution of 3-(cyanomethylene)cyclobutyl-1-carbonitrile (6.0 g, 50.4 mmol) in MeCN (40 mL) was added 5-bromo-7H-pyrrolo[2,3-d]pyrimidine (5.0 g, 25.2 mmol) and DBU (7.7 g, 50.4 mmol). After stirring at 25° C. for 48 hours, the mixture was concentrated. The residue was diluted with ethyl acetate and washed with water (×2), dried over anhydrous sodium sulfate, filtered, concentrated in vacuo, and purified by column chromatography to afford (1s,3s)-3-(5-bromo-7H-pyrrolo[2,3-d]pyrimidin-7-yl)-3-(cyanomethyl)cyclobutyl-1-carbonitrile (Compound I12) (0.48 g, yield 6%) and (1r,3r)-3-(5-bromo-7H-pyrrolo[2,3-d]pyrimidin-7-yl)-3-(cyanomethyl)cyclobutyl-1-carbonitrile (Compound I11) (2.2 g, yield 280%)

(1s,3s)-3-(5-bromo-7H-pyrrolo[2,3-d]pyrimidin-7-yl)-3-(cyanomethyl)cyclobutyl-1-carbonitrile ¹H NMR (400 MHz, CDCl₃) δ 8.96 (s, 1H), 8.89 (s, 1H), 7.32 (s, 1H), 3.46 (s, 2H), 3.38-3.32 (m, 3H), 3.10-3.06 (m, 2H).
m/z=316[M+1]⁺.

(1r,3r)-3-(5-bromo-7H-pyrrolo[2,3-d]pyrimidin-7-yl)-3-(cyanomethyl)cyclobutyl-1-carbonitrile 1H NMR (400 MHz, CDCl₃) δ 8.98 (s, 1H), 8.89 (s, 1H), 7.29 (s, 1H), 3.52-3.44 (m, 1H), 3.38-3.31 (m, 2H), 3.24 (s, 2H), 3.22-3.20 (m, 2H).
m/z=316[M+1]⁺.

Preparation Example 10 6-(1-methyl-1H-pyrazol-4-yl)pyrazolo[1,5-a]pyridine-4-trifluoromethanesulfonate (Compound I13)

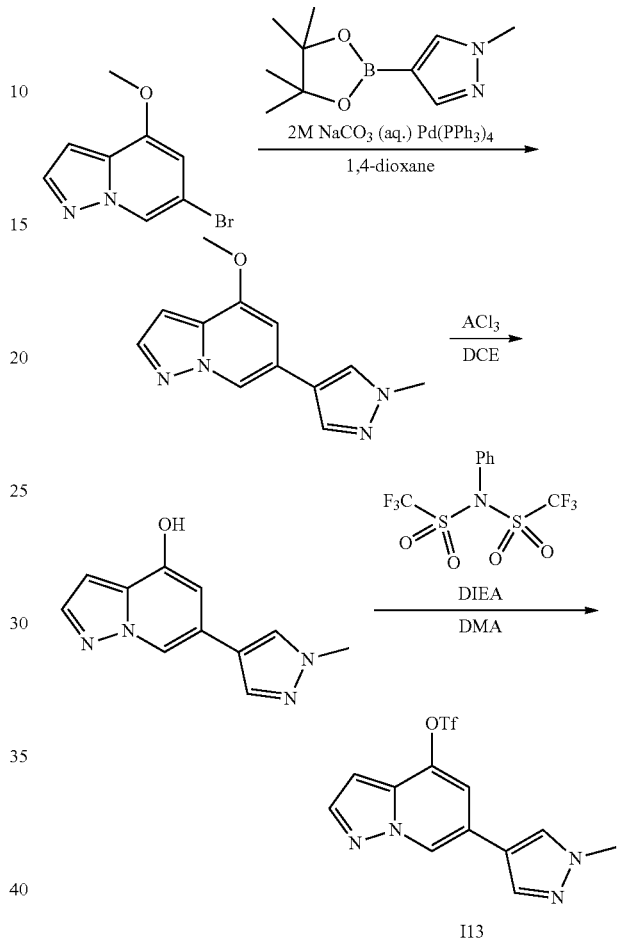

Step A: 4-methoxy-6-(1-methyl-1H-pyrazol-4-yl)pyrazolo[1,5-a]pyridine

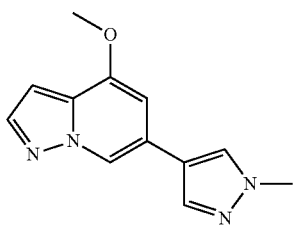 [SMILES: COc1cc(-c2cnn(C)c2)cn2nccc12]

At 25° C., to a solution of 6-bromo-4-methoxy-pyrazolo[1,5-a]pyridine (1.0 g, 4.4 mmol) and 1-methyl-4-(4,4,5,5-tetramethyl-1,3,2-dioxaborolan-2-yl)-1H-pyrazole (1.1 g, 5.3 mmol) in 1,4-dioxane (15 mL) were added 2 M Na₂CO₃ (6.6 mL, 13.2 mmol) and a catalytic amount of tetrakis(triphenylphosphine) palladium (105 mg, 0.09 mmol), and ventilated with nitrogen three times. The reaction mixture was reacted at 80° C. for 6 hours under the protection of a nitrogen balloon. After the completion of the reaction monitored by TLC, the reaction was quenched by adding water, and then extracted with ethyl acetate. The combined organic phases were washed once with water, once with saturated brine, dried over anhydrous sodium sulfate, filtered, concentrated in vacuo, and purified by column chromatography to afford the title compound (1.0 g, yield 100%) for directly used in the next reaction.

m/z=229[M+1]+.

Step B: 4-hydroxy-6-(1-methyl-1H-pyrazol-4-yl)pyrazolo[1,5-a]pyridine

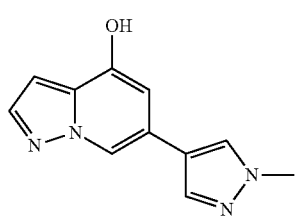 [SMILES: Cn1cc(-c2cc(O)c3ccnn3c2)cn1]

At 25° C., to a solution of 4-methoxy-6-(1-methyl-1H-pyrazol-4-yl)pyrazolo[1,5-a]pyridine (1.0 g, 4.4 mmol) in 1,2-dichloroethane (20 mL) was added aluminum trichloride (2.9 g, 22.0 mmol). The reaction mixture was reacted at 80° C. for 5 hours under the protection of a nitrogen balloon. After the completion of the reaction monitored by TLC, the reaction mixture was slowly poured into ice water for quenching, and then extracted with ethyl acetate. The combined organic phases were washed once with water and once with saturated brine, dried over anhydrous sodium sulfate, filtered, concentrated in vacuo, and purified by column chromatography to afford the title compound (0.9 g, yield 96%)), directly for use in the next reaction.

m/z=215[M+1]+.

Step C: 6-(1-methyl-1H-pyrazol-4-yl)pyrazolo[1,5-a]pyridine-4-trifluoromethanesulfonate (Compound I13)

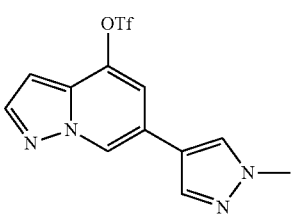

At 25° C., to a suspension of 4-hydroxy-6-(1-methyl-1H-pyrazol-4-yl)pyrazolo[1,5-a]pyridine (0.9 g, 4.2 mmol) in N,N-dimethylacetamide (10 mL) were added N-phenyl-bis(trifluoromethanesulfonyl)imide (1.8 g, 5.0 mmol) and DIEA (1.4 mL, 8.4 mmol). The reaction mixture was protected by a nitrogen balloon and reacted at room temperature for 2 hours. After the completion of the reaction monitored by TLC, the reaction mixture was quenched by slowly adding water dropwise and then extracted with ethyl acetate. The combined organic phases were washed once with water and once with saturated brine, dried over anhydrous sodium sulfate, filtered, and concentrated in vacuo, purified by column chromatography to afford 6-(1-methyl-1H-pyrazol-4-yl)pyrazolo[1,5-a]pyridine-4-trifluoromethanesulfonate (compound I13) (1.2 g, yield 70%).

m/z=347[M+1]+.

Preparation Example 11
4,6-dichloropyrazolo[1,5-a]pyrazine (Compound I14)

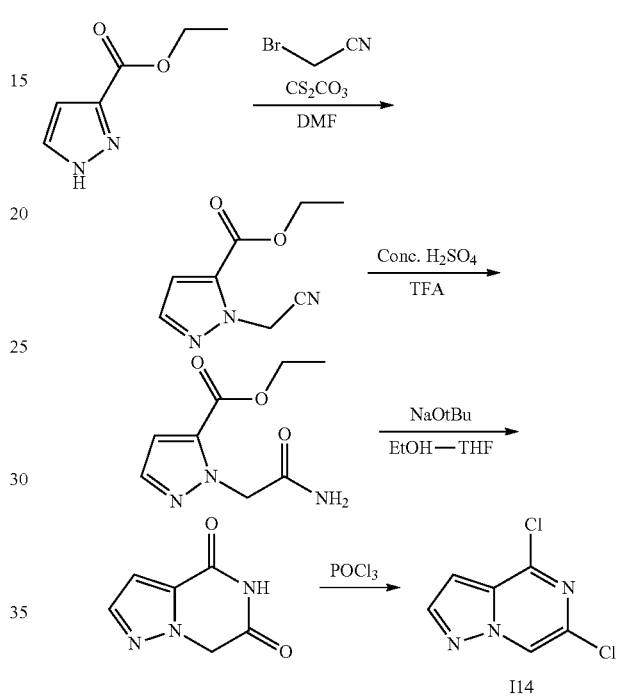

Step A: ethyl 1-(cyanomethyl)-1H-pyrazole-5-carboxylate

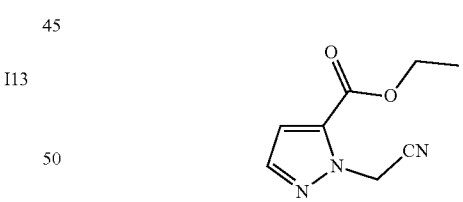

At 25° C., cesium carbonate (28.2 g, 86.4 mmol) was added to a solution of ethyl 1H-pyrazole-3-carboxylate (10 g, 72.0 mmol) in DMF (100 mL). The mixture was stirred for 10 minutes, and bromoacetonitrile was added (9.5 g, 79.2 mmol), reacted at 30° C. for 12 hours. After the completion of the reaction monitored by TLC, the reaction mixture was slowly poured into ice water for quenching, and then extracted with ethyl acetate. The organic phases were combined, washed once with water and once with saturated brine, dried with sodium sulfate, filtered, concentrated in vacuo, and purified by column chromatography to afford the title compound (6.3 g, yield 49%), which was directly used in the next reaction.

m/z=180[M+1]+.

Step B: ethyl 1-(2-amino-2-oxo-ethyl)-1H-pyrazole-5-carboxylate

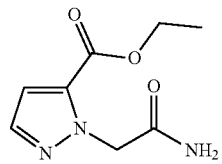

At 25° C., to a solution of ethyl 1-(cyanomethyl)-1H-pyrazole-5-carboxylate (6.3 g, 35.2 mmol) in TFA (30 mL) was slowly dropwise added concentrated sulfuric acid (17.2 g, 176.0 mmol). The reaction was carried out at 25° C. for 20 hours. After the completion of the reaction monitored by TLC, TFA was removed under vacuum. The residue was slowly poured into ice water and extracted with ethyl acetate. The organic phases were combined, dried with anhydrous sodium sulfate, filtered, concentrated in vacuo, and purified by column chromatography to afford the title compound (6.6 g, yield 95%), which was directly used in the next reaction.
m/z=198[M+1]+.

Step C: Pyrazolo[1,5-a]pyrazine-4,6(5H,7H)-dione

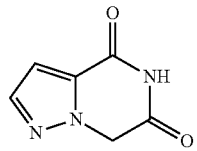 [SMILES: O=C1Cn2nccc2C(=O)N1]

At 25° C., to a solution of ethyl 1-(2-amino-2-oxo-ethyl)-1H-pyrazole-5-carboxylate (6.6 g, 35.0 mmol) in ethanol (100 mL) was added a solution of sodium ethoxide (10 g, 105.0 mmol)) in tetrahydrofuran (20 mL). The mixture was reacted at 70° C. for 16 hours. After the completion of the reaction monitored by TLC, cool the mixture to room temperature, and adjust the pH to about 6 with concentrated hydrochloric acid. A large amount of white solid was precipitated out, filtered, and dried in vacuum to afford the title compound (4.8 g, yield 91%) which was used directly in the next reaction.
m/z=152[M+1]+.

Step D: 4,6-dichloropyrazolo[1,5-a]pyrazine (Compound I14)

I14

At about 25° C., a mixture of pyrazolo[1,5-a]pyrazine-4,6(5H,7H)-dione (4.8 g, 31.8 mmol) in phosphorus oxychloride (100 mL) was heated at 120° C. for about 16 hours. Most of the POCl3 was removed under vacuum, and the remaining POCl3 was neutralized with a saturated Na2CO3 aqueous solution and extracted with DCM (3×200 mL). The combined DCM phase was dried over anhydrous sodium sulfate, filtered, concentrated, and purified by column chromatography to afford 4,6-dichloropyrazolo[1,5-a]pyrazine (Compound I14) (1.2 g, yield 20%).
m/z=188[M+1]+.

Example 1 2,2'-(3-(3-amino-4-(6-(1-methyl-1H-pyrazol-4-yl)pyrazolo[1,5-a]pyrazine-4-yl)-1H-pyrazol-1-yl)azetidine-1,3-diyl)diacetonitrile

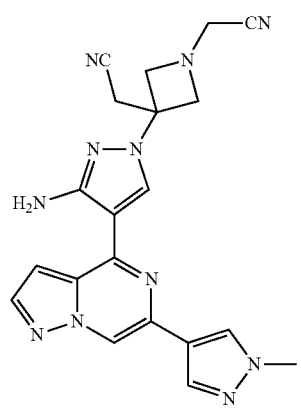 [SMILES: Cn1cc(-c2cn3nccc3c(-c3cn(C4(CC#N)CN(CC#N)C4)nc3N)n2)cn1]

Step A: 3-(3-amino-4-(6-(1-methyl-1H-pyrazol-4-yl)pyrazolo[1,5-a]pyrazin-4-yl)-1H-pyrazol-1-yl)-3-(cyanomethyl)azetidine-1-carboxylic Acid Tert-Butyl Ester

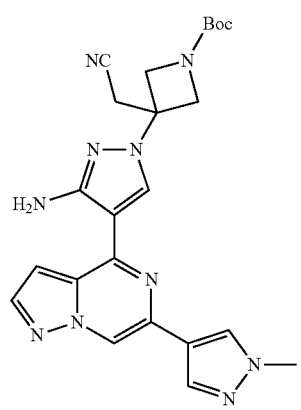 [SMILES: Cn1cc(-c2cn3nccc3c(-c3cn(C4(CC#N)CN(C(=O)OC(C)(C)C)C4)nc3N)n2)cn1]

To a flask, were added 4-chloro-6-(1-methyl-1H-pyrazol-4-yl)pyrazolo[1,5-a]pyrazine (288 mg, 1.23 mmol), 3-(3-amino-4-(4,4,5,5-tetramethyl-1,3,2-dioxaborolan-2-yl)-1H-pyrazol-1-yl)-3-(cyanomethyl)azetidine-1-carboxylic acid tert-butyl ester (747 mg, 1.85 mmol), 2 M Na2CO3 aqueous solution (1.85 mL) and 1,4-dioxane (20 mL). Bubbling nitrogen into the mixture. [1,1'-bis(diphenylphosphino)ferrocene]palladium dichloride (183 mg, 0.3 mmol) was added to the mixture. The mixture was bubbling with nitrogen for 3 minutes. The reaction was carried out at 110° C. under nitrogen balloon protection for 2 hours. TLC monitored the completion of the reaction. The reaction mixture was diluted with water and extracted with ethyl acetate. The organic phases were combined, washed once with water and once with saturated brine, dried over anhydrous sodium sulfate, filtered, concentrated in vacuo and purified by column chromatography to afford the title compound as a white foam solid (502 mg, yield 86%)

$^1$H NMR (400 MHz, CDCl$_3$) δ 8.40 (s, 1H), 8.06 (s, 1H), 8.03 (d, J=2.3 Hz, 1H), 7.91 (s, 1H), 7.81 (s, 1H), 6.86 (d, J=1.7 Hz, 1H), 5.62 (s, 2H), 4.49 (d, J=9.5 Hz, 2H), 4.22 (d, J=9.5 Hz, 2H), 4.00 (s, 3H), 3.25 (s, 2H), 1.47 (s, 9H). m/z=475[M+1]$^+$.

Step B: 2-(3-(3-amino-4-(6-(1-methyl-1H-pyrazol-4-yl)pyrazolo[1,5-a]pyrazin-4-yl)-1H-pyrazol-1-yl)azetidin-3-yl)acetonitrile

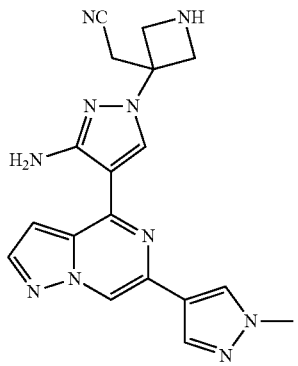 [SMILES: Cn1cc(-c2cn3nccc3c(-c3cn(C4(CC#N)CNC4)nc3N)n2)cn1]

At about 10° C., TFA (3 mL) was slowly added dropwise to a solution of 3-(3-amino-4-(6-(1-methyl-1H-pyrazol-4-yl)pyrazolo[1,5-a)pyrazin-4-yl)-1H-pyrazol-1-yl)-3-(cyanomethyl)azetidine-1-carboxylic acid tert-butyl ester (502 mg, 1.1 mmol) in DCM (20 mL). After about 90 minutes, the mixture was concentrated. The residue was concentrated twice with toluene, and then dried under vacuum to afford the title compound (396 mg, yield 100%), which was used directly without further purification.
m/z=375[M+1]$^+$.

Step C: 2,2'-(3-(3-amino-4-(6-(1-methyl-1H-pyrazol-4-yl)pyrazolo[1,5-a]pyrazine-4-yl)-1H-pyrazol-1-yl)azetidine-1,3-diyl)diacetonitrile

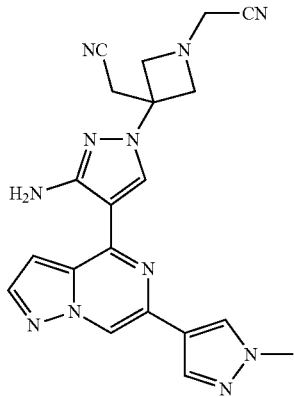 [SMILES: Cn1cc(-c2cn3nccc3c(-c3cn(C4(CC#N)CN(CC#N)C4)nc3N)n2)cn1]

DIPEA (0.7 mL, 5.5 mmol) was added to a solution of 2-(3-(3-amino-4-(6-(1-methyl-1H-pyrazol-4-yl)pyrazolo[1,5-a]pyrazin-4-yl)-1H-pyrazol-1-yl)azetidin-3-yl)acetonitrile (396 mg, 1.1 mmol) in DMF (10 mL). At approximately 25° C., bromoacetonitrile (158 mg, 1.3 mmol) was added. After about 18 hours, TLC monitored the completion of the reaction. Water was added to the reaction mixture to quench the reaction and then extracted with ethyl acetate. The organic phases were combined, washed once with water and once with saturated brine, dried over anhydrous sodium sulfate, filtered, concentrated in vacuo, and purified by column chromatography to afford the title compound as a white foam solid (118 mg, yield 26%).

$^1$H NMR (400 MHz, DMSO-d$_6$) δ 8.93 (s, 1H), 8.62 (s, 1H), 8.26 (s, 1H), 8.20 (d, J=2.4 Hz, 1H), 8.03 (s, 1H), 7.48 (d, J=1.6 Hz, 1H), 6.32 (s, 2H), 3.93 (s, 3H), 3.87 (d, J=8.6 Hz, 2H), 3.83 (s, 2H), 3.64 (d, J=8.7 Hz, 2H), 3.49 (s, 2H). m/z=414[M+1]$^+$.

Example 2 2-(3-(3-amino-4-(6-(1-methyl-TH-pyrazol-4-yl)pyrazolo[1,5-a]pyrazin-4-yl)-1H-pyrazol-1-yl)-1-(ethylsulfonyl)azetidin-3-yl)acetonitrile

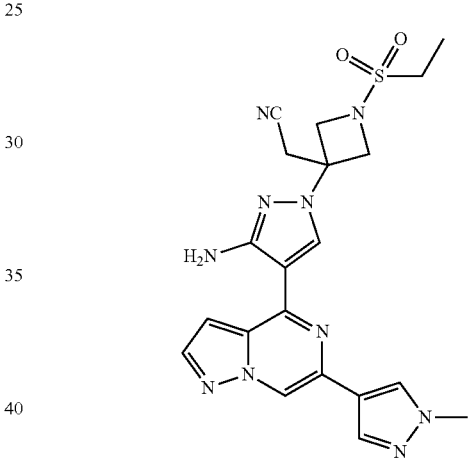

To a flask, were added 4-chloro-6-(1-methyl-1H-pyrazol-4-yl)pyrazolo[1,5-a]pyrazine (126 mg, 0.54 mmol), 2-(3-(3-amino-4-(4,4,5,5-tetramethyl-1,3,2-dioxaborolan-2-yl)-1H-pyrazol-1-yl)-1-(ethylsulfonyl)azetidin-3-yl)acetonitrile (320 mg, 0.81 mmol), 2 M Na$_2$CO$_3$ aqueous solution (0.8 mL) and 1,4-dioxane (10 mL). Bubbling nitrogen into the mixture. [1,1'-bis(diphenylphosphino)ferrocene]palladium dichloride (80 mg, 0.11 mmol) was added to the mixture. The mixture was bubbling with nitrogen for 3 minutes. The reaction was carried out at 110° C. under nitrogen balloon protection for 2 hours. TLC monitored the completion of the reaction. The reaction mixture was diluted with water and extracted with ethyl acetate. The organic phases were combined, washed once with water and once with saturated brine, dried over anhydrous sodium sulfate, filtered, concentrated in vacuo and purified by column chromatography to afford the title compound as a white foam solid (55 mg, yield 22%).

$^1$H NMR (400 MHz, DMSO-d$_6$) δ 8.92 (s, 1H), 8.65 (s, 1H), 8.25 (s, 1H), 8.19 (d, J=2.4 Hz, 1H), 8.01 (s, 1H), 7.48 (d, J=1.7 Hz, 1H), 6.35 (s, 2H), 4.57 (d, J=9.1 Hz, 2H), 4.15 (d, J=9.1 Hz, 2H), 3.91 (s, 3H), 3.59 (s, 2H), 3.23 (q, J=7.3 Hz, 2H), 1.24 (t, J=7.3 Hz, 3H). m/z=467[M+1]$^+$.

Example 3 2-(3-(3-amino-4-(6-(1-methyl-1H-pyrazol-4-yl)pyrazolo[1,5-a]pyrazin-4-yl)-1H-pyrazol-1-yl)-1-(isopropylsulfonyl)azetidin-3-yl)acetonitrile

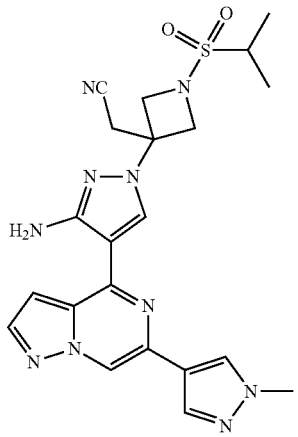 [SMILES: CC(C)S(=O)(=O)N1CC(CC#N)(n2cc(-c3nc(-c4cnn(C)c4)cn4nccc34)c(N)n2)C1]

To a flask, were added 4-chloro-6-(1-methyl-1H-pyrazol-4-yl)pyrazolo[1,5-a]pyrazine (195 mg, 0.83 mmol), 2-(3-(3-amino-4-(4,4,5,5-tetramethyl-1,3,2-dioxaborolan-2-yl)-1H-pyrazol-1-yl)-1-(isopropylsulfonyl)azetidin-3-yl)acetonitrile (510 mg, 1.25 mmol), 2 M Na$_2$CO$_3$ aqueous solution (1.3 mL) and 1,4-dioxane (10 mL). Bubbling nitrogen into the mixture. [1,1'-bis(diphenylphosphino)ferrocene]palladium dichloride (117 mg, 0.16 mmol) was added to the mixture. The mixture was bubbling with nitrogen for 3 minutes. The reaction was carried out at 110° C. under nitrogen balloon protection for 2 hours. TLC monitored the completion of the reaction. The reaction mixture was diluted with water and extracted with ethyl acetate. The organic phases were combined, washed once with water and once with saturated brine, dried over anhydrous sodium sulfate, filtered, concentrated in vacuo and purified by column chromatography to afford the title compound as a white foam solid (233 mg, yield 58%).

$^1$H NMR (400 MHz, DMSO-d$_6$) δ 8.92 (s, 1H), 8.64 (s, 1H), 8.24 (s, 1H), 8.18 (d, J=2.4 Hz, 1H), 8.01 (s, 1H), 7.47 (d, J=1.8 Hz, 1H), 6.35 (s, 2H), 4.57 (d, J=8.8 Hz, 2H), 4.11 (d, J=8.9 Hz, 2H), 3.91 (s, 3H), 3.60 (s, 2H), 3.38-3.34 (m, 1H), 1.26 (d, J=6.8 Hz, 6H).

m/z=481 [M+1]$^+$.

Example 4 4-(3-amino-1-(3-(cyanomethyl)-1-(isopropylsulfonyl)azetidin-3-yl)-1H-pyrazol-4-yl)-6-(1-methyl-1H-pyrazol-4-yl)pyrazolo[1,5-a]pyrazine-3-carbonitrile

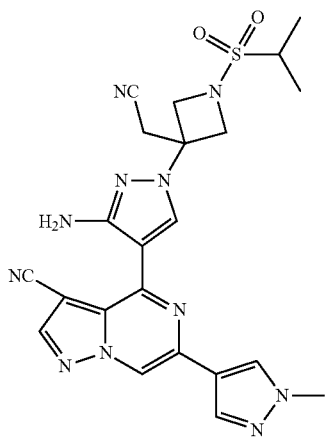 [SMILES: CC(C)S(=O)(=O)N1CC(CC#N)(n2cc(-c3nc(-c4cnn(C)c4)cn4ncc(C#N)c34)c(N)n2)C1]

To a flask, were added 4-chloro-6-(1-methyl-1H-pyrazol-4-yl)pyrazolo[1,5-a]pyrazine-3-carbonitrile (250 mg, 0.97 mmol), 2-(3-(3-amino-4-(4,4,5,5-tetramethyl-1,3,2-dioxaborolan-2-yl)-1H-pyrazole-1-yl)-1-(isopropylsulfonyl)azetidin-3-yl)acetonitrile (475 mg, 1.16 mmol), 2 M Na$_2$CO$_3$ aqueous solution (1.2 mL) and 1,4-dioxane (15 mL). Bubbling nitrogen into the mixture. [1,1'-bis(diphenylphosphino)ferrocene]palladium dichloride (113 mg, 0.16 mmol) was added to the mixture. The mixture was bubbling with nitrogen for 3 minutes. The reaction was carried out at 110° C. under nitrogen balloon protection for 2 hours. TLC monitored the completion of the reaction. The reaction mixture was diluted with water and extracted with ethyl acetate. The organic phases were combined, washed once with water and once with saturated brine, dried over anhydrous sodium sulfate, filtered, concentrated in vacuo and purified by column chromatography to afford the title compound as a white foam solid (456 mg, yield 93%).

$^1$H NMR (400 MHz, DMSO-d$_6$) δ 9.18 (s, 1H), 8.83 (s, 1H), 8.59 (s, 1H), 8.36 (s, 1H), 8.10 (s, 1H), 5.84 (s, 2H), 4.43 (d, J=8.7 Hz, 2H), 4.18 (d, J=8.7 Hz, 2H), 3.91 (s, 3H), 3.52 (s, 2H), 3.38-3.30 (m, 1H), 1.25 (d, J=6.8 Hz, 6H).

m/z=506[M+1]$^+$.

Examples 5 and 6 2-((1r,3s)-1-(3-amino-4-(6-(1-methyl-1H-pyrazol-4-yl)pyrazolo[1,5-a]pyrazin-4-yl)-1H-pyrazol-1-yl)-3-hydroxycyclobutyl)acetonitrile (trans isomer) and 2-((1s,3r)-1-(3-amino-4-(6-(1-methyl-1H-pyrazol-4-yl)pyrazolo[1,5-a]pyrazin-4-yl)-1H-pyrazol-1-yl)-3-hydroxycyclobutyl)acetonitrile (Cis Isomer)

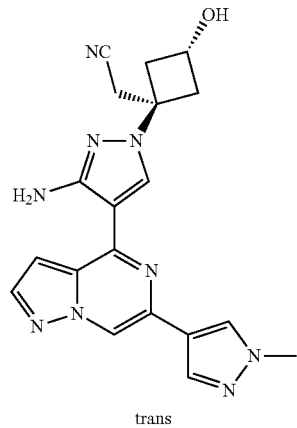

trans

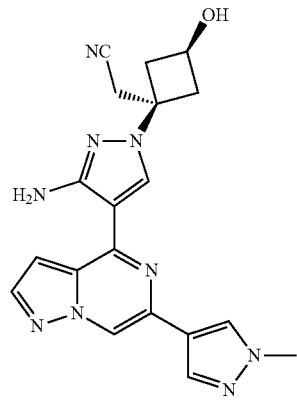

cis

Step A: 2-(1-(3-amino-4-(6-(1-methyl-1H-pyrazol-4-yl)pyrazolo[1,5-a]pyrazin-4-yl)-1H-pyrazol-1-yl)-3-(benzyloxy)cyclobutyl)acetonitrile

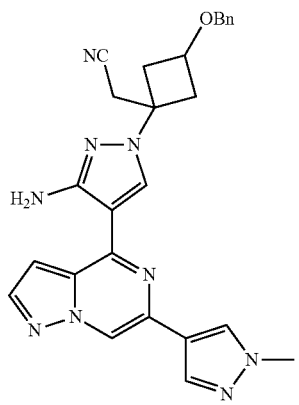 [SMILES: Cn1cc(-c2cn3nccc3c(-c3cn(C4(CC#N)CC(OCc5ccccc5)C4)nc3N)n2)cn1]

To a flask, were added 4-chloro-6-(1-methyl-1H-pyrazol-4-yl)pyrazolo[1,5-a]pyrazine (213 mg, 0.91 mmol), 2-(1-(3-amino-4-(4,4,5,5-tetramethyl-1,3,2-dioxaborolan-2-yl)-1H-pyrazol-1-yl)-3-(benzyloxy)cyclobutyl)acetonitrile (cis and trans) (410 mg, 1.0 mmol), 2 M Na$_2$CO$_3$ aqueous solution (1.4 mL) and 1,4-dioxane (15 mL). Bubbling nitrogen into the mixture. [1,1'-bis(diphenylphosphino)ferrocene]palladium dichloride (146 mg, 0.2 mmol) was added to the mixture. The mixture was bubbling with nitrogen for 3 minutes. The reaction was carried out at 110° C. under nitrogen balloon protection for 2 hours. TLC monitored the completion of the reaction. The reaction mixture was diluted with water and extracted with ethyl acetate. The organic phases were combined, washed once with water and once with saturated brine, dried over anhydrous sodium sulfate, filtered, concentrated in vacuo and purified by column chromatography to afford the title compound (170 mg, yield 39%).

m/z=480[M+1]$^+$.

Step B: 2-((1r,3s)-1-(3-amino-4-(6-(1-methyl-1H-pyrazol-4-yl)pyrazolo[1,5-a]pyrazin-4-yl)-1H-pyrazol-1-yl)-3-hydroxycyclobutyl)acetonitrile (trans isomer) and 2-((1s,3r)-1-(3-amino-4-(6-(1-methyl-1H-pyrazol-4-yl)pyrazolo[1,5-a]pyrazin-4-yl)-1H-pyrazol-1-yl)-3-hydroxycyclobutyl) acetonitrile (Cis Isomer)

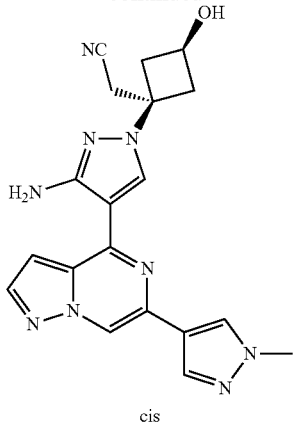

cis

The vacuum-dried NaI (524 mg, 3.5 mmol) was added to a solution of 2-(1-(3-amino-4-(6-(1-methyl-1H-pyrazol-4-yl)pyrazolo[1,5-a]pyrazin-4-yl)-1H-pyrazol-1-yl)-3-benzyloxy)cyclobutyl)acetonitrile (170 mg, 0.35 mmol) in MeCN (20 mL) in batches at about 20° C. To the solution, was add TMSCl (380 mg, 3.5 mmol). The reaction mixture was stirred at about 50° C. for 18 hours. An additional portion of NaI and TMSCl were added to the reaction mixture and maintained at about 50° C. with stirring for 8 hours. The reaction was monitored by TLC until completion. The cooled mixture was poured into an ice-cold saturated NaHCO$_3$ aqueous solution containing sodium thiosulfate pentahydrate for quenching, extracted with ethyl acetate three times, and the organic phases were combined and washed once with water and once with saturated brine, dried over anhydrous sodium sulfate, filtered, concentrated in vacuo, and purified by column chromatography to afford the title compound (trans 45 mg, cis 60 mg, total yield 77%).

m/z=390[M+1]$^+$.

Examples 7 and 8 2-((1r,3s)-1-(3-amino-4-(6-(1-methyl-1H-pyrazol-4-yl)pyrazolo[1,5-a]pyrazin-4-yl)-1H-pyrazol-1-yl)-3-methoxycyclobutyl)acetonitrile (trans isomer) and 2-((1s,3r)-1-(3-amino-4-(6-(1-methyl-1H-pyrazol-4-yl)pyrazolo[1,5-a]pyrazin-4-yl)-1H-pyrazol-1-yl)-3-methoxycyclobutyl) acetonitrile (Cis Isomer)

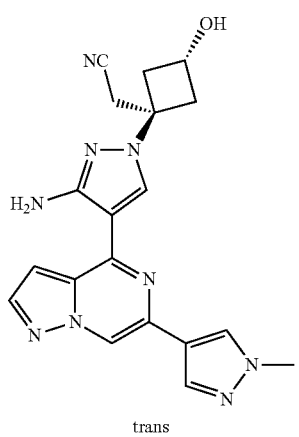

trans

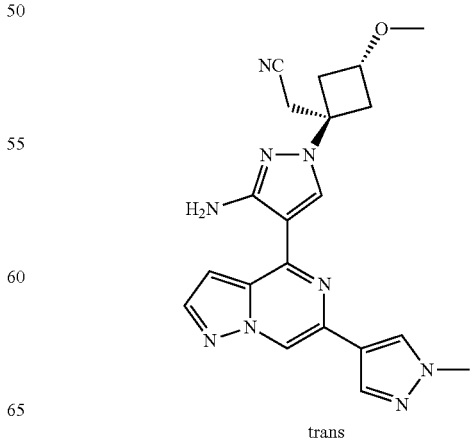

trans

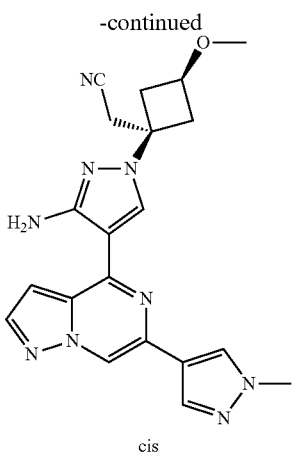

cis

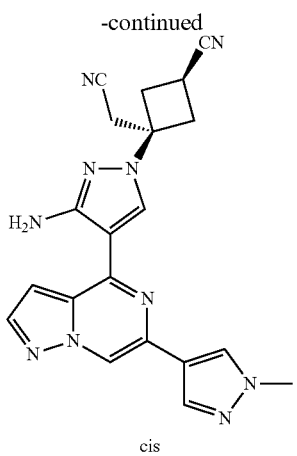

cis

At room temperature, 2-(1-(3-amino-4-(6-(1-methyl-1H-pyrazol-4-yl)pyrazolo[1,5-a]pyrazin-4-yl)-1H-pyrazol-1-yl)-3-hydroxycyclobutyl)acetonitrile (cis and trans) (105 mg, 0.27 mmol) was dissolved in a small amount of THF (10 mL), and tetrabutylammonium bromide (261 mg, 0.81 mmol), 1 M NaOH aqueous solution (3 mL) and dimethyl sulfate (170 mg, 1.35 mmol) were added thereto. The reaction flask was sealed and stirred vigorously at 20° C. for about 1 hour. Additional dimethyl sulfate (170 mg, 1.35 mmol) and tetrabutylammonium bromide (261 mg, 0.81 mmol) were added, and the reaction was kept at about 20° C. with stirring vigorously for about 2 hours. TLC monitored the completion of the reaction and extracted with ethyl acetate three times. The combined organic phases were washed once with water, once with saturated brine, dried over anhydrous sodium sulfate, filtered, concentrated in vacuo, and purified by column chromatography to afford 2-((1r,3s)-1-(3-amino-4-(6-(1-methyl-1H-pyrazol-4-yl)pyrazolo[1,5-a]pyrazin-4-yl)-1H-pyrazol-1-yl)-3-methoxycyclobutyl)acetonitrile (trans) (28 mg, yield 26%) and 2-((1s,3r)-1-(3-amino-4-(6-(1-methyl-1H-pyrazol-4-yl)pyrazolo[1,5-a]pyrazin-4-yl)-1H-pyrazol-1-yl)-3-methoxycyclobutyl)acetonitrile (cis) (40 mg, yield 37%).

m/z=404[M+1]$^+$.

Examples 9 and 10 (1r,3r)-3-(3-amino-4-(6-(1-methyl-1H-pyrazol-4-yl)pyrazolo[1,5-a]pyrazin-4-yl)-1H-pyrazol-1-yl)-3-(cyanomethyl)cyclobutyl-1-carbonitrile and (1s,3s)-3-(3-amino-4-(6-(1-methyl-1H-pyrazol-4-yl)pyrazolo[1,5-a]pyrazin-4-yl)-1H-pyrazol-1-yl)-3-(cyanomethyl)cyclobutyl-1-carbonitrile

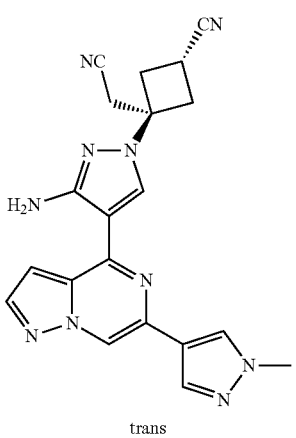

trans

To a flask, were added 4-chloro-6-(1-methyl-1H-pyrazol-4-yl)pyrazolo[1,5-a]pyrazine (234 mg, 1.0 mmol), (1r,3r)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile (359 mg, 1.1 mmol), 2 M Na$_2$CO$_3$ aqueous solution (1.5 mL) and 1,4-dioxane (15 mL). Bubbling nitrogen into the mixture for 3 minutes. [1,1'-bis(diphenylphosphino)ferrocene]palladium dichloride (146 mg, 0.2 mmol) was added to the mixture. The mixture was bubbling with nitrogen for 3 minutes. The reaction was carried out at 110° C. under nitrogen balloon protection for 2 hours. TLC monitored the completion of the reaction. The reaction mixture was diluted with water and extracted with ethyl acetate. The organic phases were combined, washed once with water and once with saturated brine, dried over anhydrous sodium sulfate, filtered, concentrated in vacuo and purified by column chromatography to afford (1r,3r)-3-(3-amino-4-(6-(1-methyl-1H-pyrazol-4-yl)pyrazolo[1,5-a]pyrazin-4-yl)-1H-pyrazol-1-yl)-3-(cyanomethyl)cyclobutyl-1-carbonitrile (130 mg, yield 33%).

$^1$H NMR (400 MHz, DMSO-d$_6$) δ 8.91 (s, 1H), 8.59 (s, 1H), 8.24 (s, 1H), 8.18 (d, J=2.3 Hz, 1H), 8.01 (s, 1H), 7.49 (d, J=1.9 Hz, 1H), 6.30 (s, 2H), 3.91 (s, 3H), 3.58-3.49 (m, 1H), 3.41 (s, 2H), 3.29-3.18 (m, 2H), 2.89-2.75 (m, 2H).

m/z=399[M+1]$^+$.

(1r,3r)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile was replaced with (1s,3s)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile (450 mg, 1.4 mmol) to perform the same procedures to afford (1s,3s)-3-(3-amino-4-(6-(1-methyl-1H-pyrazol-4-yl)pyrazolo[1,5-a]pyrazin-4-yl)-1H-pyrazol-1-yl)-3-(cyanomethyl)cyclobutyl-1-carbonitrile (188 mg, yield 38%).

$^1$H NMR (400 MHz, DMSO-d$_6$) δ 8.91 (s, 1H), 8.54 (s, 1H), 8.24 (s, 1H), 8.18 (d, J=2.4 Hz, 1H), 8.02 (s, 1H), 7.48 (d, J=1.6 Hz, 1H), 6.32 (s, 2H), 3.91 (s, 3H), 3.58-3.50 (m, 1H), 3.49 (s, 2H), 3.18-3.13 (m, 2H), 2.78-2.73 (in, 2H).

m/z=399[M+1]$^+$.

Synthesize the example compounds in the below table with reference to the synthetic methods of the above intermediates and example compounds.

Example 11
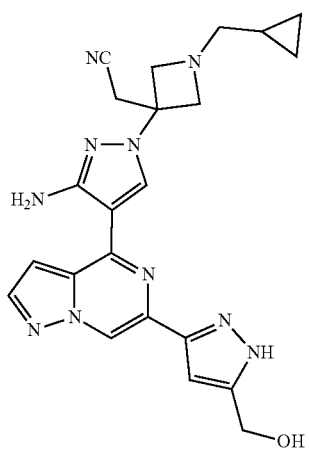
m/z = 445[M + 1]+
Example 12
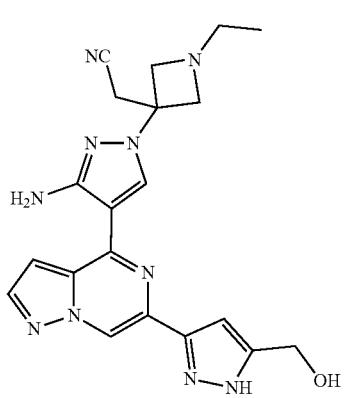
m/z = 419[M + 1]+
Example 13
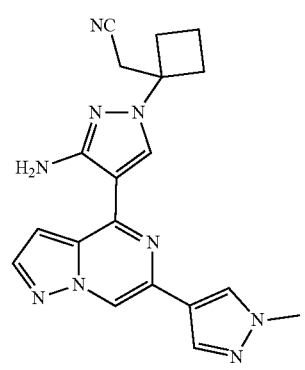
m/z = 374[M + 1]+
Example 14
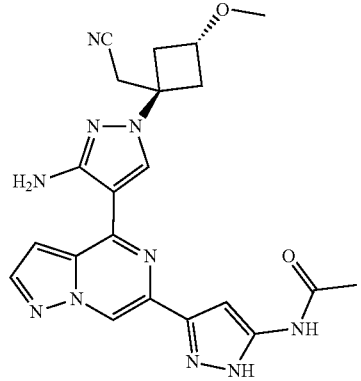
m/z = 447[M + 1]+
Example 15
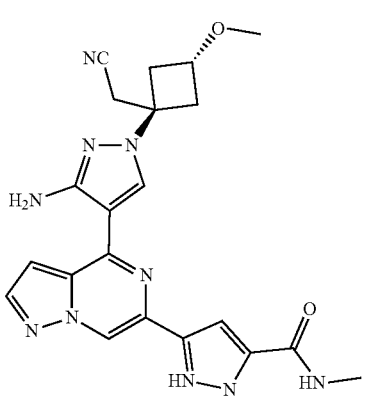
m/z = 447[M + 1]+
Example 16
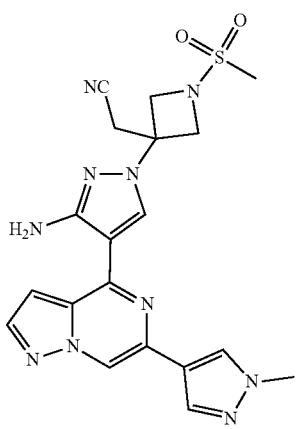
m/z = 453[M + 1]+

Example 17
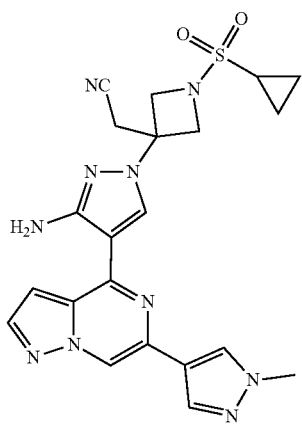
m/z = 479[M + 1]+
Example 18
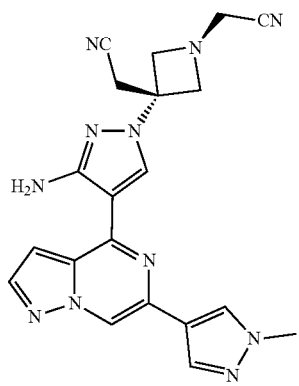
m/z = 431[M + 1]+
Example 19
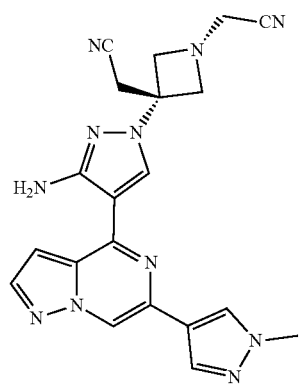
m/z = 413[M + 1]+
Example 20
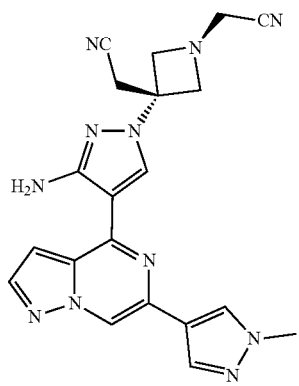
m/z = 413[M + 1]+
Example 21
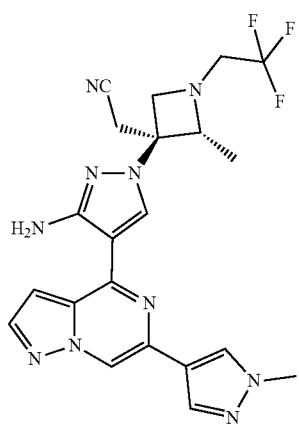
m/z = 471[M + 1]+
Example 22
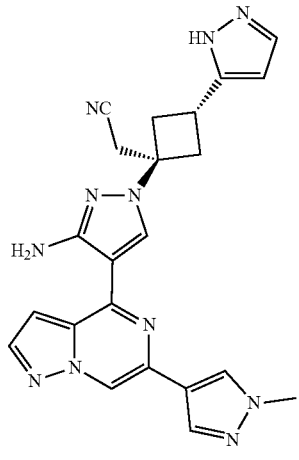
m/z = 440[M + 1]+

Example 23
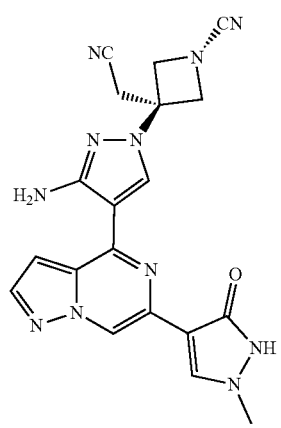
m/z = 415[M + 1]+
Example 24
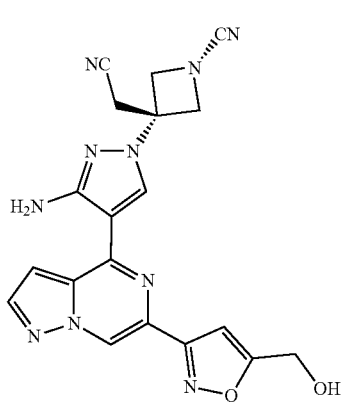
m/z = 416[M + 1]+
Example 25
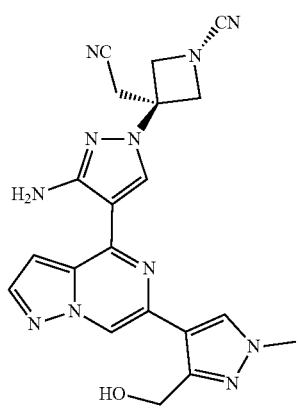
m/z = 429[M + 1]+
Example 26
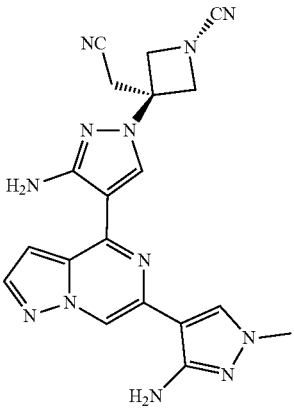
m/z = 414[M + 1]+
Example 27
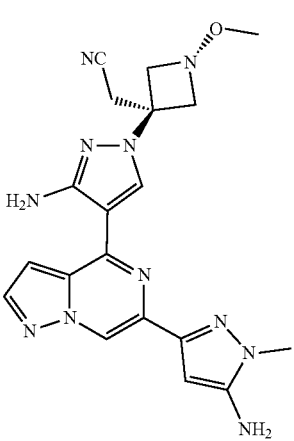
m/z = 419[M + 1]+
Example 28
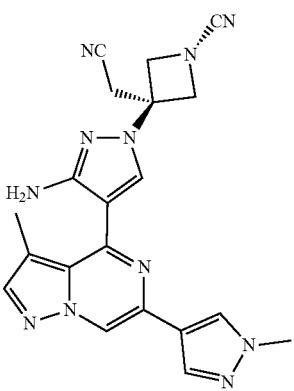
m/z = 413[M + 1]+

Example 29
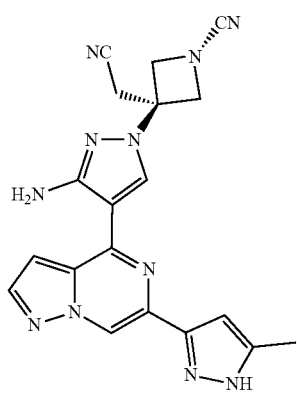
m/z = 399[M + 1]+
Example 30
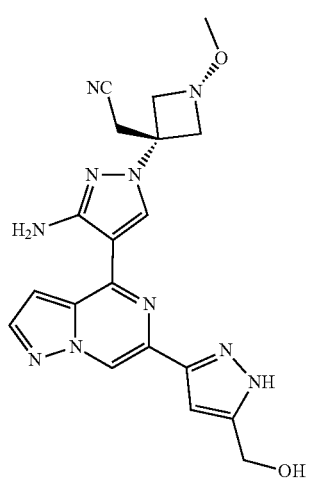
m/z = 420[M + 1]+
Example 31
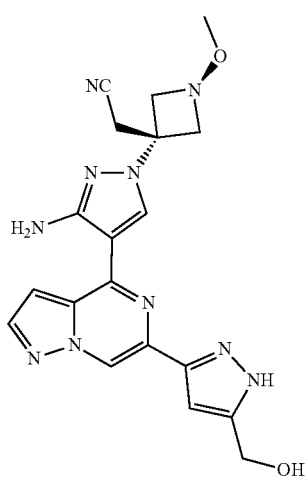
m/z = 420[M + 1]+
Example 32
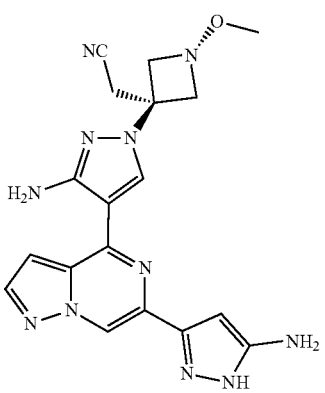
m/z = 405[M + 1]+
Example 33
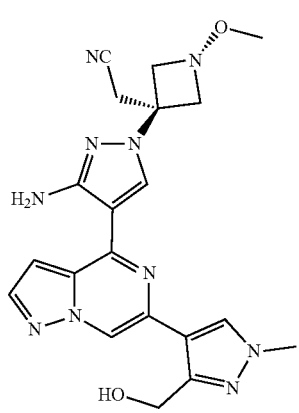
m/z = 434[M + 1]+
Example 34
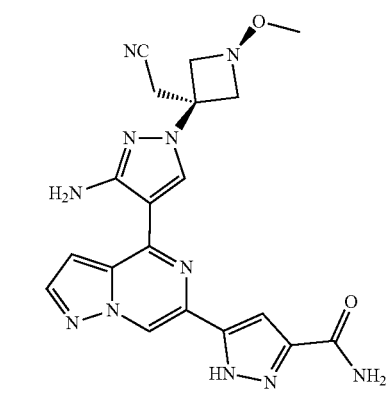
m/z = 433[M + 1]+

-continued

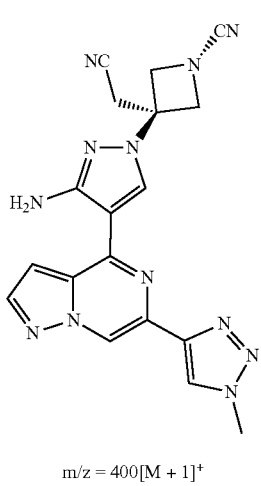

m/z = 400[M + 1]⁺

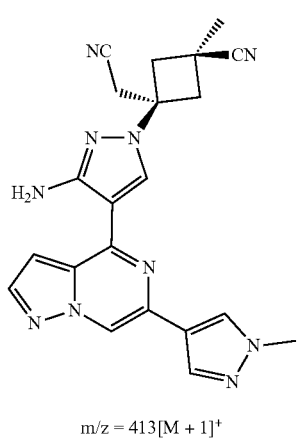

m/z = 413[M + 1]⁺

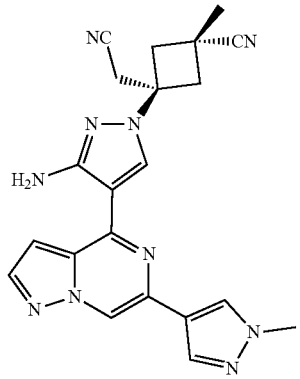

m/z = 413[M + 1]⁺

Example 35

Example 36

Example 37

Example 38 (1r,3r)-3-(cyanomethyl)-3-(4-(6-(1-methyl-1H-pyrazol-4-yl)pyrazolo[1,5-a]pyrazin-4-yl)-3-(methyl amino)-1H-pyrazol-1-yl)cyclobutane-1-carbonitrile

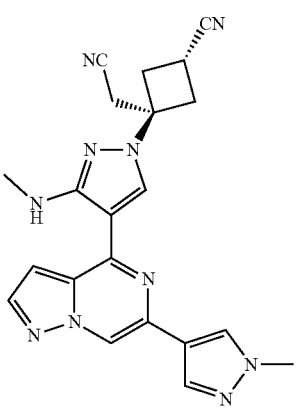

At 25° C., to a solution of (1r,3r)-3-(3-amino-4-(6-(1-methyl-1H-pyrazol-4-yl)pyrazolo[1,5-a]pyrazin-4-yl)-1H-pyrazol-1-yl)-3-(cyanomethyl)cyclobutyl-1l-carbonitrile (50 mg, 0.13 mmol) in 1,4-dioxane (6 mL) were added methylboronic acid (22 mg, 0.38 mmol), pyridine (40 mg, 0.52 mmol) and copper acetate (68 mg, 0.38 mmol). The reaction was carried out at 110° C. under nitrogen protection for 4 hours, and was monitored by TLC till completed. Then, the reaction mixture was quenched by adding water and extracted with ethyl acetate. The organic phases were combined and washed once with water and once with saturated brine, dried over anhydrous sodium sulfate, filtered, concentrated in vacuo, and purified by column chromatography to afford the title compound (8 mg, yield 16%).
m/z=413[M+1]+.

Example 39 (1r,3r)-3-(cyanomethyl)-3-(3-(dimethylamino)-4-(6-(1-methyl-1H-pyrazol-4-yl)pyrazolo[1,5-a]pyrazin-4-yl)-1H-pyrazol-1-yl)cyclobutane-1-carbonitrile

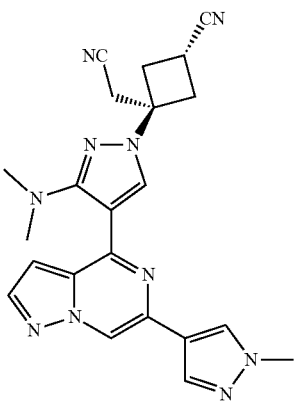

At 25° C., to a mixture of (1r,3r)-3-(3-amino-4-(6-(1-methyl-1H-pyrazol-4-yl)pyrazolo[1,5-a]pyrazin-4-yl)-1H-pyrazol-1-yl)-3-(cyanomethyl)cyclobutyl-1-carbonitrile (50 mg, 0.13 mmol) in MeOH (6 mL) was added DCM (3 mL)

to aid dissolution, to which were added formaldehyde aqueous solution (37%) (70 mg, 0.86 mmol) and a small spoon of 10% palladium on carbon, and reacted overnight at room temperature under a hydrogen balloon. After the completion of the reaction monitored by TLC, the reaction system was filtered and concentrated under reduced pressure and purified by column chromatography to afford the title compound (20 mg, yield 36%). 1H NMR (400 MHz, CDCl$_3$) δ 8.47 (s, 1H), 8.01-7.97 (m, 3H), 7.93 (s, 1H), 7.03 (s, 1H), 3.98 (s, 3H), 3.30-3.24 (m, 3H), 3.20 (s, 2H), 2.87-2.83 (m, 2H), 2.81 (s, 6H).

m/z=427[M+1]+.

Example 40 N-(1-((1r,3r)-3-cyano-1-(cyanomethyl) cyclobutyl)-4-(6-(1-methyl-1H-pyrazol-4-yl)pyrazolo[1,5-a]pyrazin-4-yl)-1H-pyrazol-3-yl)acetamide

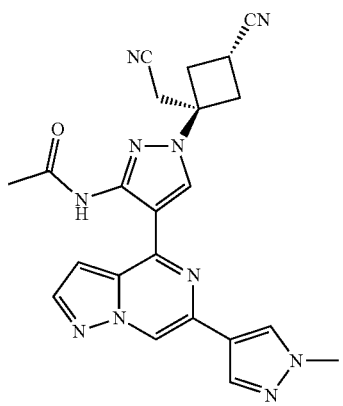 [SMILES: CC(=O)Nc1nn([C@]2(CC#N)C[C@@H](C#N)C2)cc1-c1nc(-c2cnn(C)c2)cn2nccc12]

At 25° C., to a solution of (1r,3r)-3-(3-amino-4-(6-(1-methyl-1H-pyrazol-4-yl)pyrazolo[1,5-a]pyrazin-4-yl)-1H-pyrazol-1-yl)-3-(cyanomethyl)cyclobutyl-1-carbonitrile (50 mg, 0.13 mmol) in DCM (10 mL) were added acetyl chloride (205 mg, 2.6 mmol) and catalytic amount of DMAP (9 mg, 0.07 mmol). The reaction mixture was reacted at room temperature for two hours under nitrogen protection. TLC monitored the completion of the reaction. The reaction mixture was quenched by adding water and extracted with ethyl acetate. The combined organic phase was washed once with water and once with saturated brine, dried over anhydrous sodium sulfate, filtered, concentrated in vacuo, and purified by column chromatography to afford the title compound (48 mg, yield 87%).

1H NMR (400 MHz, DMSO-d$_6$) δ 10.49 (brs, 1H), 9.02 (s, 1H), 8.78 (brs, 1H), 8.29 (s, 1H), 8.20 (s, 1H), 8.09 (s, 1H), 7.33 (brs, 1H), 3.96 (s, 3H), 3.68-3.52 (m, 1H), 3.48 (s, 2H), 3.29-3.25 (m, 2H), 2.92-2.87 (m, 2H), 2.32-1.92 (m, 3H).

m/z=441[M+1]+.

Example 41 (1r,3r)-3-(3-amino-4-(6-(1-methyl-1H-pyrazol-4-yl)-[1,2,4]triazolo[1,5-a]pyrazin-8-yl)-1H-pyrazol-1-yl)-3-(cyanomethyl)cyclobutane-1-carbonitrile

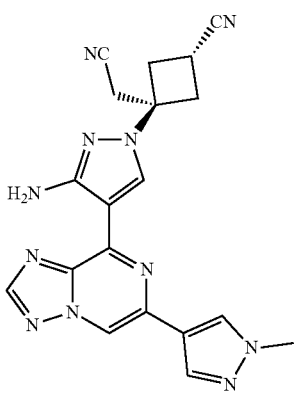 [SMILES: Cn1cc(-c2cn3ncnc3c(-c3cn([C@]4(CC#N)C[C@@H](C#N)C4)nc3N)n2)cn1]

Step A: (1r,3r)-3-(3-amino-4-(6-bromo-[1,2,4]triazolo[1,5-a]pyrazin-8-yl)-1H-pyrazol-1-yl)-3-(cyanomethyl)cyclobutane-1-carbonitrile

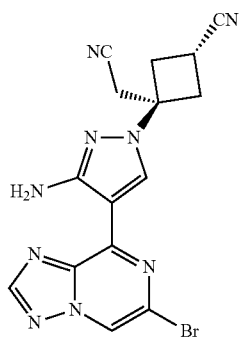 [SMILES: N#CC[C@]1(n2cc(-c3nc(Br)cn4ncnc34)c(N)n2)C[C@H](C#N)C1]

At 25° C., to a solution of 6,8-dibromo-[1,2,4]triazolo[1,5-a]pyrazine (200 mg, 0.72 mmol) and (1r,3r)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile (285 mg, 0.87 mmol) in 1,4-dioxane (15 mL) was added 2 M Na$_2$CO$_3$ (1.1 mL, 2.16 mmol) and a catalytic amount of [1,1'-bis(diphenylphosphino)ferrocene]palladium dichloride (59 mg, 0.08 mmol), ventilated with nitrogen three times, reacted at room temperature under nitrogen balloon protection for 6 hours, TLC monitored the completion of the reaction, and the reaction mixture was quenched with water and extracted with ethyl acetate. The organic phases were combined, washed once with water and once with saturated brine, dried over anhydrous sodium sulfate, filtered, concentrated under reduced pressure in vacuo, and purified by column chromatography to afford the title compound (140 mg, yield 49%), directly used in the next step.

m/z=398[M+1]+.

Step B: (1r,3r)-3-(3-amino-4-(6-(1-methyl-1H-pyrazol-4-yl)-[1,2,4]triazolo[1,5-a]pyrazin-8-yl)-1H-pyrazol-1-yl)-3-(cyanomethyl)cyclobutane-1-carbonitrile

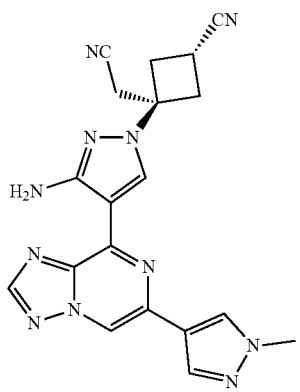 [SMILES: Cn1cc(-c2cn3ncnc3c(-c3cn([C@]4(CC#N)C[C@@H](C#N)C4)nc3N)n2)cn1]

At 25° C., to a solution of (1r,3r)-3-(3-amino-4-(6-bromo-[1,2,4]triazolo[1,5-a]pyrazin-8-yl)-1H-pyrazol-1-yl)-3-(cyanomethyl)cyclobutane-1-carbonitrile (140 mg, 0.35 mmol) and 1-methyl-4-(4,4,5,5-tetramethyl-1,3,2-dioxaborolan-2-yl)-1H-pyrazole (87 mg, 0.42 mmol) in 1,4-dioxane (15 mL) was added 2 M Na$_2$CO$_3$ (0.5 mL, 1.0 mmol) and a catalytic amount of [1,1'-bis(diphenylphosphino)ferrocene]palladium dichloride (30 mg, 0.04 mmol), ventilated with nitrogen three times, reacted at 110° C. under nitrogen balloon protection for 2 hours, TLC monitored the completion of the reaction, and the reaction mixture was quenched with water and extracted with ethyl acetate. The organic phases were combined, washed once with water and once with saturated brine, dried over anhydrous sodium sulfate, filtered, concentrated under reduced pressure in vacuo, and purified by column chromatography to afford the title compound (60 mg, yield 43%).

m/z=400[M+1]$^+$.

Example 42 (1r,3r)-3-(3-amino-4-(6-(1-methyl-1H-pyrazol-4-yl)pyrazolo[1,5-a]pyridin-4-yl)-1H-pyrazol-1-yl)-3-(cyanomethyl)cyclobutane-1-carbonitrile

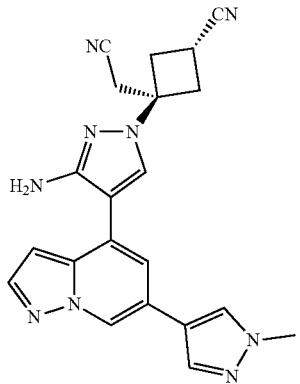 [SMILES: Cn1cc(-c2cc(-c3cn([C@]4(CC#N)C[C@@H](C#N)C4)nc3N)c3ccnn3c2)cn1]

At 25° C., to a solution of 6-(1-methyl-1H-pyrazol-4-yl)pyrazolo[1,5-a]pyridine-4-trifluoromethanesulfonate (100 mg, 0.3 mmol) and (1r,3r)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile (95 mg, 0.3 mmol) in 1,4-dioxane (10 mL) was added 2 M Na$_2$CO$_3$ (0.5 mL, 1.0 mmol) and a catalytic amount of [1,1'-bis(diphenylphosphino)ferrocene]palladium dichloride (22 mg, 0.03 mmol), ventilated with nitrogen three times, reacted at 90° C. under nitrogen balloon protection for 4 hours, TLC monitored the completion of the reaction, and the reaction mixture was quenched with water and extracted with ethyl acetate. The organic phases were combined, washed once with water and once with saturated brine, dried over anhydrous sodium sulfate, filtered, concentrated under reduced pressure in vacuo, and purified by column chromatography to afford the title compound (43 mg, yield 37%).

m/z=398[M+1]$^+$.

Example 43 (is, 3s)-3-(3-amino-4-(6-(1-methyl-TH-pyrazol-4-yl)pyrazolo[1,5-a]pyridin-4-yl)-1H-pyrazol-1-yl)-3-(cyanomethyl)cyclobutane-1-carbonitrile

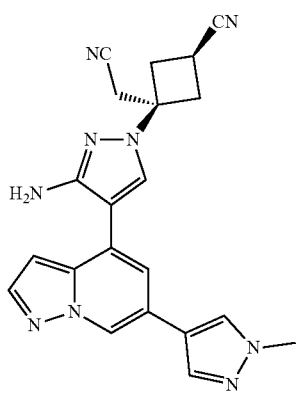 [SMILES: Cn1cc(-c2cc(-c3cn([C@]4(CC#N)C[C@H](C#N)C4)nc3N)c3ccnn3c2)cn1]

At 25° C., to a solution of 6-(1-methyl-1H-pyrazol-4-yl)pyrazolo[1,5-a]pyridine-4-trifluoromethanesulfonate (100 mg, 0.3 mmol) and (1s,3s)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile (95 mg, 0.3 mmol) in 1,4-dioxane (10 mL) was added 2 M Na$_2$CO$_3$ (0.7 mL, 1.4 mmol) and a catalytic amount of [1,1'-bis(diphenylphosphino)ferrocene]palladium dichloride (22 mg, 0.03 mmol), ventilated with nitrogen three times, reacted at 90° C. under nitrogen balloon protection for 4 hours, TLC monitored the completion of the reaction, and the reaction mixture was quenched with water and extracted with ethyl acetate. The organic phases were combined, washed once with water and once with saturated brine, dried over anhydrous sodium sulfate, filtered, concentrated under reduced pressure in vacuo, and purified by column chromatography to afford the title compound (57 mg, yield 50%).

m/z=398[M+1]$^+$.

Example 44 (1r,3r)-3-(3-amino-4-(6-(2-hydroxy-2-methylpropoxy)pyrazolo[1,5-a]pyrazin-4-yl)-1H-pyrazol-1-yl)-3-(cyanomethyl)cyclobutane-1-carbonitrile

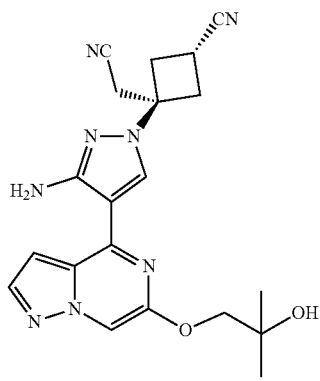 [SMILES: CC(C)(O)COc1cn2nccc2c(-c2cn([C@]3(CC#N)C[C@@H](C#N)C3)nc2N)n1]

Step A: (1r,3r)-3-(3-amino-4-(6-chloropyrazolo[1,5-a]pyrazin-4-yl)-1H-pyrazol-1-yl)-3-(cyanomethyl)cyclobutane-1-carbonitrile

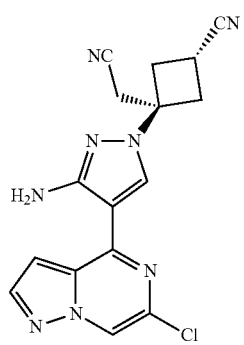 [SMILES: N#CC[C@]1(n2cc(-c3nc(Cl)cn4nccc34)c(N)n2)C[C@H](C#N)C1]

At 25° C., to a solution of 4,6-dichloropyrazolo[1,5-a]pyrazine (400 mg, 2.13 mmol) and (1r,3r)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile (838 mg, 2.56 mmol) in 1,4-dioxane (30 mL) was added 2 M Na$_2$CO$_3$ (3.2 mL, 6.39 mmol) and a catalytic amount of [1,1'-bis(diphenylphosphino)ferrocene]palladium dichloride (154 mg, 0.21 mmol), ventilated with nitrogen three times, reacted at room temperature under nitrogen balloon protection for 6 hours, TLC monitored the completion of the reaction, and the reaction mixture was quenched with water and extracted with ethyl acetate. The organic phases were combined, washed once with water and once with saturated brine, dried over anhydrous sodium sulfate, filtered, concentrated under reduced pressure in vacuo, and purified by column chromatography to afford the title compound (316 mg, yield 42%), directly used in the next step.

m/z=353[M+1]$^+$.

Step B: (1r,3r)-3-(3-amino-4-(6-(2-hydroxy-2-methylpropoxy)pyrazolo[1,5-a]pyrazin-4-yl)-1H-pyrazol-1-yl)-3-(cyanomethyl)cyclobutane-1-carbonitrile

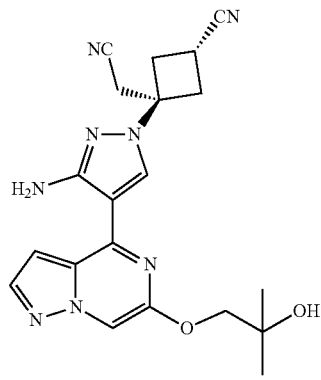 [SMILES: CC(C)(O)COc1cn2nccc2c(-c2cn([C@]3(CC#N)C[C@@H](C#N)C3)nc2N)n1]

At 25° C., to a sealing tube was added (1r,3r)-3-(3-amino-4-(6-chloropyrazolo[1,5-a]pyrazin-4-yl)-1H-pyrazol-1-yl)-3-(cyanomethyl)cyclobutane-1-carbonitrile (100 mg, 0.28 mmol), K$_2$CO$_3$ (138 mg, 1.0 mmol), 2,2-dimethylpropylene oxide (25 mg, 0.34 mmol) and DMF (10 mL), and were reacted at 60° C. for 12 hours. After the completion of the reaction monitored by TLC, the reaction mixture was quenched by adding water, extracted with ethyl acetate. The organic phases were combined, washed once with water and once with saturated brine, dried over anhydrous sodium sulfate, filtered, concentrated under reduced pressure in vacuo, and purified by column chromatography to afford the title compound (34 mg, yield 30%).

m/z=407[M+1]+.

Example 45 (1r,3r)-3-(cyanomethyl)-3-(3-fluoro-4-(6-(1-methyl-1H-pyrazol-4-yl)pyrazolo[1,5-a)pyrazin-4-yl)-1H-pyrazol-1-yl)cyclobutane-1-carbonitrile

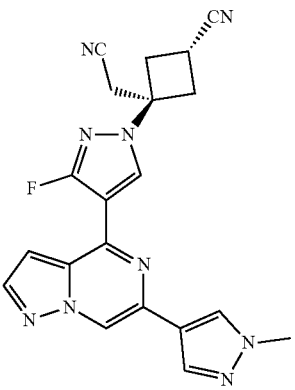 [SMILES: Cn1cc(-c2cn3nccc3c(-c3cn([C@]4(CC#N)C[C@@H](C#N)C4)nc3F)n2)cn1]

With reference to the synthetic method of Example 9, the raw material of (1r,3r)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile was replaced with (1r,3r)-3-(3-fluoro-4-(4,4,5,5-tetramethyl-1,3,2-dioxaborolan-2-yl)-1H-pyrazol-1-yl)-3-(cyanomethyl)cyclobutyl-1-carbonitrile.

m/z=402[M+1]+.

77

Example 46 (is, 3s)-3-(cyanomethyl)-3-(3-fluoro-4-(6-(1-methyl-1H-pyrazol-4-yl)pyrazolo[1,5-a]pyrazin-4-yl)-1H-pyrazol-1-yl)cyclobutane-1-carbonitrile

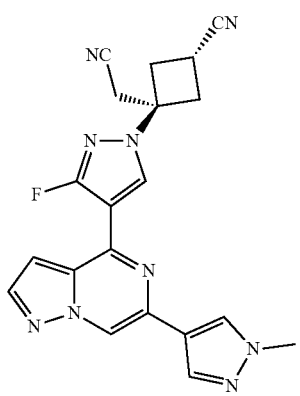 [SMILES: Cn1cc(-c2cn3nccc3c(-c3cn([C@]4(CC#N)C[C@@H](C#N)C4)nc3F)n2)cn1]

With reference to the synthetic method of Example 10, the raw material of (1s,3s)-3-(3-amino-4-(4,4,5,5-tetramethyl-1,3,2-dioxaborolan-2-yl)-1H-pyrazol-1-yl)-3-(cyanomethyl)cyclobutyl-1-carbonitrile was replaced with (is, 3s)-3-(3-fluoro-4-(4,4,5,5-tetramethyl-1,3,2-dioxaborolan-2-yl)-1H-pyrazol-1-yl)-3-(cyanomethyl)cyclobutyl-1-carbonitrile.

m/z=402[M+1]+.

Example 47 (1s,3s)-3-(cyanomethyl)-3-(3-(6-(1-methyl-1H-pyrazol-4-yl)pyrazolo[1,5-a]pyrazin-4-yl)-1H-pyrrolo[3,2-c]pyridin-1-yl)cyclobutane-1-carbonitrile

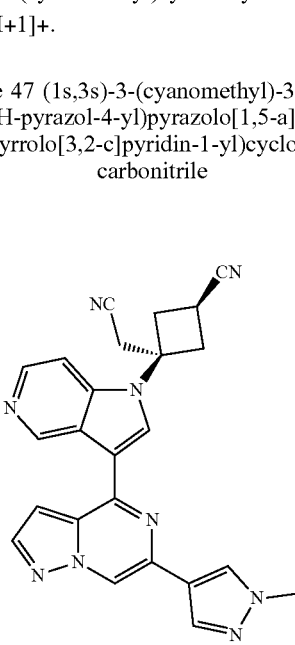

78

Step A: (1s,3s)-3-(cyanomethyl)-3-(3-(4,4,5,5-tetramethyl-1,3,2-dioxaborolan-2-yl)-1H-pyrrolo[3,2-c]pyridin-1-yl)cyclobutane-1-carbonitrile

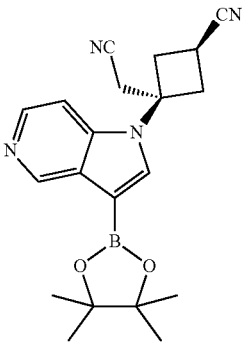 [SMILES: CC1(C)OB(c2cn([C@]3(CC#N)C[C@H](C#N)C3)c3ccncc23)OC1(C)C]

At 25° C., to a solution of (1s,3s)-3-(3-bromo-1H-pyrrolo[3,2-c]pyridin-1-yl)-3-(cyanomethyl)cyclobutyl-1-carbonitrile (0.57 g, 1.8 mmol) in 1,4-dioxane (15 mL) was added pinacol diborate (0.94 g, 3.6 mmol) and anhydrous potassium acetate (0.53 g, 5.4 mmol). The mixture was bubbling with nitrogen for 3 minutes, and [1,1'-bis(diphenylphosphino)ferrocene]palladium dichloride (146 mg, 0.2 mmol) was added thereto. The mixture was blown with nitrogen bubbling and ventilated for 3 minutes. The reaction was carried out at 95° C. for 12 hours under nitrogen balloon protection, and then reacted at 110° C. for 2 hours. TLC monitored the completion of the reaction and the obtained mixture was directly used in the next reaction.

m/z=363[M+1]+.

Step B: (1s,3s)-3-(cyanomethyl)-3-(3-(6-(1-methyl-1H-pyrazol-4-yl)pyrazolo[1,5-a]pyrazin-4-yl)-1H-pyrrolo[3,2-c]pyridin-1-yl)cyclobutane-1-carbonitrile

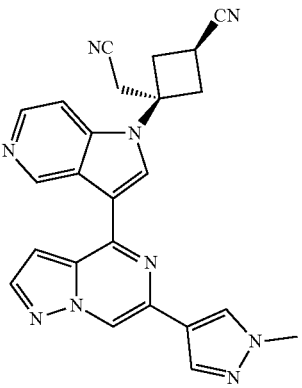 [SMILES: Cn1cc(-c2cn3nccc3c(-c3cn([C@]4(CC#N)C[C@H](C#N)C4)c4ccncc34)n2)cn1]

The mixture in the above step A was cooled to room temperature, and 4-chloro-6-(1-methyl-1H-pyrazol-4-yl)pyrazolo[1,5-a]pyrazine (250 mg, 1.1 mmol), 2 M Na₂CO₃ aqueous solution (2.3 mL) and [1,1'-bis(diphenylphosphino)ferrocene]palladium dichloride (110 mg, 0.15 mmol) were added to the reaction system. The reaction system was bubbled with nitrogen for 3 minutes, reacted at 95° C. for 2 hours under nitrogen balloon protection, and then reacted at 110° C. for 2 hours. TLC monitored the disappearance of raw materials, and water was added to dilute the reaction mixture, extracted with ethyl acetate. The organic phases were combined, washed once with water and once with saturated brine, dried over anhydrous sodium sulfate, filtered, concentrated in vacuo, and purified by column chromatography to afford the title compound (196 mg, yield 42%) 1H NMR (400 MHz, DMSO-$d_6$) δ 9.87 (s, 1H), 9.04 (s, 1H), 8.42 (brs, 2H), 8.34 (s, 1H), 8.23 (d, J=4.0 Hz, 1H), 8.12 (s, 1H), 7.57 (brs, 1H), 7.47 (s, 1H), 3.95 (s, 3H), 3.60-3.49 (m, 3H), 3.31-3.29 (m, 2H), 3.15-3.10 (m, 2H). m/z=434[M+1]$^+$.

Example 48 (1r,3r)-3-(cyanomethyl)-3-(3-(6-(1-methyl-1H-pyrazol-4-yl)pyrazolo[1,5-a]pyrazin-4-yl)-1H-pyrrolo[3,2-c]pyridin-1-yl)cyclobutane-1-carbonitrile

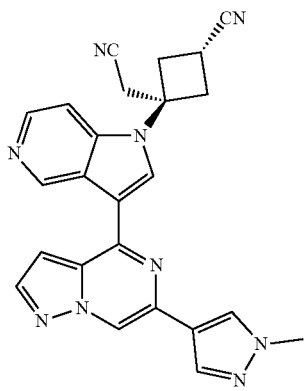 [SMILES: Cn1cc(-c2cn3nccc3c(-c3cn([C@]4(CC#N)C[C@@H](C#N)C4)c4ccncc34)n2)cn1]

Step A: (1r,3r)-3-(cyanomethyl)-3-(3-(4,4,5,5-tetramethyl-1,3,2-dioxaborolan-2-yl)-1H-pyrrolo[3,2-c]pyridin-1-yl)cyclobutane-1-carbonitrile

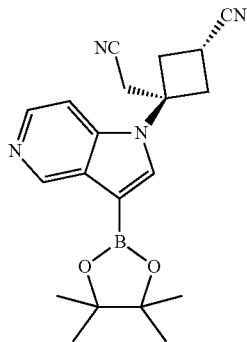 [SMILES: CC1(C)OB(c2cn([C@]3(CC#N)C[C@@H](C#N)C3)c3ccncc23)OC1(C)C]

At 25° C., to a solution of (1r,3r)-3-(3-bromo-1H-pyrrolo[3,2-c]pyridin-1-yl)-3-(cyanomethyl)cyclobutyl-1-carbonitrile (1.2 g, 3.8 mmol) in 1,4-dioxane (20 mL) was added pinacol diborate (2.4 g, 9.5 mmol) and anhydrous potassium acetate (0.75 g, 7.6 mmol). The mixture was bubbling with nitrogen for 3 minutes, and [1,1'-bis(diphenylphosphino)ferrocene]palladium dichloride (278 mg, 0.4 mmol) was added thereto. The mixture was blown with nitrogen bubbling and ventilated for 3 minutes. The reaction was carried out at 95° C. for 12 hours under nitrogen balloon protection, and then reacted at 110° C. for 2 hours. TLC monitored the completion of the reaction and the obtained mixture was directly used in the next step.

m/z=363[M+1]$^+$.

Step B: (1r,3r)-3-(cyanomethyl)-3-(3-(6-(1-methyl-1H-pyrazol-4-yl)pyrazolo[1,5-a]pyrazin-4-yl)-1H-pyrrolo[3,2-c]pyridin-1-yl)cyclobutane-1-carbonitrile

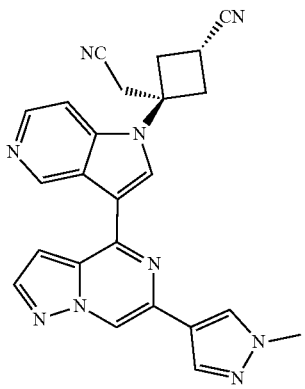 [SMILES: Cn1cc(-c2cn3nccc3c(-c3cn([C@]4(CC#N)C[C@@H](C#N)C4)c4ccncc34)n2)cn1]

The mixture obtained in the above step A was cooled to room temperature, and 4-chloro-6-(1-methyl-1H-pyrazol-4-yl)pyrazolo[1,5-a]pyrazine (355 mg, 1.5 mmol), 2 M Na$_2$CO$_3$ aqueous solution (2.3 mL) and [1,1'-bis(diphenylphosphino)ferrocene]palladium dichloride (110 mg, 0.15 mmol) were added to the reaction system. The reaction system was bubbled with nitrogen for 3 minutes, reacted at 95° C. for 2 hours under nitrogen balloon protection, and then reacted at 110° C. for 2 hours. TLC monitored the disappearance of raw materials, and water was added to dilute the reaction mixture, extracted with ethyl acetate. The organic phases were combined, washed once with water and once with saturated brine, dried over anhydrous sodium sulfate, filtered, concentrated in vacuo, and purified by column chromatography to afford the title compound (200 mg, yield 30%).

1H NMR (400 MHz, DMSO-$d_6$) δ 9.86 (s, 1H), 9.04 (s, 1H), 8.40 (d, J=4.0 Hz, 1H), 8.34 (s, 1H), 8.30 (s, 1H), 8.23 (d, J=4.0 Hz, 1H), 8.13 (s, 1H), 7.52 (d, J=8.0 Hz, 1H), 7.48 (s, 1H), 3.95 (s, 3H), 3.75-3.71 (m, 1H), 3.54 (s, 2H), 3.31-3.29 (m, 2H), 3.24-3.19 (m, 2H).

m/z=434[M+1]$^+$.

Example 49 (1s,3s)-3-(cyanomethyl)-3-(5-(6-(1-methyl-1H-pyrazol-4-yl)pyrazolo[1,5-a]pyrazin-4-yl)-7H-pyrrolo[2,3-d]pyrimidin-7-yl)cyclobutane-1-carbonitrile

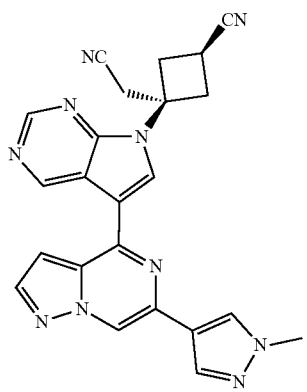 [SMILES: Cn1cc(-c2cn3nccc3c(-c3cn([C@]4(CC#N)C[C@H](C#N)C4)c4ncncc34)n2)cn1]

Step A: (1s,3s)-3-(cyanomethyl)-3-(5-(4,4,5,5-tetramethyl-1,3,2-dioxaborolan-2-yl)-7H-pyrrolo[2,3-d]pyrimidin-7-yl)cyclobutane-1-carbonitrile

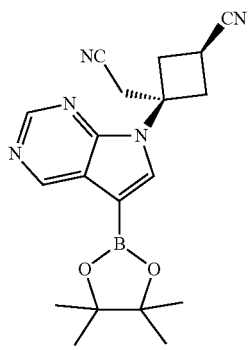 [SMILES: CC1(C)OB(c2cn([C@]3(CC#N)C[C@H](C#N)C3)c3ncncc23)OC1(C)C]

At 25° C., to a solution of (1s,3s)-3-(5-bromo-7H-pyrrolo[3,2-d]pyrimidin-7-yl)-3-(cyanomethyl)cyclobutyl-1-carbonitrile (0.48 g, 1.5 mmol) in 1,4-dioxane (15 mL) was added pinacol diborate (0.77 g, 3.0 mmol) and anhydrous potassium acetate (0.45 g, 4.6 mmol). The mixture was bubbled with nitrogen for 3 minutes, and [1,1'-bis(diphenylphosphino)ferrocene]palladium dichloride (110 mg, 0.2 mmol) was added thereto. The mixture was blown with nitrogen bubbling and ventilated for 3 minutes. The reaction was carried out at 95° C. for 12 hours under nitrogen balloon protection, and then reacted at 110° C. for 2 hours. TLC monitored the completion of the reaction and the obtained mixture was directly used in the next step.

m/z=364[M+1]$^+$.

Step B: (1s,3s)-3-(cyanomethyl)-3-(5-(6-(1-methyl-1H-pyrazol-4-yl)pyrazolo[1,5-a]pyrazin-4-yl)-7H-pyrrolo[2,3-d]pyrimidin-7-yl)cyclobutane-1-carbonitrile

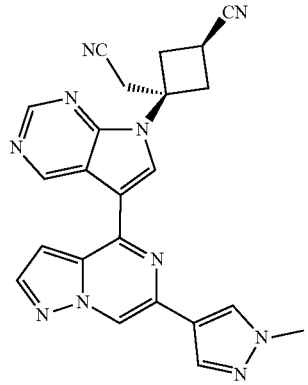

The mixture obtained in the above step A was cooled to room temperature, and 4-chloro-6-(1-methyl-1H-pyrazol-4-yl)pyrazolo[1,5-a]pyrazine (200 mg, 1.1 mmol), 2 M Na$_2$CO$_3$ aqueous solution (1.9 mL) and [1,1'-bis(diphenylphosphino)ferrocene]palladium dichloride (100 mg, 0.14 mmol) were added to the reaction system. The reaction system was bubbled with nitrogen for 3 minutes, reacted at 95° C. for 2 hours under nitrogen balloon protection, and then reacted at 110° C. for 2 hours. TLC monitored the disappearance of raw materials, and water was added to dilute the reaction mixture, extracted with ethyl acetate. The organic phases were combined, washed once with water and once with saturated brine, dried over anhydrous sodium sulfate, filtered, concentrated in vacuo, and purified by column chromatography to afford the title compound (150 mg, yield 40%).

1H NMR (400 MHz, CDCl$_3$) δ 9.91 (s, 1H), 9.07 (s, 1H), 8.99 (s, 1H), 8.60 (s, 1H), 8.38 (s, 1H), 8.25 (s, 1H), 8.13 (s, 1H), 7.58 (s, 1H), 3.95 (s, 3H), 3.71-3.62 (m, 3H), 3.28 (s, 2H), 3.07-3.03 (m, 2H).

m/z=435[M+1]$^+$.

Example 50 (1r,3r)-3-(cyanomethyl)-3-(5-(6-(1-methyl-1H-pyrazol-4-yl)pyrazolo[1,5-a]pyrazin-4-yl)-7H-pyrrolo[2,3-d]pyrimidin-7-yl)cyclobutane-1-carbonitrile

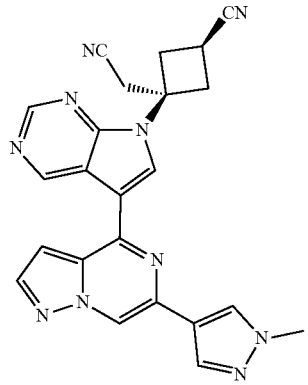 [SMILES: Cn1cc(-c2cn3nccc3c(-c3cn([C@]4(CC#N)C[C@H](C#N)C4)c4ncncc34)n2)cn1]

Step A: (1r,3r)-3-(cyanomethyl)-3-(5-(4,4,5,5-tetramethyl-1,3,2-dioxaborolan-2-yl)-7H-pyrrolo[2,3-d]pyrimidin-7-yl)cyclobutane-1-carbonitrile

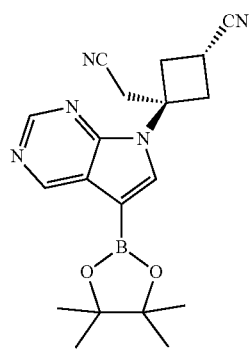 [SMILES: CC1(C)OB(c2cn([C@]3(CC#N)C[C@@H](C#N)C3)c3ncncc23)OC1(C)C]

At 25° C., to a solution of (1r,3r)-3-(5-bromo-7H-pyrrolo[3,2-d]pyrimidin-7-yl)-3-(cyanomethyl)cyclobutyl-1-carbonitrile (1.0 g, 3.2 mmol) in 1,4-dioxane (15 mL) was added pinacol diborate (2.0 g, 7.9 mmol) and anhydrous potassium acetate (1.1 g, 11.2 mmol). The mixture was bubbled with nitrogen for 3 minutes, and [1,1'-bis(diphenylphosphino)ferrocene]palladium dichloride (250 mg, 0.34 mmol) was added thereto. The mixture was blown with nitrogen bubbling and ventilated for 3 minutes. The reaction was carried out at 95° C. for 12 hours under nitrogen balloon protection, and then reacted at 110° C. for 2 hours. TLC monitored the completion of the reaction and the obtained mixture was directly used in the next step.

m/z=364[M+1]$^+$.

Step B: (1r,3r)-3-(cyanomethyl)-3-(5-(6-(1-methyl-1H-pyrazol-4-yl)pyrazolo[1,5-a]pyrazin-4-yl)-7H-pyrrolo[2,3-d]pyrimidin-7-yl)cyclobutane-1-carbonitrile

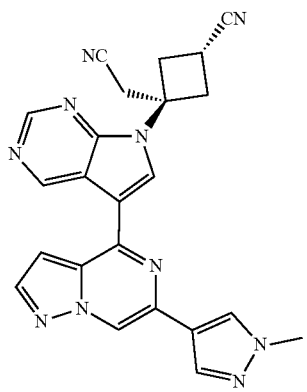 [SMILES: Cn1cc(-c2cn3nccc3c(-c3cn([C@]4(CC#N)C[C@@H](C#N)C4)c4ncncc34)n2)cn1]

The mixture obtained in the above step A was cooled to room temperature, and 4-chloro-6-(1-methyl-1H-pyrazol-4-yl)pyrazolo[1,5-a]pyrazine (400 mg, 1.7 mmol), 2 M Na$_2$CO$_3$ aqueous solution (2.3 mL) and [1,1'-bis(diphenylphosphino)ferrocene]palladium dichloride (100 mg, 0.14 mmol) were added to the reaction system. The reaction system was bubbled with nitrogen for 3 minutes, reacted at 95° C. for 2 hours under nitrogen balloon protection, and then reacted at 110° C. for 2 hours. TLC monitored the disappearance of raw materials, and water was added to dilute the reaction mixture, extracted with ethyl acetate. The organic phases were combined, washed once with water and once with saturated brine, dried over anhydrous sodium sulfate, filtered, concentrated in vacuo, and purified by column chromatography to afford the title compound (400 mg, yield 54%).

1H NMR (400 MHz, CDCl$_3$) δ 9.90 (s, 1H), 9.06 (s, 1H), 8.98 (s, 1H), 8.49 (s, 1H), 8.38 (s, 1H), 8.25 (d, J=4.0 Hz, 1H), 8.13 (s, 1H), 7.57 (d, J=4.0 Hz, 1H), 3.95 (s, 3H), 3.71-0.64 (m, 1H), 3.60 (s, 2H), 3.45-3.40 (m, 2H), 3.15-3.10 (m, 2H).

m/z=435[M+1]$^+$.

Compound Evaluation

Inhibitory Activities of the Compounds on JAK1, JAK2, JAK3 and Tyk2 (IC$_{50}$)

The inhibitory activity of compounds on JAK family kinase was analyzed with Mobility shift assay. The screening platform is MSA based microfluidic chip technology, which applies the basic concept of capillary electrophoresis to microfluidic environment. The substrate used in the experiment is a poly-peptide labeled with fluorescent. Under the catalysis of kinase in the reaction system, the substrate is transformed into a product, with the charge changed accordingly. MSA technology could detect the substrate and the product with different charge separately.

The Operation is Described as Follows:

A compound (powder) was dissolved in 100% DMSO to prepare a 10 mM storage solution. The compound had an initial test concentration of 10,000 nM or 1000 nM, was 3-fold or 4-fold serially diluted to obtain 10 concentrations. Detection in duplicate. Baricitinib (Selleckchem, Cat. S2851) was used as positive control. The serially diluted compound was mixed with JAK1/JAK2/JAK3/Tyk2 kinase (Cama, Cat. 08-144/08-045/08-046/08-147) with final concentration of 5 nM/0.125 nM/0.5 nM/2.5 nM in a Optiplate-384F plate and incubated at room temperature for 10 minutes. After that, ATP with final concentration of 1 mM and 3 μM Kinase Substrate 30 (GL Biochem, Cat. 117885) were added and mixed well. The reaction was carried out at room temperature for 20 min. Stop test solution was added to stop the reaction and the conversion rate was read by Caliper EZ Reader II.

Data Analysis:

$$\% \text{ Inhibition} = \frac{\text{Conversion \%\_max} - \text{Conversion \%\_sample}}{\text{Conversion \%\_max} - \text{Conversion \%\_min}} \times 100$$

Conversion %_sample: the conversion rate reading of the sample;

Conversion %_min: mean value of negative control, representing the conversion rate reading without kinase activity;

Coversion %_max: mean value of positive control, representing the conversion rate reading without compound inhibition.

Fitting the dose-response curve: taking the log value of concentration as X axis and the percentage inhibition rate as Y axis, the dose response curve was filled by the analysis software GraphPad Prism 5 (log(inhibitor) vs. response –Variable slope), thus the IC$_{50}$ value of each compound on inhibiting kinase activity was obtained.

TABLE 1

The inhibitory activities of the compounds on kinases

| Compounds | TyK2 IC$_{50}$ (nM) | JAK2 IC$_{50}$ (nM) | Selectivity of JAK2/TyK2 |
|---|---|---|---|
| 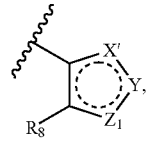 | 11 | 47 | 4.3 |
| Example 1 | 0.42 | 88 | 210 |
| Example 2 | 0.38 | 64 | 168 |
| Example 3 | 2.1 | 77 | 36.6 |
| Example 4 | 1755 | N/A | N/A |
| Example 9 | 0.17 | 14 | 82.4 |
| Example 10 | 0.13 | 0.25 | 1.9 |
| Example 38 | 0.33 | 6.7 | 20 |
| Example 39 | 3.7 | 200 | 54 |
| Example 40 | 139 | N/A | N/A |
| Example 41 | 37 | N/A | N/A |
| Example 42 | 375 | N/A | N/A |
| Example 43 | 43 | N/A | N/A |
| Example 47 | 186 | N/A | N/A |
| Example 48 | 0.36 | 8.1 | 22.5 |
| Example 49 | 118 | N/A | N/A |
| Example 50 | 0.41 | 10 | 24.4 |

Although the preferred embodiments of the present disclosure have been disclosed in order to illustrate the present disclosure, those skilled in the art should understand that various modifications, additions and replacements may be made to the present disclosure without departing from the concept and scope of the present disclosure defined by the claims.

The invention claimed is:

1. A compound represented by general formula (AI) or a pharmaceutically acceptable salt, polymorph, isotopically labelled compound or isomer thereof,

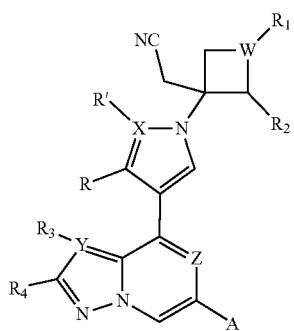

AI wherein,

WR$_1$ represents —(CR$_5$R$_1$)— or —(NR$_1$)—;

A represents —OR" or

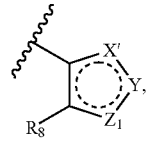

where X', Y and Z$_1$ independently represent —O—, —S—, —(CO)—, —(CS)—, —(CR$_6$)=, —(CR$_6$R$_7$)—, —N= or —(NR$_6$)—, and make the formed five-membered ring an unsaturated ring; R$_6$, R$_7$ independently represent substituted or unsubstituted hydrogen, halogen, C$_{1\sim6}$ alkyl, C$_{1\sim6}$ alkoxy, C$_{1\sim6}$ haloalkyl, hydroxy, mercapto, amino, cyano, C$_{1\sim4}$ hydroxyalkylene, C$_{1\sim4}$ mercaptoalkylene, C$_{1\sim4}$ aminoalkylene, C$_{1\sim4}$ cyanoalkylene, —NR$_9$COR$_{10}$, —COR$_9$ or —CONR$_9$R$_{10}$;

R" represents C$_1$-C$_6$ alkyl substituted with hydroxy, methoxy or amino;

R represents substituted or unsubstituted-NR$_9$R$_{10}$, or R' and R and the atoms on the ring to which they are connected together form a six-membered heteroaromatic ring;

XR' represents —(N)— or —(CR')—; when XR' represents —(CR')—, R' and R and the atoms on the ring to which they are connected together form a six-membered or five-membered aromatic ring or heteroaromatic ring;

YR$_3$ represents —(N)— or —(CR$_3$)—;

Z represents —N— or —CR$_3$—;

R$_1$ represents —(CH$_2$)$_n$—R$_1$', where R$_1$' represents substituted or unsubstituted hydrogen, halogen, C$_{1\sim6}$ alkyl, C$_{1\sim6}$ alkoxy, C$_{1\sim6}$ haloalkyl, hydroxy, mercapto, amino, cyano, C$_{3\sim8}$ cycloalkyl, C$_{3\sim8}$ heterocyclyl, C$_{6\sim20}$ aryl, C$_{3\sim20}$ heteroaryl, —NR$_9$COR$_{10}$, —CONR$_9$R$_{10}$, —COR$_9$, —SOR$_9$ or —SO$_2$R$_9$, and n represents an integer from 0 to 4;

R$_2$~R$_5$ independently represent substituted or unsubstituted hydrogen, halogen, C$_{1\sim6}$ alkyl, C$_{1\sim6}$ alkoxy, C$_{1\sim6}$ haloalkyl, hydroxy, mercapto, amino or cyano;

R$_8$ represents —(CH$_2$)$_n$—R$_8$', where R$_8$' represents substituted or unsubstituted hydrogen, halogen, C$_{1\sim6}$ alkyl, C$_{1\sim6}$ alkoxy, C$_{1\sim6}$ haloalkyl, hydroxy, mercapto, cyano or —NR$_9$R$_{10}$, and n represents an integer from 0 to 4;

R$_9$, R$_{10}$ independently represent substituted or unsubstituted C$_{1\sim6}$ alkyl, C$_{1\sim6}$ alkoxy, or C$_{1\sim6}$ haloalkyl;

the substituents of the above groups, if any, may be selected from halogen, C$_{1\sim6}$ alkyl, C$_{1\sim6}$ haloalkyl, C$_{1\sim6}$ alkoxy, C$_{1\sim6}$ alkylsulfanyl, C$_{3\sim8}$ cycloalkyl, C$_{3\sim8}$ heterocyclyl, C$_{6\sim20}$ aryl, C$_{3\sim20}$ heteroaryl, C$_{1\sim6}$ alkyl ester group, C$_{1\sim6}$ alkyl acyl, C$_{1\sim6}$ alkylsufonyl, amino, hydroxyl, mercapto, carboxyl, nitro, amido, or cyano.

2. The compound according to claim 1 represented by general formula (I) or a pharmaceutically acceptable salt, polymorph, isotopically labelled compound or isomer thereof,

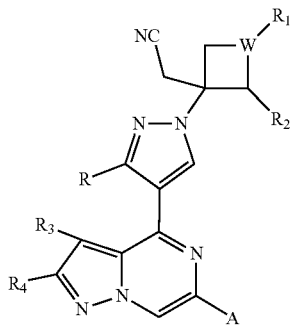

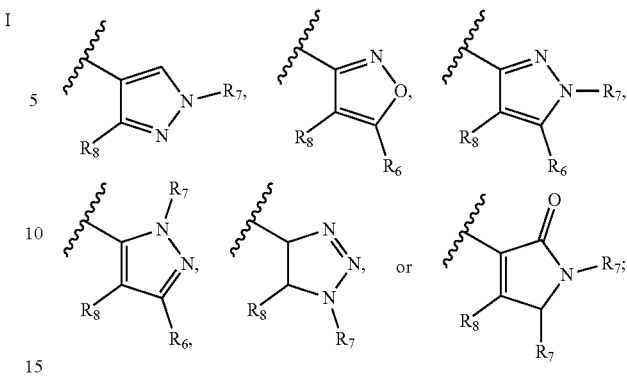

wherein,

WR$_1$ represents —(CR$_5$R$_1$)— or —(NR$_1$)—;

A represents

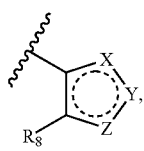

where X, Y and Z independently represent —O—, —S—, —(CO)—, —(CS)—, —(CR$_6$)=, —(CR$_6$R$_7$)—, —N= or —(NR$_6$)—, and make the formed five-membered ring an unsaturated ring; R$_6$, R$_7$ independently represent substituted or unsubstituted hydrogen, halogen, C$_{1~6}$ alkyl, C$_{1~6}$ alkoxy, C$_{1~6}$ haloalkyl, hydroxy, mercapto, amino, cyano, C$_{1~4}$ hydroxyalkylene, C$_{1~4}$ mercaptoalkylene, C$_{1~4}$ aminoalkylene, C$_{1~4}$ cyanoalkylene, —NR$_9$COR$_{10}$, —COR$_9$ or —CONR$_9$R$_{10}$;

R represents substituted or unsubstituted-NR$_9$R$_{10}$;

R$_1$ represents —(CH$_2$)$_n$—R$_{1'}$, where R$_{1'}$ represents substituted or unsubstituted hydrogen, halogen, C$_{1~6}$ alkyl, C$_{1~6}$ alkoxy, C$_{1~6}$ haloalkyl, hydroxy, mercapto, amino, cyano, C$_{3~8}$ cycloalkyl, C$_{3~8}$ heterocyclyl, C$_{6~20}$ aryl, C$_{3~20}$ heteroaryl, —NR$_9$COR$_{10}$, —CONR$_9$R$_{10}$, —COR$_9$, —SOR, or —SO$_2$R$_9$, and n represents an integer from 0 to 4;

R$_2$~R$_5$ independently represent substituted or unsubstituted hydrogen, halogen, C$_{1~6}$ alkyl, C$_{1~6}$ alkoxy, C$_{1~6}$ haloalkyl, hydroxy, mercapto, amino or cyano;

R$_8$ represents —(CH$_2$)$_n$—R$_{8'}$, where R$_{8'}$ represents substituted or unsubstituted hydrogen, halogen, C$_{1~6}$ alkyl, C$_{1~6}$ alkoxy, C$_{1~6}$ haloalkyl, hydroxy, mercapto, cyano or —NR$_9$R$_{10}$, and n represents an integer from 0 to 4;

R$_9$, R$_{10}$ independently represent substituted or unsubstituted hydrogen, halogen, C$_{1~6}$ alkyl, C$_{1~6}$ alkoxy, C$_{1~6}$ haloalkyl, hydroxy, mercapto, amino, cyano, C$_{3~8}$ cycloalkyl or C$_{3~8}$ heterocyclyl;

the substituents of the above groups, if any, may be selected from halogen, C$_{1~6}$ alkyl, C$_{1~6}$ haloalkyl, C$_{1~6}$ alkoxy, C$_{1~6}$ alkylsulfanyl, C$_{3~8}$ cycloalkyl, C$_{3~8}$ heterocyclyl, C$_{6~20}$ aryl, C$_{3~20}$ heteroaryl, C$_{1~6}$ alkyl ester group, C$_{1~6}$ alkyl acyl, C$_{1~6}$ alkylsufonyl, amino, hydroxyl, mercapto, carboxyl, nitro, amido, or cyano.

3. The compound according to claim 1, wherein A represents one of the following groups:

or a pharmaceutically acceptable salt, polymorph, isotopically labelled compound or isomer thereof.

4. The compound according to claim 3, wherein A represents the following group:

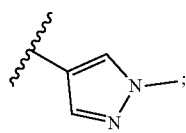 [SMILES: *c1cnn(C)c1]

or a pharmaceutically acceptable salt, polymorph, isotopically labelled compound or isomer thereof.

5. The compound according to claim 1 represented by general formula (I) or a pharmaceutically acceptable salt, polymorph, isotopically labelled compound or isomer thereof,

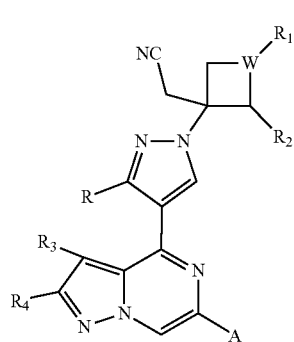

wherein,

WR$_1$ represents —(CR$_5$R$_1$)— or —(NR$_1$)—;

A represents —OR", where R" represents C$_1$-C$_6$ alkyl substituted with hydroxy, methoxy or amino;

R represents halogen, substituted or unsubstituted-NR$_9$R$_{10}$;

R$_1$ represents —(CH$_2$)$_n$—R$_{1'}$, where R$_{1'}$ represents substituted or unsubstituted hydrogen, halogen, C$_{1~6}$ alkyl, C$_{1~6}$ alkoxy, C$_{1~6}$ haloalkyl, hydroxy, mercapto, amino, cyano, C$_{3~8}$ cycloalkyl, C$_{3~8}$ heterocyclyl, C$_{6~20}$ aryl, C$_{3~20}$ heteroaryl, —NR$_9$COR$_{10}$, —CONR$_9$R$_{10}$, —COR$_9$, —SOR, or —SO$_2$R$_9$, and n represents an integer from 0 to 4;

R$_2$~R$_5$ independently represent substituted or unsubstituted hydrogen, halogen, C$_{1~6}$ alkyl, C$_{1~6}$ alkoxy, C$_{1~6}$ haloalkyl, hydroxy, mercapto, amino or cyano;

$R_8$ represents —$(CH_2)_n$—$R_{8'}$, where $R_{8'}$ represents substituted or unsubstituted hydrogen, halogen, $C_{1~6}$ alkyl, $C_{1~6}$ alkoxy, $C_{1~6}$ haloalkyl, hydroxy, mercapto, cyano or —$NR_9R_{10}$, and n represents an integer from 0 to 4;

$R_9$, $R_{10}$ independently represent substituted or unsubstituted hydrogen, halogen, $C_{1~6}$ alkyl, $C_{1~6}$ alkoxy, $C_{1~6}$ haloalkyl, hydroxy, mercapto, amino, cyano, $C_{3~8}$ cycloalkyl or $C_{3~8}$ heterocyclyl;

the substituents of the above groups, if any, may be selected from halogen, $C_{1~6}$ alkyl, $C_{1~6}$ haloalkyl, $C_{1~6}$ alkoxy, $C_{1~6}$ alkylsulfanyl, $C_{3~8}$ cycloalkyl, $C_{3~8}$ heterocyclyl, $C_{6~20}$ aryl, $C_{3~20}$ heteroaryl, $C_{1~6}$ alkyl ester group, $C_{1~6}$ alkyl acyl, $C_{1~6}$ alkylsufonyl, amino, hydroxyl, mercapto, carboxyl, nitro, amido, or cyano.

6. The compound according to claim 1, wherein A represents the following group:

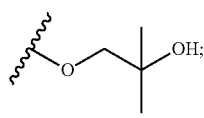 [SMILES: *OCC(C)(C)O]

or a pharmaceutically acceptable salt, polymorph, isotopically labelled compound or isomer thereof.

7. The compound according to claim 1, wherein R represents —$NH_2$; or a pharmaceutically acceptable salt, polymorph, isotopically labelled compound or isomer thereof.

8. The compound according to claim 1, wherein $R_1$ represents —$(CH_2)_n$—$R_{1'}$, and n represents 0, 1 or 2; or a pharmaceutically acceptable salt, polymorph, isotopically labelled compound or isomer thereof.

9. The compound according to claim 8, wherein $R_{1'}$ represents hydrogen, $C_{1~4}$ alkyl, $C_{1~4}$ alkoxy, $C_{1~4}$ haloalkyl, hydroxy, cyano, $C_{3~6}$ cycloalkyl, $C_{3~5}$ heteroaryl, —$COR_9$ or —$SO_2R_9$; where Ry represents $C_{1~4}$ alkyl, $C_{1~4}$ alkoxy, $C_{1~4}$ haloalkyl or $C_{3~6}$ cycloalkyl; or a pharmaceutically acceptable salt, polymorph, isotopically labelled compound or isomer thereof.

10. The compound according to claim 1, which is selected from the following compound:

1

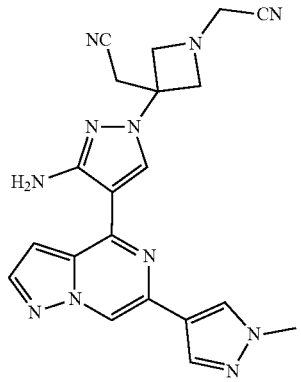

2

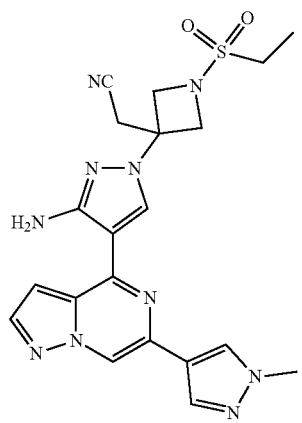

3

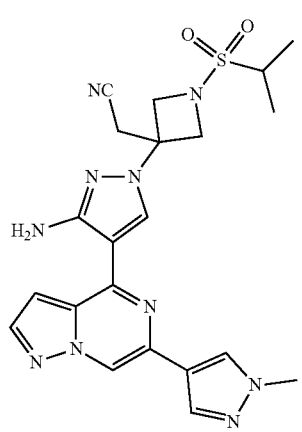

4

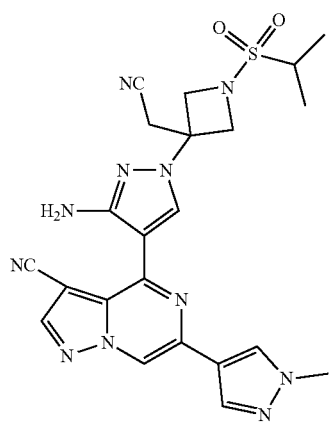

5
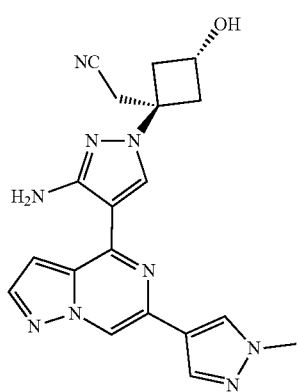
trans
6
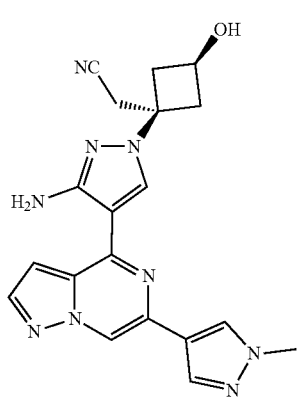
cis
7
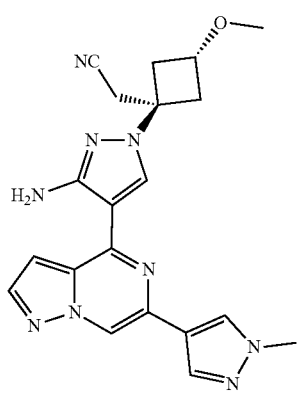
trans
8
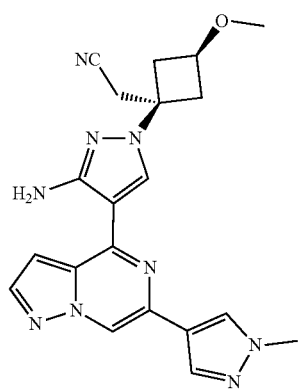
cis
9
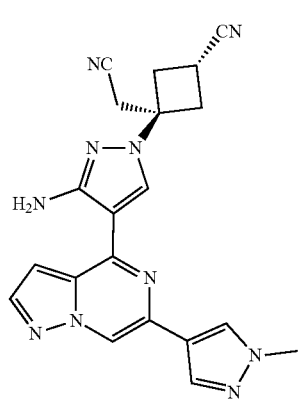
trans
10
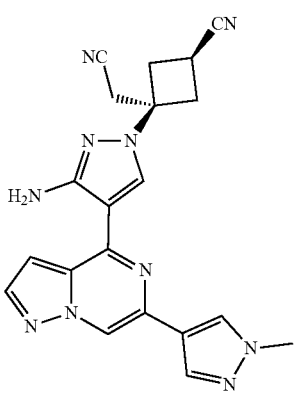
cis -continued
11
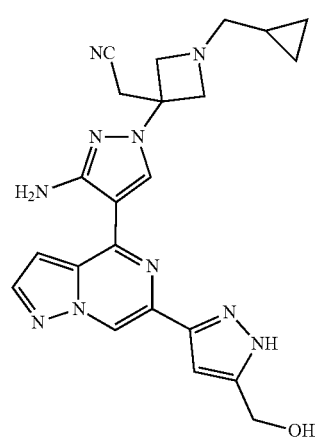
12
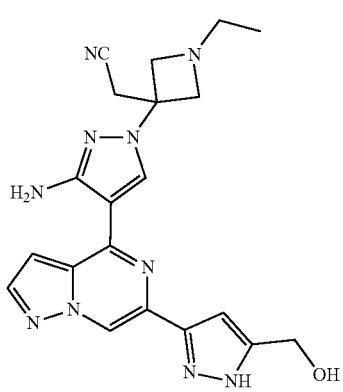
13
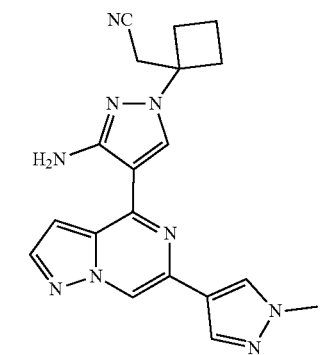
14
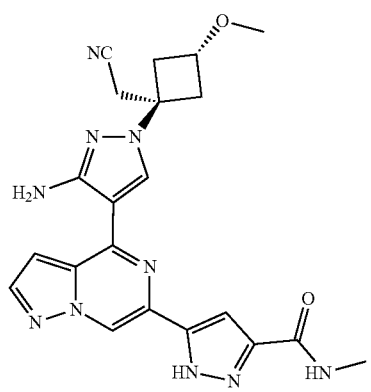
-continued
15
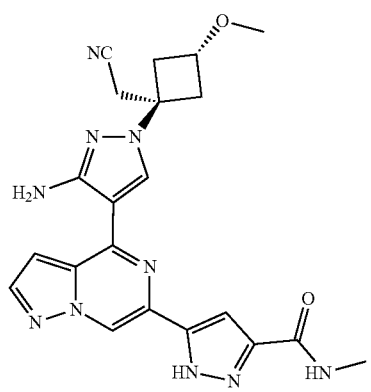
16
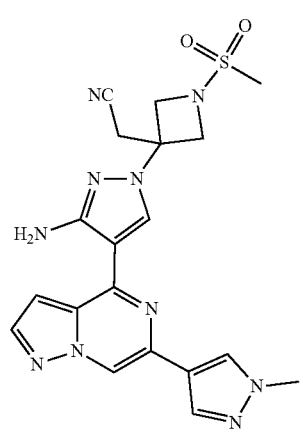
17
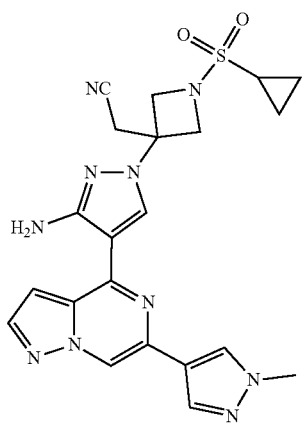
18
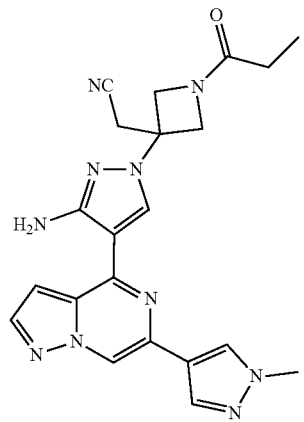

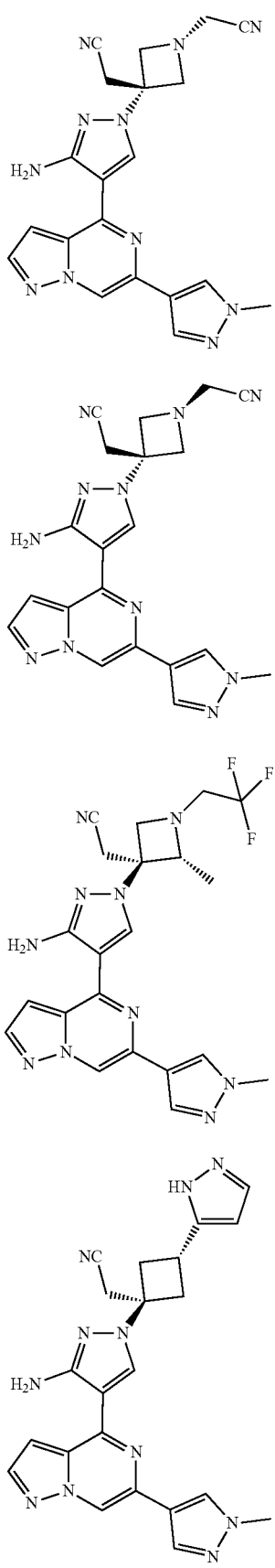
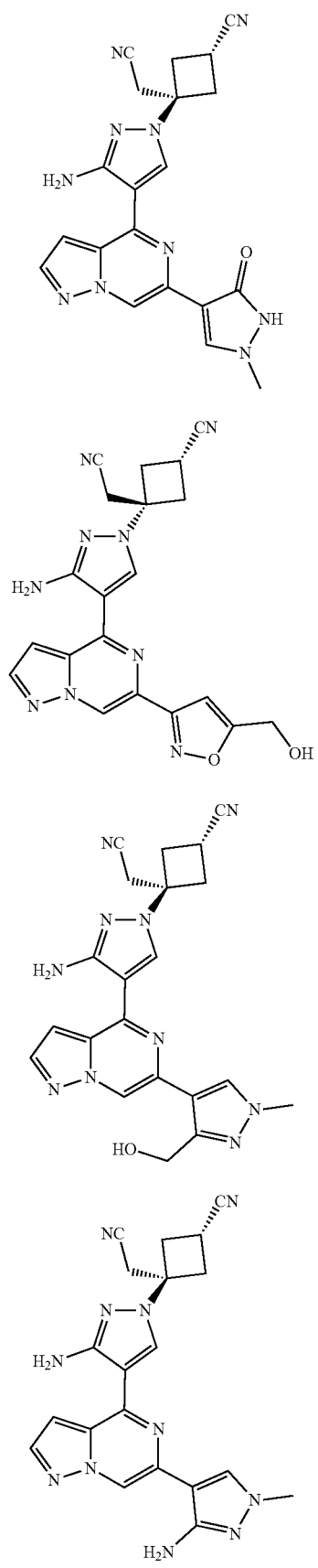

| 27 | 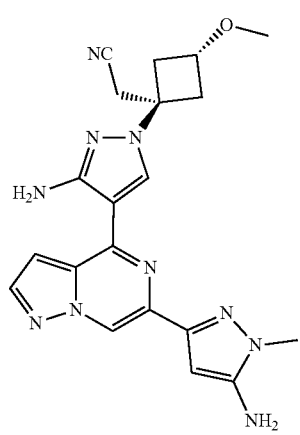 |
|---|---|
| 28 | 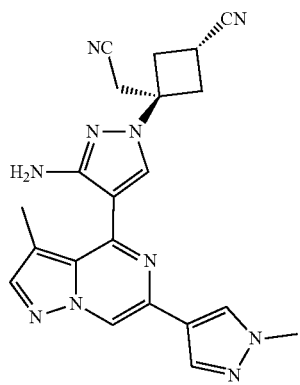 |
| 29 | 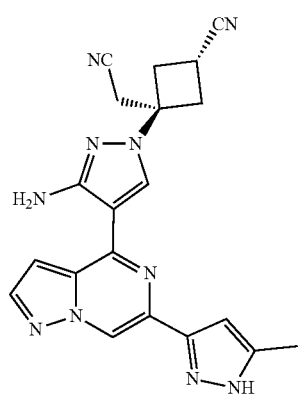 |
| 30 | 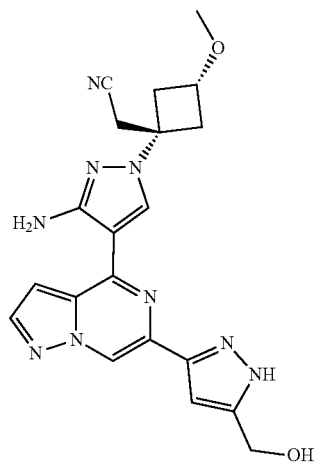 |
| 31 | 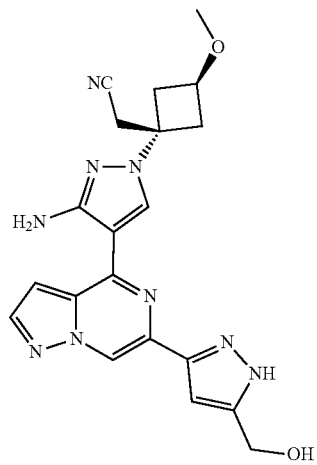 |
| 32 | 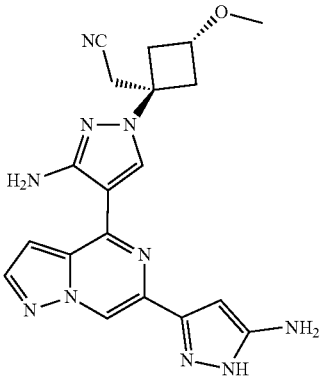 |

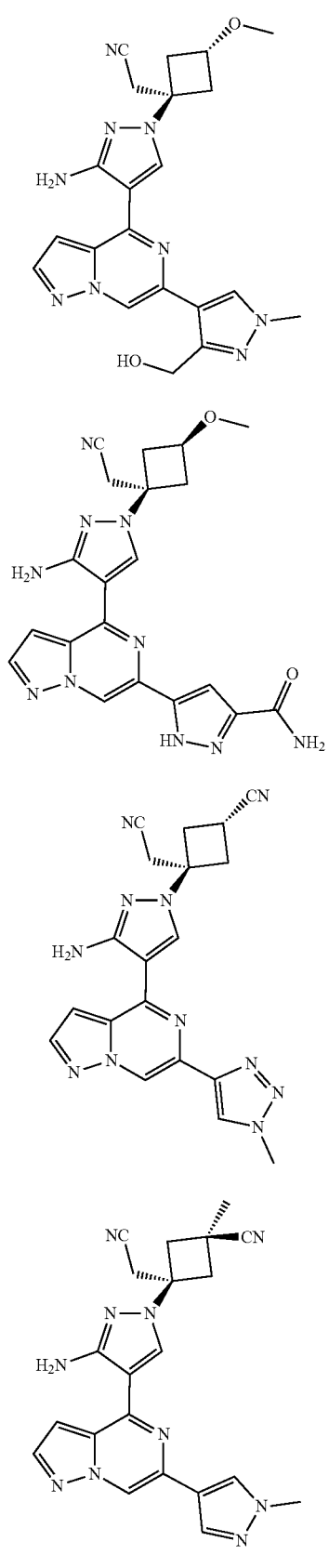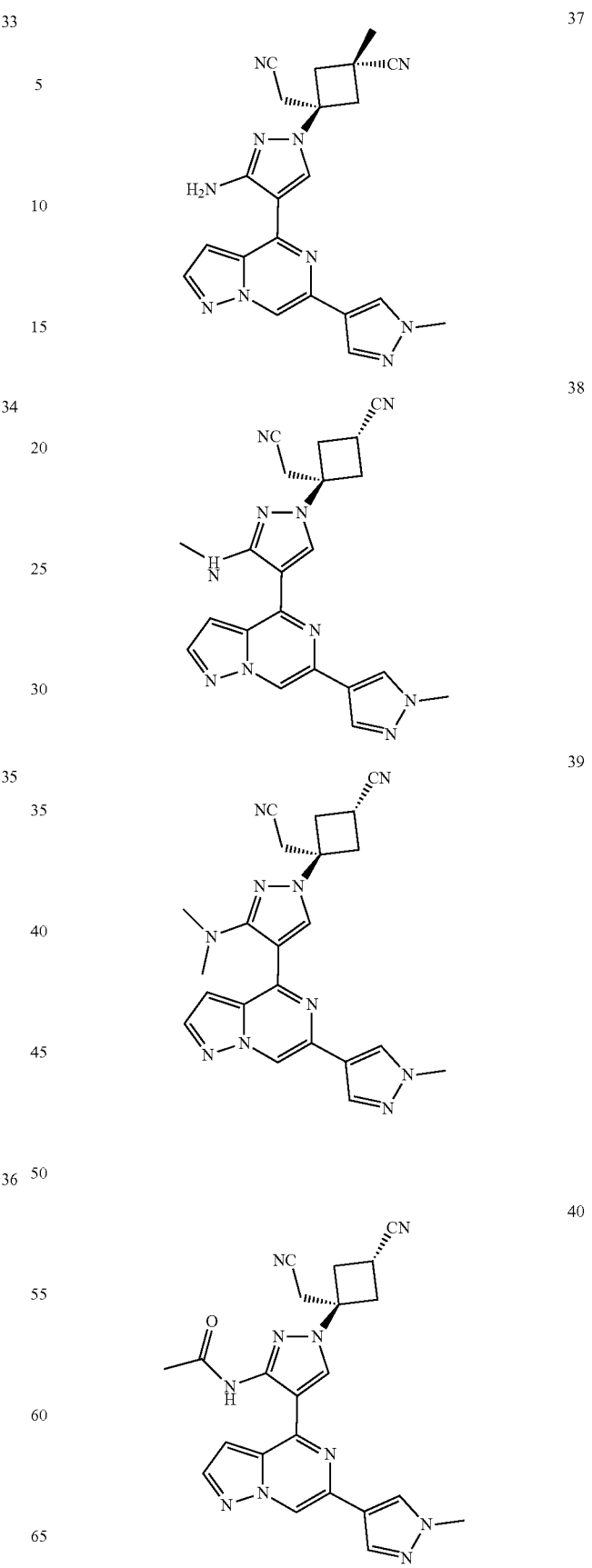

41
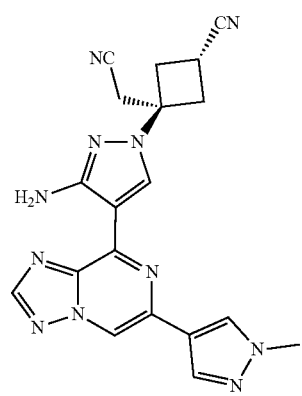
42
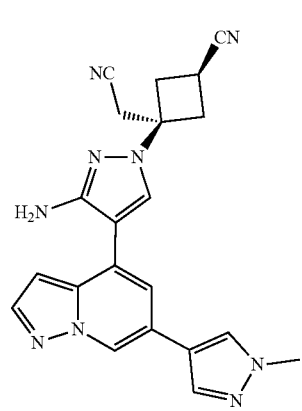
43
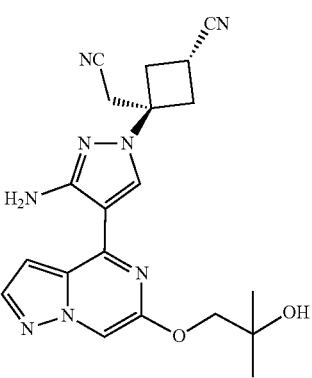
44
45
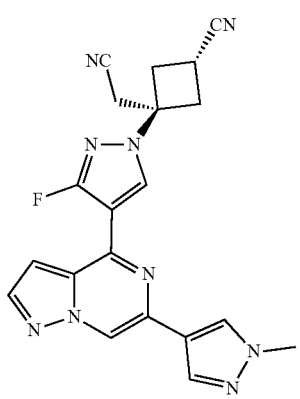
46
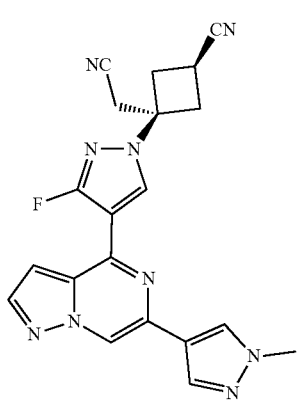
47
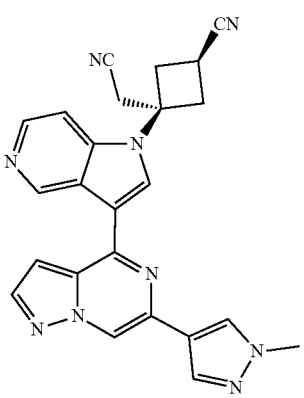

48 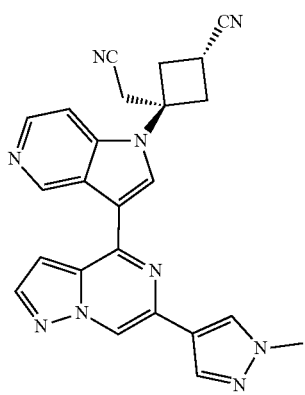

49 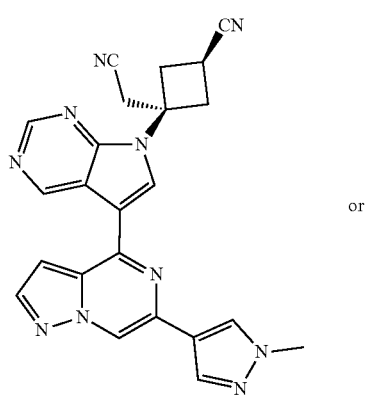

or

50 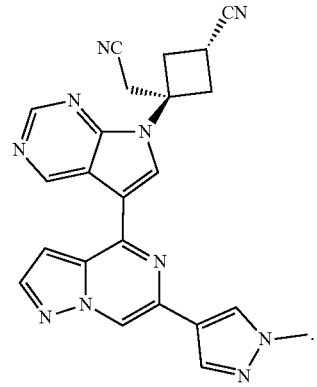

or a pharmaceutically acceptable salt, polymorph, isotopically labelled compound or isomer thereof.

11. A pharmaceutical composition comprising the compound of claim 1 or a pharmaceutically acceptable salt, polymorph, isotopically labelled compound or isomer thereof, and a pharmaceutically acceptable carrier.

12. A method for treating a disease mediated by JAK comprising a step of administering to a subject in need of such treatment an effective amount of the compound or a pharmaceutically acceptable salt, polymorph, isotopically labelled compound, or isomer thereof according to claim 1, wherein the disease mediated by JAK is selected from the group consisting of leukemia, non-small cell lung cancer, colon cancer, lymphoma, myeloproliferative tumors, myelodysplastic syndromes, rheumatoid Arthritis, psoriatic arthritis, graft-versus-host disease, non-infectious uveitis, Crohn's disease, ulcerative colitis, ankylosing spondylitis, psoriasis, atopic dermatitis, vitiligo, pruritus, scleroderma, alopecia areata, alopecia totalis, alopecia universalis, androgenetic alopecia, Behcet's disease, or dry eye syndromes.

* * * * *